US011877848B2

(12) United States Patent
Nawana et al.

(10) Patent No.: US 11,877,848 B2
(45) Date of Patent: Jan. 23, 2024

(54) DERMAL PATCH FOR COLLECTING A PHYSIOLOGICAL SAMPLE

(71) Applicant: Satio, Inc., Boston, MA (US)

(72) Inventors: Namal Nawana, Weston, MA (US); Ziad Tarik Al-Shamsie, San Diego, CA (US)

(73) Assignee: Satio, Inc., Boston, MA (US)

( * ) Notice: Subject to any disclaimer, the term of this patent is extended or adjusted under 35 U.S.C. 154(b) by 0 days.

(21) Appl. No.: 17/994,454

(22) Filed: Nov. 28, 2022

(65) Prior Publication Data

US 2023/0147048 A1    May 11, 2023

Related U.S. Application Data

(63) Continuation of application No. 17/521,466, filed on Nov. 8, 2021, now Pat. No. 11,510,602.

(51) Int. Cl.
*A61B 5/00* (2006.01)
*A61B 5/15* (2006.01)
*A61F 13/84* (2006.01)

(52) U.S. Cl.
CPC .. *A61B 5/150099* (2013.01); *A61B 5/150206* (2013.01); *A61B 5/150366* (2013.01); *A61B 5/150755* (2013.01); *A61F 13/84* (2013.01); *A61F 2013/8473* (2013.01)

(58) Field of Classification Search
CPC ........ A61B 5/150099; A61B 5/150206; A61B 5/150366; A61B 5/150755; A61B 5/150022; A61B 5/150358; A61B 5/150503; A61B 5/150969;
(Continued)

(56) References Cited

U.S. PATENT DOCUMENTS

| 5,015,228 A | 5/1991 | Columbus et al. |
| 5,338,308 A | 8/1994 | Wilk |
| 5,441,490 A | 8/1995 | Svedman |

(Continued)

FOREIGN PATENT DOCUMENTS

| AU | 2006283345 A1 | 3/2007 |
| AU | 2016266112 A1 | 12/2016 |

(Continued)

OTHER PUBLICATIONS

International Search Report and Written Opinion for PCT/US2022/046384 dated Jan. 5, 2023.

(Continued)

*Primary Examiner* — May A Abouelela
(74) *Attorney, Agent, or Firm* — Potomac Law Group, PLLC; John J. Penny, Jr.; Reza Mollaaghababa

(57) ABSTRACT

A dermal patch for collecting a physiological sample includes a housing with a collection chamber, a sample channel and a pin within a receptacle of the housing. The sample channel is configured to direct a physiological sample drawn from a subject to the collection chamber. The pin is removably positioned within the receptacle and is configured to move from an undeployed position to a deployed position. The pin is configured to seal the receptacle when in the undeployed position and is further configured to facilitate generation of negative pressure in the sample channel when the pin is moved from the undeployed to the deployed position.

3 Claims, 32 Drawing Sheets

(58) Field of Classification Search
CPC ............ A61B 5/15105; A61B 5/15117; A61B 5/15144; A61B 5/157; A61F 13/84; A61F 2013/8473

See application file for complete search history.

(56) References Cited

U.S. PATENT DOCUMENTS

| | | | |
|---|---|---|---|
| 5,527,288 A | 6/1996 | Gross et al. | |
| 5,602,037 A | 2/1997 | Ostgaard et al. | |
| 5,636,640 A * | 6/1997 | Staehlin | A61B 5/150419 600/577 |
| 5,680,872 A * | 10/1997 | Sesekura | A61B 5/15111 600/583 |
| 5,848,991 A | 12/1998 | Gross et al. | |
| 5,997,501 A | 12/1999 | Gross et al. | |
| 6,234,980 B1 * | 5/2001 | Bell | A61B 5/150305 604/314 |
| 6,315,985 B1 | 11/2001 | Wu et al. | |
| 6,454,140 B1 | 9/2002 | Jinks | |
| 6,500,150 B1 | 12/2002 | Gross et al. | |
| 6,506,168 B1 | 1/2003 | Fathallah et al. | |
| 6,524,284 B1 | 2/2003 | Marshall | |
| 6,610,273 B2 | 8/2003 | Wu et al. | |
| 6,623,457 B1 | 9/2003 | Rosenberg | |
| 6,644,517 B2 | 11/2003 | Thiel et al. | |
| 6,689,118 B2 | 2/2004 | Alchas et al. | |
| 6,776,776 B2 | 8/2004 | Alchas et al. | |
| 6,780,171 B2 | 8/2004 | Gabel et al. | |
| 6,796,429 B2 | 9/2004 | Cameron et al. | |
| 6,808,506 B2 | 10/2004 | Lastovich et al. | |
| 6,893,655 B2 | 5/2005 | Flanigan et al. | |
| 6,932,082 B2 | 8/2005 | Stein | |
| 6,960,193 B2 | 11/2005 | Rosenberg | |
| 6,994,691 B2 | 2/2006 | Ejlersen | |
| 7,004,928 B2 | 2/2006 | Aceti et al. | |
| 7,083,592 B2 | 8/2006 | Lastovich et al. | |
| 7,101,534 B1 | 9/2006 | Schultz et al. | |
| 7,156,838 B2 | 1/2007 | Gabel et al. | |
| 7,175,642 B2 | 2/2007 | Briggs et al. | |
| 7,182,955 B2 | 2/2007 | Hart et al. | |
| 7,250,037 B2 | 7/2007 | Shermer et al. | |
| 7,252,651 B2 | 8/2007 | Haider et al. | |
| 7,282,058 B2 | 10/2007 | Levin et al. | |
| 7,308,893 B2 | 12/2007 | Boot | |
| 7,435,415 B2 | 10/2008 | Gelber | |
| 7,637,891 B2 | 12/2009 | Wall | |
| 7,651,475 B2 | 1/2010 | Angel et al. | |
| 7,678,079 B2 | 3/2010 | Shermer et al. | |
| 7,846,488 B2 | 12/2010 | Johnson et al. | |
| 7,905,866 B2 | 3/2011 | Haider et al. | |
| 8,048,019 B2 | 11/2011 | Nisato et al. | |
| 8,057,842 B2 | 11/2011 | Choi et al. | |
| 8,066,680 B2 | 11/2011 | Alchas et al. | |
| 8,079,960 B2 | 12/2011 | Briggs et al. | |
| 8,104,469 B2 | 1/2012 | Dams | |
| 8,108,023 B2 | 1/2012 | Mir et al. | |
| 8,157,768 B2 | 4/2012 | Taider et al. | |
| 8,206,336 B2 | 6/2012 | Shantha | |
| 8,246,582 B2 | 8/2012 | Angel et al. | |
| 8,246,893 B2 | 8/2012 | Ferguson et al. | |
| 8,252,268 B2 | 8/2012 | Slowey et al. | |
| 8,267,889 B2 | 9/2012 | Cantor et al. | |
| 8,303,518 B2 | 11/2012 | Aceti et al. | |
| D681,195 S | 4/2013 | Skulley et al. | |
| 8,409,140 B2 | 4/2013 | Ejlersen et al. | |
| 8,414,503 B2 | 4/2013 | Briggs et al. | |
| 8,414,959 B2 | 4/2013 | Hye-Ok et al. | |
| 8,430,097 B2 | 4/2013 | Jinks et al. | |
| 8,459,253 B2 | 6/2013 | Howgill | |
| 8,491,500 B2 | 7/2013 | Briggs et al. | |
| 8,496,601 B2 | 7/2013 | Briggs et al. | |
| D687,550 S | 8/2013 | Moeckly et al. | |
| D687,551 S | 8/2013 | Moeckly et al. | |
| D687,945 S | 8/2013 | Brewer et al. | |
| D687,946 S | 8/2013 | Brewer et al. | |
| D687,947 S | 8/2013 | Brewer et al. | |
| 8,512,244 B2 | 8/2013 | Jennewine | |
| 8,517,019 B2 | 8/2013 | Brewer et al. | |
| 8,554,317 B2 | 10/2013 | Duan | |
| 8,556,861 B2 | 10/2013 | Tsals | |
| 8,561,795 B2 | 10/2013 | Schott | |
| D693,921 S | 11/2013 | Burton et al. | |
| 8,602,271 B2 | 12/2013 | Winker et al. | |
| 8,603,040 B2 | 12/2013 | Haider et al. | |
| 8,608,889 B2 | 12/2013 | Sever et al. | |
| 8,622,963 B2 | 1/2014 | Iwase et al. | |
| 8,696,619 B2 | 4/2014 | Schnall | |
| 8,696,637 B2 | 4/2014 | Ross | |
| D705,422 S | 5/2014 | Burton et al. | |
| 8,715,232 B2 | 5/2014 | Yodfat et al. | |
| 8,740,014 B2 | 6/2014 | Purkins et al. | |
| 8,741,377 B2 | 6/2014 | Choi et al. | |
| 8,784,363 B2 | 7/2014 | Frederickson et al. | |
| 8,808,202 B2 | 8/2014 | Brancazio | |
| 8,808,786 B2 | 8/2014 | Jinks et al. | |
| 8,814,009 B2 | 8/2014 | Hodson et al. | |
| 8,814,035 B2 | 8/2014 | Stuart | |
| 8,821,412 B2 | 9/2014 | Gonzalez-Zugasti et al. | |
| 8,821,446 B2 | 9/2014 | Trautman et al. | |
| 8,821,779 B2 | 9/2014 | Ferguson et al. | |
| 8,827,971 B2 | 9/2014 | Gonzalez-Zugasti et al. | |
| 8,870,821 B2 | 10/2014 | Laufer | |
| 8,900,180 B2 | 12/2014 | Wolter et al. | |
| 8,900,194 B2 | 12/2014 | Clarke et al. | |
| 8,945,071 B2 | 2/2015 | Christensen | |
| 8,961,431 B2 | 2/2015 | Roe et al. | |
| 9,022,973 B2 | 5/2015 | Sexton et al. | |
| 9,033,898 B2 | 5/2015 | Chickering, III et al. | |
| 9,041,541 B2 | 5/2015 | Levinson et al. | |
| D733,290 S | 6/2015 | Burton et al. | |
| 9,067,031 B2 | 6/2015 | Jinks et al. | |
| 9,072,664 B2 | 7/2015 | Stein et al. | |
| 9,089,661 B2 | 7/2015 | Stuart et al. | |
| 9,089,677 B2 | 7/2015 | Soo et al. | |
| 9,113,836 B2 | 8/2015 | Bernstein et al. | |
| 9,119,578 B2 | 9/2015 | Haghgooie et al. | |
| 9,119,945 B2 | 9/2015 | Simons et al. | |
| 9,133,024 B2 | 9/2015 | Phan et al. | |
| 9,144,651 B2 | 9/2015 | Stuart | |
| 9,144,671 B2 | 9/2015 | Cantor et al. | |
| 9,173,994 B2 | 11/2015 | Ziaie et al. | |
| 9,174,035 B2 | 11/2015 | Ringsred et al. | |
| 9,186,097 B2 | 11/2015 | Frey et al. | |
| 9,227,021 B2 | 1/2016 | Buss | |
| 9,289,763 B2 | 3/2016 | Berthier et al. | |
| 9,289,925 B2 | 3/2016 | Ferguson et al. | |
| 9,289,968 B2 | 3/2016 | Sever et al. | |
| 9,295,417 B2 | 3/2016 | Haghgooie et al. | |
| 9,295,987 B2 | 3/2016 | Kelly et al. | |
| 9,339,956 B2 | 5/2016 | Rendon | |
| 9,380,972 B2 | 7/2016 | Fletcher et al. | |
| 9,380,973 B2 | 7/2016 | Fletcher et al. | |
| 9,468,404 B2 | 10/2016 | Hayden | |
| 9,480,428 B2 | 11/2016 | Colin et al. | |
| 9,504,813 B2 | 11/2016 | Buss | |
| 9,522,225 B2 | 12/2016 | Chong et al. | |
| 9,549,700 B2 | 1/2017 | Fletcher et al. | |
| 9,555,187 B2 | 1/2017 | Sonderegger et al. | |
| 9,566,393 B2 | 2/2017 | Iwase et al. | |
| 9,579,461 B2 | 2/2017 | Sonderegger et al. | |
| 9,623,087 B2 | 4/2017 | Zhang et al. | |
| 9,642,895 B2 | 5/2017 | Dai et al. | |
| 9,643,229 B2 | 5/2017 | Wilson et al. | |
| 9,675,675 B2 | 6/2017 | Zhang et al. | |
| 9,675,752 B2 | 6/2017 | Christensen | |
| 9,682,222 B2 | 6/2017 | Burton et al. | |
| 9,693,950 B2 | 7/2017 | Determan et al. | |
| 9,694,149 B2 | 7/2017 | Jinks et al. | |
| 9,717,850 B2 | 8/2017 | Sonderegger | |
| 9,724,462 B2 | 8/2017 | Rotem | |
| 9,730,624 B2 | 8/2017 | Gonzalez-Zugasti et al. | |
| 9,770,578 B2 | 9/2017 | Chowdhury | |
| 9,775,551 B2 | 10/2017 | Bernstein et al. | |
| 9,782,574 B2 | 10/2017 | Simmers | |

(56) References Cited

U.S. PATENT DOCUMENTS

| | | | |
|---|---|---|---|
| 9,789,249 B2 | 10/2017 | Frederickson et al. |
| 9,789,299 B2 | 10/2017 | Simmers |
| 9,844,631 B2 | 12/2017 | Bureau |
| 9,849,270 B2 | 12/2017 | Stockholm |
| D808,515 S | 1/2018 | Atkin et al. |
| 9,861,580 B2 | 1/2018 | Mueting et al. |
| 9,861,801 B2 | 1/2018 | Baker et al. |
| 9,872,975 B2 | 1/2018 | Burton et al. |
| 9,884,151 B2 | 2/2018 | Sullivan et al. |
| 9,895,520 B2 | 2/2018 | Burton et al. |
| 9,956,170 B2 | 5/2018 | Cantor et al. |
| 9,968,767 B1 | 5/2018 | Hasan et al. |
| 9,987,629 B2 | 6/2018 | Berthier et al. |
| 9,993,189 B2 | 6/2018 | Phan et al. |
| 10,004,887 B2 | 6/2018 | Gross et al. |
| 10,010,676 B2 | 7/2018 | Bureau |
| 10,010,706 B2 | 7/2018 | Gonzalez et al. |
| 10,010,707 B2 | 7/2018 | Colburn et al. |
| 10,016,315 B2* | 7/2018 | Letourneau | A61F 13/15 |
| 10,029,845 B2 | 7/2018 | Jinks |
| 10,035,008 B2 | 7/2018 | Brandwein et al. |
| 10,076,649 B2 | 9/2018 | Gilbert et al. |
| 10,080,843 B2 | 9/2018 | Bureau |
| 10,080,846 B2 | 9/2018 | Sonderegger et al. |
| 10,099,043 B2 | 10/2018 | Berry et al. |
| 10,105,524 B2 | 10/2018 | Meyer et al. |
| 10,111,807 B2 | 10/2018 | Baker et al. |
| D834,704 S | 11/2018 | Atkin et al. |
| 10,154,957 B2 | 12/2018 | Zhang et al. |
| 10,155,334 B2 | 12/2018 | Rendon |
| 10,183,156 B2 | 1/2019 | Ross et al. |
| 10,188,335 B2 | 1/2019 | Haghgooie et al. |
| D840,020 S | 2/2019 | Howgill |
| 10,201,691 B2 | 2/2019 | Berry et al. |
| 10,232,157 B2 | 3/2019 | Berry et al. |
| 10,232,160 B2 | 3/2019 | Baker et al. |
| 10,248,765 B1 | 4/2019 | Holmes et al. |
| 10,265,484 B2 | 4/2019 | Stuart et al. |
| 10,272,214 B2 | 4/2019 | Child et al. |
| 10,300,260 B2 | 5/2019 | Wirtanen et al. |
| 10,307,578 B2 | 6/2019 | Frederickson et al. |
| 10,315,021 B2 | 6/2019 | Frederickson et al. |
| 10,327,990 B2 | 6/2019 | Egeland et al. |
| 10,328,248 B2 | 6/2019 | Baker et al. |
| 10,335,560 B2 | 7/2019 | Stein et al. |
| 10,335,562 B2 | 7/2019 | Jinks et al. |
| 10,335,563 B2 | 7/2019 | Brewer et al. |
| 10,357,610 B2 | 7/2019 | Sonderegger |
| 10,384,047 B2 | 8/2019 | Simmers |
| 10,391,290 B2 | 8/2019 | Burton et al. |
| 10,398,885 B2 | 9/2019 | Frits et al. |
| 10,406,339 B2 | 9/2019 | Simmers |
| 10,410,838 B2 | 9/2019 | Hanson et al. |
| 10,426,390 B2 | 10/2019 | Berthier et al. |
| 10,426,739 B2 | 10/2019 | Knutson |
| 10,478,346 B2 | 11/2019 | Knutson |
| 10,492,716 B2 | 12/2019 | Berthier et al. |
| 10,507,286 B2 | 12/2019 | Egeland et al. |
| 10,518,071 B2 | 12/2019 | Kulkarni |
| D872,853 S | 1/2020 | Stuart et al. |
| 10,525,463 B2 | 1/2020 | Kelly et al. |
| 10,542,922 B2 | 1/2020 | Sia et al. |
| 10,543,310 B2 | 1/2020 | Bernstein et al. |
| 10,549,079 B2 | 2/2020 | Burton et al. |
| 10,568,937 B2 | 2/2020 | Hattersley et al. |
| D878,544 S | 3/2020 | Stuart et al. |
| 10,576,257 B2 | 3/2020 | Berry et al. |
| 10,596,333 B2 | 3/2020 | Howgill |
| 10,598,583 B1* | 3/2020 | Peeters | A61B 5/150099 |
| 10,638,963 B2 | 5/2020 | Beyerlein et al. |
| 10,646,703 B2 | 5/2020 | Chowdhury |
| 10,653,349 B2 | 5/2020 | Delamarche et al. |
| 10,695,289 B2 | 6/2020 | Brown et al. |
| 10,695,547 B2 | 6/2020 | Burton et al. |
| 10,716,926 B2 | 7/2020 | Burton et al. |
| 10,729,842 B2 | 8/2020 | Hooven et al. |
| 10,772,550 B2 | 9/2020 | Aceti et al. |
| 10,779,757 B2 | 9/2020 | Berthier et al. |
| 10,799,166 B2 | 10/2020 | Gonzalez-Zugasti et al. |
| 10,835,163 B2 | 11/2020 | Haghgooie et al. |
| 10,881,342 B2 | 1/2021 | Kelly et al. |
| 10,888,259 B2 | 1/2021 | Jordan et al. |
| 10,926,030 B2 | 2/2021 | Lanigan et al. |
| 10,932,710 B2 | 3/2021 | Jordan et al. |
| 10,939,860 B2 | 3/2021 | Levinson et al. |
| 10,940,085 B2 | 3/2021 | Baker et al. |
| 10,953,211 B2 | 3/2021 | Ross et al. |
| 11,020,548 B2 | 6/2021 | Stuart et al. |
| 11,033,212 B2 | 6/2021 | Berthier et al. |
| 11,040,183 B2 | 6/2021 | Baker et al. |
| 11,103,685 B2 | 8/2021 | Gonzalez et al. |
| 11,110,234 B2 | 9/2021 | Richardson et al. |
| 11,116,953 B2 | 9/2021 | Kobayashi et al. |
| 11,147,955 B2 | 10/2021 | Gross et al. |
| 11,177,029 B2 | 11/2021 | Levinson et al. |
| 11,197,625 B1 | 12/2021 | Schleicher et al. |
| 11,202,895 B2 | 12/2021 | Davis et al. |
| 11,207,477 B2 | 12/2021 | Hodson |
| 11,247,033 B2 | 2/2022 | Baker et al. |
| 11,253,179 B2 | 2/2022 | Bernstein et al. |
| 11,266,337 B2 | 3/2022 | Jackson et al. |
| 11,273,272 B2 | 3/2022 | Stuart et al. |
| 11,291,989 B2 | 4/2022 | Morrison |
| 11,298,060 B2 | 4/2022 | Jordan et al. |
| 11,298,478 B2 | 4/2022 | Stuart et al. |
| 11,304,632 B2 | 4/2022 | Mou et al. |
| 11,344,684 B2 | 5/2022 | Richardson et al. |
| 11,395,614 B2 | 7/2022 | Berthier et al. |
| 11,458,289 B2 | 10/2022 | Moeckly et al. |
| 11,497,712 B2 | 11/2022 | Stein et al. |
| 11,497,866 B2 | 11/2022 | Howgill |
| 11,510,602 B1 | 11/2022 | Nawana et al. |
| 2002/0077584 A1* | 6/2002 | Lin | A61B 5/150984 |
| | | | 604/21 |
| 2002/0193740 A1 | 12/2002 | Alchas et al. |
| 2004/0002121 A1 | 1/2004 | Regan et al. |
| 2004/0059256 A1* | 3/2004 | Perez | A61B 5/15113 |
| | | | 600/583 |
| 2004/0059366 A1* | 3/2004 | Sato | A61B 5/150068 |
| | | | 606/182 |
| 2004/0106904 A1 | 6/2004 | Gonnelli et al. |
| 2004/0162467 A1* | 8/2004 | Cook | A61B 5/150351 |
| | | | 600/309 |
| 2005/0106713 A1 | 5/2005 | Phan et al. |
| 2005/0118388 A1 | 6/2005 | Kingsford |
| 2006/0047243 A1 | 3/2006 | Rosenberg |
| 2006/0068490 A1 | 3/2006 | Tang et al. |
| 2006/0142651 A1 | 6/2006 | Brister et al. |
| 2007/0004989 A1 | 1/2007 | Dhillon |
| 2007/0191696 A1* | 8/2007 | Mischler | G01N 21/552 |
| | | | 600/347 |
| 2008/0003274 A1 | 1/2008 | Kaiser |
| 2008/0287864 A1 | 11/2008 | Rosenberg |
| 2009/0012472 A1 | 1/2009 | Ahm et al. |
| 2009/0036826 A1 | 2/2009 | Sage, Jr. et al. |
| 2009/0112125 A1 | 4/2009 | Tamir |
| 2009/0198215 A1 | 8/2009 | Chong et al. |
| 2009/0259176 A1 | 10/2009 | Yairi |
| 2010/0249560 A1 | 9/2010 | Levinson et al. |
| 2010/0256524 A1 | 10/2010 | Levinson et al. |
| 2010/0269837 A1 | 10/2010 | Levinson et al. |
| 2010/0272652 A1 | 10/2010 | Levinson |
| 2011/0009847 A1 | 1/2011 | Levinson et al. |
| 2011/0060280 A1 | 3/2011 | Caffey et al. |
| 2011/0105872 A1 | 5/2011 | Chickering, III et al. |
| 2011/0105951 A1 | 5/2011 | Bernstein et al. |
| 2011/0105952 A1 | 5/2011 | Bernstein et al. |
| 2011/0125058 A1 | 5/2011 | Levinson et al. |
| 2011/0144463 A1 | 6/2011 | Pesach et al. |
| 2011/0172508 A1 | 7/2011 | Chickering, III et al. |
| 2011/0172510 A1 | 7/2011 | Chickering, III et al. |
| 2011/0213335 A1 | 9/2011 | Burton et al. |
| 2011/0245635 A1* | 10/2011 | Fujiwara | A61B 5/15117 |
| | | | 600/573 |

(56) References Cited

U.S. PATENT DOCUMENTS

| | | |
|---|---|---|
| 2011/0288389 A9 | 11/2011 | Levinson et al. |
| 2012/0016308 A1* | 1/2012 | Schott ............... A61B 5/150984 604/173 |
| 2012/0041338 A1 | 2/2012 | Chickering et al. |
| 2012/0078224 A1 | 3/2012 | Emer et al. |
| 2012/0109066 A1 | 5/2012 | Chase et al. |
| 2012/0123297 A1* | 5/2012 | Brancazio ........ A61B 5/150022 600/576 |
| 2012/0259599 A1 | 10/2012 | Deck et al. |
| 2012/0271123 A1 | 10/2012 | Castle et al. |
| 2012/0271125 A1 | 10/2012 | Bernstein et al. |
| 2012/0275955 A1 | 11/2012 | Haghgooie et al. |
| 2012/0277629 A1* | 11/2012 | Bernstein ......... A61B 5/150022 600/578 |
| 2012/0277696 A1 | 11/2012 | Gonzalez-Zugasti et al. |
| 2012/0277697 A1* | 11/2012 | Haghgooie ........ A61B 5/14514 604/327 |
| 2013/0018279 A1* | 1/2013 | Plante ............... A61B 5/150755 600/583 |
| 2013/0158468 A1* | 6/2013 | Bernstein ................ A61M 1/38 604/173 |
| 2013/0158482 A1 | 6/2013 | Davis et al. |
| 2013/0211289 A1 | 8/2013 | Moga et al. |
| 2013/0253446 A1 | 9/2013 | Duan et al. |
| 2014/0066843 A1 | 3/2014 | Zhang et al. |
| 2014/0109900 A1 | 4/2014 | Jinks |
| 2014/0194854 A1 | 7/2014 | Tsals |
| 2014/0305823 A1* | 10/2014 | Gelfand ........... A61B 5/150221 600/583 |
| 2014/0309555 A1* | 10/2014 | Gelfand ........... A61B 5/150748 600/583 |
| 2014/0309557 A1 | 10/2014 | Fletcher et al. |
| 2014/0336616 A1 | 11/2014 | Edwards |
| 2015/0057510 A1 | 2/2015 | Levinson et al. |
| 2015/0057901 A1 | 2/2015 | Sundholm et al. |
| 2015/0073385 A1 | 3/2015 | Lyon et al. |
| 2015/0087944 A1 | 3/2015 | Levinson et al. |
| 2015/0136122 A1 | 5/2015 | Stuart et al. |
| 2015/0250959 A1 | 9/2015 | Stuart et al. |
| 2015/0258272 A1 | 9/2015 | Sullivan et al. |
| 2015/0278476 A1 | 10/2015 | Levinson et al. |
| 2015/0352295 A1 | 12/2015 | Burton et al. |
| 2016/0038068 A1 | 2/2016 | Chickering, III et al. |
| 2016/0051981 A1 | 2/2016 | Berthier et al. |
| 2016/0067468 A1 | 3/2016 | Chowdhury |
| 2016/0136365 A1 | 5/2016 | Stuart et al. |
| 2016/0144100 A1 | 5/2016 | Gharib et al. |
| 2016/0199581 A1 | 7/2016 | Cachemaille et al. |
| 2016/0213295 A1* | 7/2016 | Matsunami ...... A61B 5/150732 |
| 2016/0256095 A1* | 9/2016 | Krasnow .......... A61B 5/150076 |
| 2016/0262676 A1 | 9/2016 | Haghgooie et al. |
| 2016/0315123 A1 | 10/2016 | Kim et al. |
| 2016/0324506 A1* | 11/2016 | Tariyal ............. A61B 5/150755 |
| 2016/0354589 A1 | 12/2016 | Kobayashi et al. |
| 2016/0361006 A1 | 12/2016 | Bullington et al. |
| 2017/0001192 A1 | 1/2017 | Kelly et al. |
| 2017/0014822 A1 | 1/2017 | Ker |
| 2017/0021067 A1* | 1/2017 | Todd ................ A61B 5/150099 |
| 2017/0021117 A1 | 1/2017 | Howgill |
| 2017/0035337 A1* | 2/2017 | Wilkinson ....... A61B 5/150267 |
| 2017/0035975 A1 | 2/2017 | Myung et al. |
| 2017/0043103 A1 | 2/2017 | Wotton et al. |
| 2017/0059304 A1 | 3/2017 | Ma et al. |
| 2017/0120022 A1 | 5/2017 | Chickering, III et al. |
| 2017/0122846 A1 | 5/2017 | Holmes et al. |
| 2017/0127991 A1 | 5/2017 | Bernstein et al. |
| 2017/0173288 A1 | 6/2017 | Stam et al. |
| 2017/0197029 A1 | 7/2017 | Cindrich et al. |
| 2017/0224912 A1 | 8/2017 | Yodfat et al. |
| 2017/0231543 A1 | 8/2017 | Cunningham et al. |
| 2017/0290977 A1 | 10/2017 | Schauderna et al. |
| 2018/0001029 A1 | 1/2018 | Egeland et al. |
| 2018/0008183 A1 | 1/2018 | Chickering, III et al. |
| 2018/0008703 A1 | 1/2018 | Johnson |
| 2018/0008808 A1 | 1/2018 | Chowdhury |
| 2018/0021559 A1 | 1/2018 | Xu |
| 2018/0078241 A1 | 3/2018 | Moga et al. |
| 2018/0103884 A1* | 4/2018 | Delamarche ..... A61B 5/150221 |
| 2018/0126058 A1 | 5/2018 | David et al. |
| 2018/0132515 A1 | 5/2018 | Lawrence et al. |
| 2018/0132774 A1 | 5/2018 | Gonzalez-Zugasti et al. |
| 2018/0242890 A1* | 8/2018 | Chickering, III .......... A61B 5/150221 |
| 2018/0243543 A1 | 8/2018 | Baek et al. |
| 2018/0296148 A1* | 10/2018 | Gelfand ............. A61M 1/3406 |
| 2018/0344631 A1 | 12/2018 | Zhang et al. |
| 2018/0369512 A1 | 12/2018 | Blatchford et al. |
| 2019/0000365 A1* | 1/2019 | Beyerlein ............ G01N 33/487 |
| 2019/0001076 A1 | 1/2019 | Solomon et al. |
| 2019/0001081 A1 | 1/2019 | Guion et al. |
| 2019/0001085 A1 | 1/2019 | Cottenden et al. |
| 2019/0015584 A1 | 1/2019 | Meehan et al. |
| 2019/0015827 A1 | 1/2019 | Berthier et al. |
| 2019/0022339 A1 | 1/2019 | Richardson et al. |
| 2019/0023473 A1 | 1/2019 | Schott |
| 2019/0030260 A1 | 1/2019 | Wotton et al. |
| 2019/0053740 A1 | 2/2019 | Bernstein et al. |
| 2019/0054010 A1 | 2/2019 | Slowey et al. |
| 2019/0142318 A1* | 5/2019 | Diebold ........... A61B 5/150022 600/575 |
| 2019/0159709 A1 | 5/2019 | Barone et al. |
| 2019/0209820 A1 | 7/2019 | Chickering, III et al. |
| 2019/0240470 A1 | 8/2019 | Frederickson et al. |
| 2019/0298943 A1 | 10/2019 | Stuart et al. |
| 2019/0336058 A1 | 11/2019 | Haghgooie et al. |
| 2019/0366067 A1 | 12/2019 | Ginggen et al. |
| 2020/0009364 A1 | 1/2020 | Amir |
| 2020/0010219 A1 | 1/2020 | Felippone et al. |
| 2020/0011860 A1 | 1/2020 | Nawana et al. |
| 2020/0033008 A1 | 1/2020 | Baker |
| 2020/0069897 A1 | 3/2020 | Hodson et al. |
| 2020/0085414 A1* | 3/2020 | Berthier ............. A61B 5/15117 |
| 2020/0101219 A1 | 4/2020 | Wang et al. |
| 2020/0147209 A1 | 5/2020 | Johnson |
| 2020/0163603 A1 | 5/2020 | Jordan et al. |
| 2020/0164359 A1 | 5/2020 | Jordan et al. |
| 2020/0246560 A1 | 8/2020 | Hodson et al. |
| 2020/0253521 A1* | 8/2020 | Ivosevic .......... A61B 5/150755 |
| 2020/0261668 A1 | 8/2020 | Hodson et al. |
| 2020/0289808 A1 | 9/2020 | Moeckly et al. |
| 2020/0297945 A1 | 9/2020 | Cottenden et al. |
| 2020/0353155 A1 | 11/2020 | Bernstein et al. |
| 2021/0022681 A1 | 1/2021 | Chickering, III et al. |
| 2021/0030975 A1 | 2/2021 | Burton et al. |
| 2021/0059588 A1 | 3/2021 | Welch et al. |
| 2021/0100487 A1 | 4/2021 | Cho et al. |
| 2021/0121110 A1 | 4/2021 | Kelly et al. |
| 2021/0170153 A1 | 6/2021 | Ross et al. |
| 2021/0196567 A1 | 7/2021 | Baker et al. |
| 2021/0228124 A1 | 7/2021 | Gonzalez-Zugasti et al. |
| 2021/0259599 A1 | 8/2021 | Haghgooie et al. |
| 2021/0298679 A1 | 9/2021 | Pierart |
| 2021/0330227 A1 | 10/2021 | Levinson et al. |
| 2021/0369150 A1 | 12/2021 | Bernstein et al. |
| 2021/0378567 A1* | 12/2021 | Weidemaier ..... A61B 5/150755 |
| 2022/0031211 A1 | 2/2022 | Yakhnich et al. |
| 2022/0058895 A1 | 2/2022 | Han |
| 2022/0062607 A1 | 3/2022 | Davis et al. |
| 2022/0071534 A9 | 3/2022 | Gonzalez-Zugasti et al. |
| 2022/0133192 A1 | 5/2022 | Brancazio |
| 2022/0134072 A1 | 5/2022 | Kosel et al. |
| 2022/0215921 A1 | 7/2022 | Levinson et al. |
| 2022/0218251 A1 | 7/2022 | Jackson et al. |
| 2022/0249818 A1 | 8/2022 | Chickering, III et al. |
| 2022/0257158 A1 | 8/2022 | Haghgooie et al. |
| 2022/0287642 A1 | 9/2022 | Chickering, III et al. |
| 2022/0313128 A1 | 10/2022 | Bernstein et al. |

(56) References Cited

U.S. PATENT DOCUMENTS

2022/0361784 A1 11/2022 Jordan et al.
2023/0109881 A1 4/2023 Nawana et al.

FOREIGN PATENT DOCUMENTS

| | | | |
|---|---|---|---|
| CN | 101296752 | A | 10/2008 |
| EP | 0931507 | A1 | 7/1999 |
| EP | 1769735 | A1 | 4/2007 |
| EP | 2493537 | A2 | 9/2012 |
| EP | 3513833 | A1 | 7/2019 |
| EP | 3490453 | B1 | 12/2021 |
| EP | 3962363 | A1 | 3/2022 |
| ES | 2550668 | T3 | 11/2015 |
| ES | 2565805 | T3 | 4/2016 |
| GB | 1492500 | A | 11/1977 |
| JP | 2004042164 | A | 1/2004 |
| KR | 101857300 | B1 | 5/2018 |
| WO | 9311747 | A1 | 6/1993 |
| WO | 9929296 | A1 | 6/1999 |
| WO | 0078286 | A1 | 12/2000 |
| WO | 0210037 | A1 | 2/2002 |
| WO | 0226217 | A2 | 4/2002 |
| WO | 0232785 | A1 | 4/2002 |
| WO | 02083205 | A1 | 10/2002 |
| WO | 02083231 | A1 | 10/2002 |
| WO | 02083232 | A1 | 10/2002 |
| WO | 03002069 | A2 | 1/2003 |
| WO | 03030880 | A1 | 4/2003 |
| WO | 03035510 | A1 | 5/2003 |
| WO | 03066126 | A2 | 8/2003 |
| WO | 03084597 | A1 | 10/2003 |
| WO | 03086349 | A1 | 10/2003 |
| WO | 03086350 | A1 | 10/2003 |
| WO | 03089036 | A1 | 10/2003 |
| WO | 2004009172 | A1 | 1/2004 |
| WO | 2004022133 | A2 | 3/2004 |
| WO | 2004022142 | A1 | 3/2004 |
| WO | 2004032990 | A2 | 4/2004 |
| WO | 2004039429 | A2 | 5/2004 |
| WO | 2004062715 | A3 | 10/2004 |
| WO | 2004098576 | A1 | 11/2004 |
| WO | 2005006535 | A1 | 1/2005 |
| WO | 2005026236 | A1 | 3/2005 |
| WO | 2005060441 | A2 | 7/2005 |
| WO | 2005014078 | A3 | 10/2005 |
| WO | 2005084534 | | 10/2005 |
| WO | 2005123173 | A1 | 12/2005 |
| WO | 2006016364 | A2 | 2/2006 |
| WO | 2006055795 | A1 | 5/2006 |
| WO | 2006055799 | A1 | 5/2006 |
| WO | 2006055802 | A1 | 5/2006 |
| WO | 2006055844 | A2 | 5/2006 |
| WO | 2006062848 | A1 | 6/2006 |
| WO | 2006062974 | A2 | 6/2006 |
| WO | 2006108185 | A1 | 10/2006 |
| WO | 2006115663 | A2 | 11/2006 |
| WO | 2006135696 | A2 | 12/2006 |
| WO | 2007002521 | A2 | 1/2007 |
| WO | 2007002522 | A1 | 1/2007 |
| WO | 2007002523 | A2 | 1/2007 |
| WO | 2007023276 | A1 | 3/2007 |
| WO | 2007061781 | A1 | 5/2007 |
| WO | 2007064486 | A1 | 6/2007 |
| WO | 2007103712 | A2 | 9/2007 |
| WO | 2006110723 | A3 | 11/2007 |
| WO | 2007124411 | A1 | 11/2007 |
| WO | 2008014161 | A1 | 1/2008 |
| WO | 2007124406 | A3 | 2/2008 |
| WO | 2008008845 | A3 | 4/2008 |
| WO | 2008049107 | A1 | 4/2008 |
| WO | 2008091602 | A3 | 9/2008 |
| WO | 2008121459 | A1 | 10/2008 |
| WO | 2008149333 | A9 | 1/2009 |
| WO | 2009037192 | A1 | 3/2009 |
| WO | 2009046173 | A3 | 5/2009 |
| WO | 2009061895 | A2 | 5/2009 |
| WO | 2009061907 | A2 | 5/2009 |
| WO | 2009056981 | A3 | 8/2009 |
| WO | 2009126653 | A1 | 10/2009 |
| WO | 2009158300 | A1 | 12/2009 |
| WO | 2009142852 | A3 | 1/2010 |
| WO | 2010049048 | A1 | 5/2010 |
| WO | 2010059605 | A2 | 5/2010 |
| WO | 2010062908 | A1 | 6/2010 |
| WO | 2010071262 | A1 | 6/2010 |
| WO | 2010098339 | A1 | 9/2010 |
| WO | 2010101621 | A1 | 9/2010 |
| WO | 2010101625 | A2 | 9/2010 |
| WO | 2010101626 | A1 | 9/2010 |
| WO | 2010101620 | A3 | 11/2010 |
| WO | 2010129783 | A1 | 11/2010 |
| WO | 2010002613 | A3 | 12/2010 |
| WO | 2010110916 | A3 | 12/2010 |
| WO | 2010151329 | A1 | 12/2010 |
| WO | 2010117602 | A3 | 3/2011 |
| WO | 2011016615 | A3 | 4/2011 |
| WO | 2011053787 | A2 | 5/2011 |
| WO | 2011053788 | A2 | 5/2011 |
| WO | 2011053796 | A2 | 5/2011 |
| WO | 2011063067 | A1 | 5/2011 |
| WO | 2011065972 | A2 | 6/2011 |
| WO | 2011071788 | A1 | 6/2011 |
| WO | 2011075099 | A1 | 6/2011 |
| WO | 2011075103 | A1 | 6/2011 |
| WO | 2011075104 | A1 | 6/2011 |
| WO | 2011075105 | A1 | 6/2011 |
| WO | 2011075569 | A1 | 6/2011 |
| WO | 2011084316 | A2 | 7/2011 |
| WO | 2011088211 | A2 | 7/2011 |
| WO | 2011094573 | A1 | 8/2011 |
| WO | 2011014514 | | 9/2011 |
| WO | 2011088214 | A3 | 9/2011 |
| WO | 2011113114 | A1 | 9/2011 |
| WO | 2011116388 | A1 | 9/2011 |
| WO | 2011084951 | A3 | 11/2011 |
| WO | 2011088211 | A3 | 12/2011 |
| WO | 2011150144 | A2 | 12/2011 |
| WO | 2011163347 | A2 | 12/2011 |
| WO | 2012030316 | A1 | 3/2012 |
| WO | 2012018486 | A3 | 4/2012 |
| WO | 2012045561 | A1 | 4/2012 |
| WO | 2012048388 | A1 | 4/2012 |
| WO | 2012049155 | A1 | 4/2012 |
| WO | 2012054592 | A1 | 4/2012 |
| WO | 2012021792 | A3 | 5/2012 |
| WO | 2012028675 | A3 | 5/2012 |
| WO | 2012061556 | A1 | 5/2012 |
| WO | 2012089627 | A1 | 7/2012 |
| WO | 2012122162 | A1 | 9/2012 |
| WO | 2012145665 | A2 | 10/2012 |
| WO | 2012117302 | A3 | 11/2012 |
| WO | 2012149126 | A1 | 11/2012 |
| WO | 2012149143 | A1 | 11/2012 |
| WO | 2012154362 | | 12/2012 |
| WO | 2012173971 | A1 | 12/2012 |
| WO | 2012149134 | | 1/2013 |
| WO | 2012149155 | A9 | 3/2013 |
| WO | 2013036602 | A1 | 3/2013 |
| WO | 2013050701 | A1 | 4/2013 |
| WO | 2013055638 | A1 | 4/2013 |
| WO | 2013055641 | A1 | 4/2013 |
| WO | 2013059409 | A1 | 4/2013 |
| WO | 2013082418 | A1 | 6/2013 |
| WO | 2013082427 | A1 | 6/2013 |
| WO | 2013090353 | A1 | 6/2013 |
| WO | 2013096026 | A1 | 6/2013 |
| WO | 2013096027 | A1 | 6/2013 |
| WO | 2013112877 | A1 | 8/2013 |
| WO | 2013120665 | A1 | 8/2013 |
| WO | 2013136176 | A1 | 9/2013 |
| WO | 2013136185 | A3 | 11/2013 |
| WO | 2013165715 | A1 | 11/2013 |
| WO | 2013188609 | A1 | 12/2013 |
| WO | 2014004462 | A1 | 1/2014 |

(56) References Cited

FOREIGN PATENT DOCUMENTS

| | | |
|---|---|---|
| WO | 2014018558 A1 | 1/2014 |
| WO | 2014039367 A1 | 3/2014 |
| WO | 2014052263 A1 | 4/2014 |
| WO | 2014058746 A1 | 4/2014 |
| WO | 2014059104 A1 | 4/2014 |
| WO | 2014078545 A1 | 5/2014 |
| WO | 2014081746 A1 | 5/2014 |
| WO | 2014099404 A1 | 6/2014 |
| WO | 2014105458 A1 | 7/2014 |
| WO | 2014110016 A1 | 7/2014 |
| WO | 2014096001 A3 | 8/2014 |
| WO | 2014132239 A1 | 9/2014 |
| WO | 2014132240 A1 | 9/2014 |
| WO | 2014153447 A2 | 9/2014 |
| WO | 2014160804 A2 | 10/2014 |
| WO | 2014193725 A1 | 12/2014 |
| WO | 2014193727 A1 | 12/2014 |
| WO | 2014193729 A1 | 12/2014 |
| WO | 2014204951 A1 | 12/2014 |
| WO | 2014186263 A3 | 1/2015 |
| WO | 2015006292 A1 | 1/2015 |
| WO | 2015009523 A1 | 1/2015 |
| WO | 2015009530 A1 | 1/2015 |
| WO | 2015009531 A1 | 1/2015 |
| WO | 2015031552 A1 | 3/2015 |
| WO | 2015034709 A1 | 3/2015 |
| WO | 2015038556 A1 | 3/2015 |
| WO | 2015023649 A3 | 4/2015 |
| WO | 2015072924 A1 | 5/2015 |
| WO | 2015116625 A1 | 8/2015 |
| WO | 2015153570 A1 | 10/2015 |
| WO | 2015153624 A1 | 10/2015 |
| WO | 2015168210 A1 | 11/2015 |
| WO | 2015168215 A1 | 11/2015 |
| WO | 2015168217 A1 | 11/2015 |
| WO | 2015179511 A1 | 11/2015 |
| WO | 2016018892 A1 | 2/2016 |
| WO | 2016081843 A1 | 5/2016 |
| WO | 2016099986 A1 | 6/2016 |
| WO | 2016099986 A2 | 6/2016 |
| WO | 2016100708 A1 | 6/2016 |
| WO | 2016109336 A1 | 7/2016 |
| WO | 2016109339 A1 | 7/2016 |
| WO | 2016109342 A1 | 7/2016 |
| WO | 2016118459 A1 | 7/2016 |
| WO | 2016122915 A1 | 8/2016 |
| WO | 2016132368 A1 | 8/2016 |
| WO | 2016137853 A1 | 9/2016 |
| WO | 2016164508 A1 | 10/2016 |
| WO | 2015168219 | 12/2016 |
| WO | 2017044887 A1 | 3/2017 |
| WO | 2017062727 A1 | 4/2017 |
| WO | 2017062922 A1 | 4/2017 |
| WO | 2017075018 A1 | 5/2017 |
| WO | 2017075586 A1 | 5/2017 |
| WO | 2017087355 A1 | 5/2017 |
| WO | 2017087368 A1 | 5/2017 |
| WO | 2017112400 A1 | 6/2017 |
| WO | 2017112451 A1 | 6/2017 |
| WO | 2017112452 A1 | 6/2017 |
| WO | 2017112748 A1 | 6/2017 |
| WO | 2017113011 A1 | 7/2017 |
| WO | 2017139084 A1 | 8/2017 |
| WO | 2017112476 A3 | 9/2017 |
| WO | 2017176693 A1 | 10/2017 |
| WO | 2017176704 A1 | 10/2017 |
| WO | 2017193076 A1 | 11/2017 |
| WO | 2018022535 A1 | 2/2018 |
| WO | 2018048786 A1 | 3/2018 |
| WO | 2018048790 A1 | 3/2018 |
| WO | 2018048795 A1 | 3/2018 |
| WO | 2018048797 A1 | 3/2018 |
| WO | 2018057760 A1 | 3/2018 |
| WO | 2018128976 A1 | 7/2018 |
| WO | 2018132515 A1 | 7/2018 |
| WO | 2018204217 A1 | 11/2018 |
| WO | 2018213244 A1 | 11/2018 |
| WO | 2019067567 A1 | 4/2019 |
| WO | 2019121324 A1 | 6/2019 |
| WO | 2020025823 A1 | 2/2020 |
| WO | 2020102281 A1 | 5/2020 |
| WO | 2020223710 A1 | 11/2020 |
| WO | 2021007344 A1 | 1/2021 |
| WO | 2021041881 A1 | 3/2021 |
| WO | 2021076846 A1 | 4/2021 |
| WO | 2021121638 A1 | 6/2021 |
| WO | 2021198768 A2 | 10/2021 |
| WO | 2021222066 A1 | 11/2021 |
| WO | 2021222805 A1 | 11/2021 |
| WO | 2022064055 A1 | 3/2022 |

OTHER PUBLICATIONS

International Search Report and Written Opinion for PCT/US2022/048913 dated Feb. 21, 2023.
International Search Report and Written Opinion for PCT/US22/029829 dated Nov. 23, 2022.
International Search Report and Written Opinion, PCT/US2022/048913, dated Feb. 21, 2023, 16 pages.
English machine translation of JP-2004024164-A, patents.google.com, 8 pages.
International Search Report and Written Opinion, PCT/US2022/024607, dated Aug. 4, 2022, 17 pages.
International Search Report and Written Opinion, PCT/US2022/029829, dated Nov. 23, 2022, 16 pages.
International Search Report and Written Opinion, PCT/US2022/046384, dated Jan. 5, 2023, 12 pages.
Taiwan Office Action, TW111142334, dated May 18, 2023 (with English translation), 29 pages.

* cited by examiner

DERMAL PATCH FOR COLLECTING A PHYSIOLOGICAL SAMPLE

RELATED APPLICATIONS

The present application a continuation of a granted U.S. patent entitled Dermal Patch for Collecting a Physiological Sample having U.S. Pat. No. 11,510,602 filed on Nov. 8, 2021 which is incorporated by reference herein in its entirety.

TECHNICAL FIELD

The following relates to dermal patches and more particularly to dermal patches for collection and/or analysis of a physiological sample.

BACKGROUND

Biomarkers are increasingly employed for diagnosis of various disease conditions as well as for assessing treatment protocols. Unfortunately, the invasive nature of drawing a blood sample from a subject can cause discomfort and may lead to less cooperation from the subject, especially children, and hence render obtaining the blood sample difficult.

Some recently developed dermal patches allow for the detection of target biomarkers, but typically suffer from a number of shortcomings, such as low sensitivity and/or specificity. Some dermal patches allow a user to collect a physiological sample in order to send the collected sample to a laboratory for analysis.

There is still a need for dermal patches that can allow facile collection of a physiological sample (e.g., a blood sample) in a variety of environments for storage and/or for in-situ analysis.

SUMMARY

Aspects of the present disclosure address the above-referenced problems and/or others.

In one aspect, a dermal patch for collecting, and optionally analyzing, a physiological sample includes a housing (herein also referred to as a "frame") that includes a sample collection chamber, a sample fluidic channel and a pin within a receptacle of the housing. The sample fluidic channel is configured to direct a physiological sample drawn from a subject to the collection chamber. The pin is removably positioned within the receptacle and is configured to be moved (e.g., it can be pulled by a user) from an undeployed position to a deployed position. The pin is configured to seal the receptacle when in the undeployed position and is further configured to facilitate generation of a negative pressure in the sample fluidic channel when the pin is moved from the undeployed to the deployed position. The physiological sample can include, but is not limited to blood and interstitial fluid.

In some embodiments, the housing also includes an opening that is covered by a septum. When the dermal patch is attached to a subject's skin, the septum may be punctured by a lancet thereby allowing access to the subject's skin, which can be punctured by the lancet via passage through the punctured septum and the opening below the septum to allow drawing a physiological sample for collection and/or analysis. In some embodiments, the septum is formed of a self-healing polymeric material (e.g., Polyisoprene and thermoplastic elastomers ("TPE")), which can create a sealed surface after withdrawal of the lancet such that the physiological sample (e.g., blood and/or interstitial fluid) will be drawn into the collection chamber via passage in the space between the bottom of the septum and the skin, e.g., in a manner discussed in more detail below.

In some embodiments, the dermal patch further includes a processing fluid reservoir (e.g., a processing fluid pouch), such as a fluid pack, that is coupled to the housing, e.g., disposed within the housing. A variety of processing fluids may be stored within the processing fluid pouch. By way of example, and without limitation, the processing fluid may be an anti-coagulant (e.g., heparin or a protease inhibitor), a reagent, and/or a buffer. For example, a plurality of buffer formulations, such as lysing buffers, are known and can be incorporated in various embodiments of a dermal patch according to the present teachings.

In some embodiments, the dermal patch also includes a slider that is slidably coupled to the housing. The slider is moveable between an undeployed position and a deployed position. In the deployed position, the slider causes the release of the processing fluid from the fluid pouch. In some embodiments, the housing may also include a processing fluidic channel that directs the released processing fluid to the collection chamber, e.g., to be mixed and interact with a collected physiological sample, e.g., blood.

In other embodiments, the dermal patch includes a detector (herein also referred to as a sensor) that is in communication with the collection chamber. The detector can generate one or more signals indicative of the presence of a target analyte in a drawn physiological sample or a processed physiological sample. When the processing fluid and the physiological sample enter the collection chamber, they mix and interact to form a processed physiological sample. In some embodiments, the interaction of the drawn physiological sample and the processing fluid can prepare the sample for storage and/or in-situ analysis.

The detector incorporated in a dermal patch according to the present teachings can be used to detect a variety of analytes. Further, in some embodiments, the detector can be a calibrated detector that can not only detect, but also quantify, an analyte of interest, when present in the drawn physiological sample. By way of example and without limitation, the target analyte may include a biomarker including, but not limited to, troponin, brain natriuretic peptide (BnP), myelin basic protein (MBP), ubiquitin carboxyl-terminal hydrolase isoenzyme L1 (UCHL-1), neuron-specific enolase (NSE), glial fibrillary acidic protein (GFAP), S100-B, Cardiac troponin I protein (cTnI), Cardiac troponin T protein (cTnT), C-reactive protein (CRP), B-type natriuretic peptide (BNP), Myeloperoxidase, Creatine kinase MB, Myoglobin, Hemoglobin, or HbA1C. In some embodiments, the target analyte may be a pathogen, e.g., a bacterium or a virus. Further, a variety of detectors can be employed in the practice of the present teachings. Some examples of suitable detectors can include, without limitation, a lateral flow detector, an electrochemical detector, or a graphene-based detector.

In some embodiments, the dermal patch also includes an absorbent element (hereinafter also referred to as absorbent pad) that is disposed in the collection chamber and is configured to absorb at least a portion of the drawn physiological sample. The absorbent element can be used to store the collected physiological sample for analysis. For example, the absorbent element may be removed from the patch and sent to a laboratory for analysis of the collected sample. By way of example and without limitation, the absorbent element can be a filter paper matrix, (e.g., a nitrocellulose strip), microfiber filters, gauze, non-woven sheets, polymers, etc. In other embodiments, the absorbent element may be left in the dermal patch and the dermal patch may be sent to a lab for further analysis. At the lab, a technician may remove the absorbent element form the dermal patch to analyze the physiological sample.

In some embodiments, the dermal patch also includes an adhesive layer for attaching the dermal patch to the subject's skin.

In another aspect, a method for collecting a physiological sample includes applying a dermal patch to a subject's skin, puncturing the subject's skin, drawing the physiological sample, releasing a processing fluid stored within the dermal patch, causing the drawn physiological sample and the released processing fluid to mix (e.g., by directing the drawn physiological sample and the released processing fluid to a collection chamber of the dermal patch). In some embodiments, the sample and the processing fluid mix and interact within the collection chamber to form a processed physiological sample and the method further includes detecting a target analyte within the processed physiological sample with a detector that is in communication with the collection chamber.

In some embodiments, the dermal patch can include multiple fluid reservoirs (e.g., multiple fluid pouches), for example, for storing different processing fluids. The fluid reservoirs can be activated, e.g., concurrently or in any desirable sequence, to release the processing fluid contained therein for use, for example, in an assay performed on the collected physiological sample. For example, the processing fluids can flow through one or more fluidic channels to mix with the sample and/or be delivered to a detector in order to take part in the assay, e.g., through mixing and/or delivery to the detector (e.g., via deposition on a lateral flow assay (LFA) strip and/or other types of detector.

Further understanding of various aspects of the present teachings can be obtained by reference to the following detailed description in conjunction with the associated drawings, which are described briefly below.

BRIEF DESCRIPTION OF THE DRAWINGS

Aspects of the present disclosure may take form in various components and arrangements of components, and in various steps and arrangements of steps. The drawings are only for illustration purposes of preferred embodiments of the present disclosure and are not to be considered as limiting.

Features of embodiments of the present disclosure will be more readily understood from the following detailed description take in conjunction with the accompanying drawings in which.

DETAILED DESCRIPTION

Figure 1:
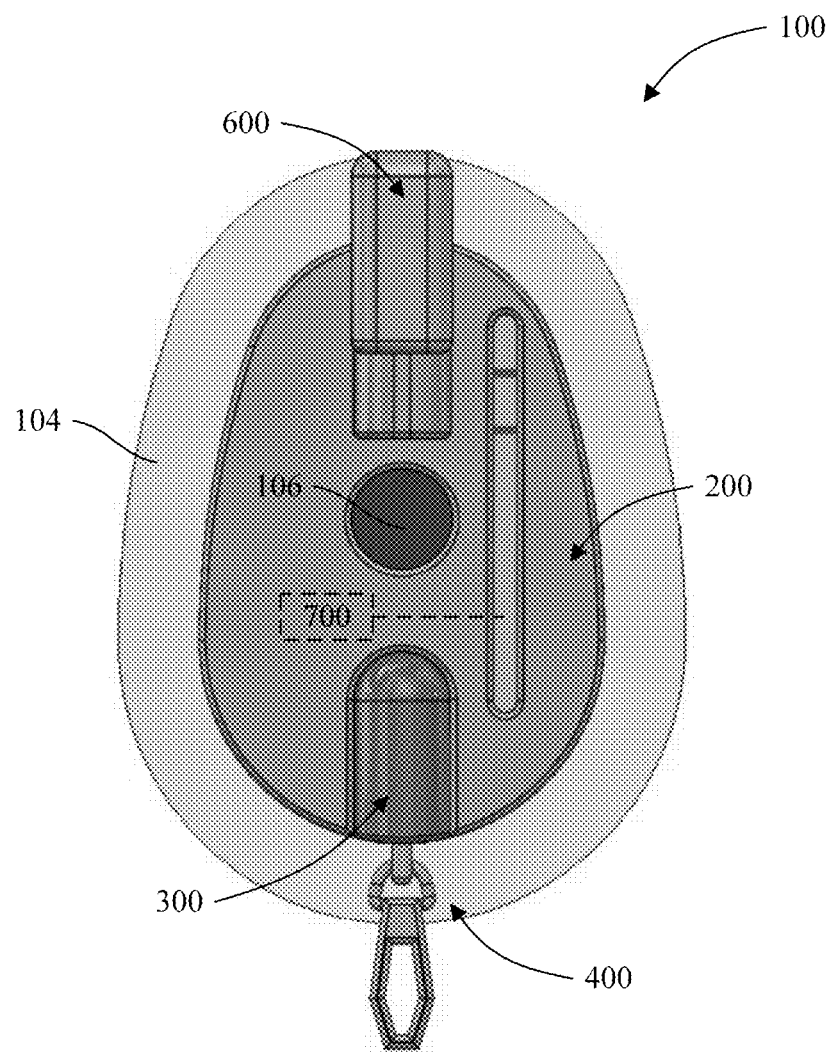
FIG. 1 depicts a dermal patch in accordance with an exemplary embodiment.

The present disclosure generally relates to a dermal patch that may be utilized to collect and store a physiological sample (e.g., blood, interstitial fluid, etc.) and/or analyze a collected physiological sample, e.g., detect an analyte of interest in the collected physiological sample.

In some embodiments, a dermal patch that is used to collect a physiological sample may include a processing fluid (e.g., reagent, buffer, anticoagulant, etc.). The processing fluid may be suitable for preserving the physiological sample and/or preparing the sample for analysis. Providing a dermal patch that includes a processing fluid contained within a reservoir incorporated in the patch allows for the collection and preservation of a physiological sample within the dermal patch. Such a dermal patch can allow for facile collection and analysis of a physiological sample, e.g., in the field, at a medical facility, or even at home.

In other embodiments, a dermal patch that is used to detect a target analyte (e.g., a biomarker) in a physiological sample includes a processing fluid and a detector that can detect a target analyte. The processing fluid may be suitable for amplification of a target analyte (e.g., a primer). Providing a dermal patch that includes a processing fluid and a detector allows for the drawing of a physiological sample and the detection of a target analyte within the dermal patch. Such a dermal patch may allow a user of the dermal patch to detect an analyte in a drawn physiological sample themselves at home.

Various terms are used herein in accordance with their ordinary meanings in the art, unless indicated otherwise. The term "about," as used herein, denotes a deviation of at most 10% relative to a numerical value. The term "substantially," as used herein, refers to a deviation, if any, of at most 10% from a complete state and/or condition. The term "lancet" is used herein to broadly refer to an element that can be used to provide a passageway, or facilitate the production of a passageway, for collecting a physiological sample, such as a blood or an interstitial fluid sample through a patient's skin, e.g., via puncturing the subject's skin. The term "transparent," as used herein, indicates that light can substantially pass through an object (e.g., a window) to allow visualization of a material disposed behind the object. For example, in some embodiments, a transparent object allows the passage of at least 70%, or at least 80%, or at least 90%, of the visible light therethrough. The term "vacuum," as used herein, refers to a pressure less than the atmospheric pressure, and more particularly to a pressure that can facilitate the extraction of a physiological sample from a subject.

Referring now to FIGS. 1-8 a dermal patch 100 is shown in accordance with an exemplary embodiment. The dermal patch 100 includes a top portion 200 and a bottom portion 300 that is coupled to the top portion 200. In some embodiments, the top portion 200 is removably coupled to the bottom portion 300. For example, in this embodiment, the top portion 200 and the bottom portion 300 are formed as two separate components that are removably coupled to one another. In another embodiment, the top portion 200 and the bottom portion 300 form an integral unitary patch. In some embodiments, the top portion 200 may be coupled to the bottom portion 300 via double sided adhesive, laser welding, press fitting or a combination thereof.

The top portion 200 and the bottom portion 300 may be formed using a variety of suitable materials including, but not limited to, polymeric materials, e.g., polyolefins, PET (Polyethylene Terephthalate), polyurethanes, polynorbornenes, polyethers, polyacrylates, polyamides (Polyether block amide also referred to as Pebax®), polysiloxanes, polyether amides, polyether esters, trans-polyisoprenes, polymethyl methacrylates (PMMA), cross-linked trans-polyoctylenes, cross-linked polyethylenes, cross-linked polyisoprenes, cross-linked polycyclooctenes, inorganic-organic hybrid polymers, co-polymer blends with polyethylene and Kraton®, styrene-butadiene co-polymers, urethane-butadiene co-polymers, polycaprolactone or oligo caprolactone co-polymers, polylactic acid (PLLA) or polylactide (PL/DLA) co-polymers, PLLA-polyglycolic acid (PGA) co-polymers, and photocross linkable polymers. In some embodiments, some of the top portion 200 may be formed poly(dimethylsiloxane) (PDMS) to allow visibility of components disposed with the bottom portion 300.

The top portion 200 includes a top surface 202 and an opposed bottom surface 204 and the bottom portion 300 includes a top surface 302 and an opposed bottom surface 304. When the top portion 200 is coupled to the bottom portion 300, the bottom surface 204 of the top portion 200 contacts the top surface 302 of the bottom portion 300. The top portion 200 and the bottom portion 300 define an aperture 102 that extends through the top and the bottom portions 200/300. Stated another way, the aperture 102 extends between the top surface 202 of top portion 200 and the bottom surface 304 of the bottom portion 300. As will be discussed in further detail below, the bottom portion 300 includes a plurality of channels. In order to seal these channels, a film (e.g., a polymeric film) may be applied to the surface 302.

The dermal patch 100 also includes an adhesive layer 104 disposed on the bottom surface 304 of the bottom portion 300 and surrounds the aperture 102 such that the adhesive layer 104 does not cover the aperture 102. In use the dermal patch 100 may be attached to a subject's skin via the adhesive layer 104. The adhesive layer 104 may be laminated to or heat/laser/adhesively bonded to the bottom surface 304. The dermal patch 100 may be attached anywhere on the subject's skin capable of supporting the dermal patch 100 (e.g., on a leg, arm, etc. of the subject). In some embodiments, a removable protective liner (not shown in the figures) covers the adhesive surface of the adhesive layer 104 and may be removed to expose the adhesive surface for attachment onto the subject's skin.

The dermal patch 100 further includes a septum 106, which extends longitudinally along the top surface 302 of the bottom portion 300 so as to cover at least a portion of the aperture 102. The septum 106 may be formed of a polymeric material, such as polyisoprene, and may be configured such that it can be punctured via a lancet, as discussed in more detail below. In some embodiments, the thickness of the septum 106 can be in a range of about 0.015" to about 0.040" (e.g., 0.020").

Once the dermal patch 100 is attached to a subject's skin, a user (e.g., the subject wearing the dermal patch 100, a physician, a caretaker, etc.) may use a lancet 108 to puncture the septum 106 and further extend the lancet through the aperture 102 to puncture the subject's skin, thereby providing access for drawing a physiological sample (e.g., blood, interstitial fluid, etc.) from the subject. In some embodiments, the septum 106 may be self-sealing. In these embodiments, after the lancet 108 has been retracted from the septum 106, the septum 106 seals and creates a sealed surface such that the drawn physiological sample can flow within a space between a bottom surface of the septum 106 and the skin of the subject (e.g., for collection in a collection chamber of the dermal patch 100).

The bottom portion 300 further includes a pin receptacle 306 that is shaped and dimensioned to receive a pin 400 and retain the pin 400 in place via an interference fit. The base portion also includes a vacuum channel 308 that is in fluid communication with the pin receptacle 306. As will be discussed in further detail herein, the distal portion of the pin 400 can include a plurality of grooves in which O-rings can be positioned such that when the pin 400 is engaged within the pin receptable 306 (e.g., when the pin 400 is in an undeployed position), the pin 400 forms an airtight seal within the pin receptacle 306. As will be discussed in further detail herein, the distal portion of the pin 400 can include a plurality of grooves in which sealing elements (O-rings in this embodiment) can be positioned such that when the pin 400 is engaged within the pin receptable 306 (e.g., when the pin 400 is in an undeployed position), the pin 400 forms an airtight seal within the pin receptacle 306 to allow application of a positive or a negative pressure as needed, as described in more detail below.

Figure 2:
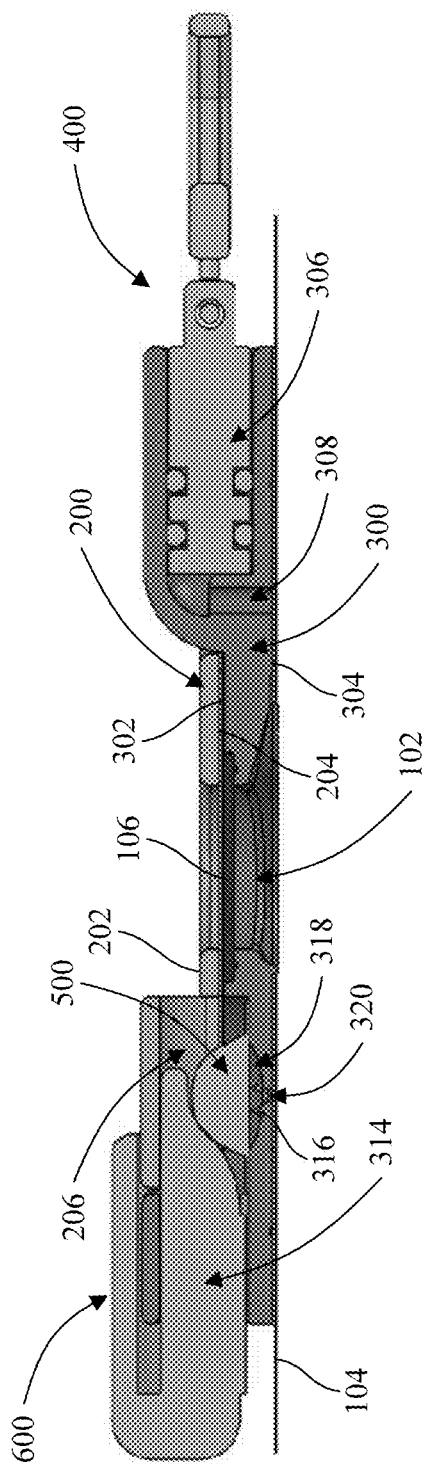
FIG. 2 is a cross sectional view of a dermal patch in accordance with an exemplary embodiment.
Figure 3:
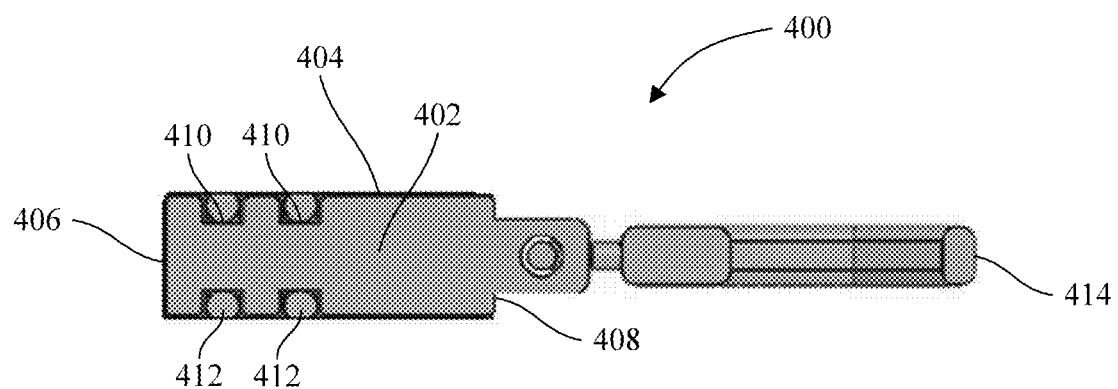
FIG. 3 is a cross sectional view of a pin that can be activated to generate a negative pressure in one or more channels of a dermal patch to facilitate the drawing of a physiological sample in accordance with an exemplary embodiment.
Figure 4:
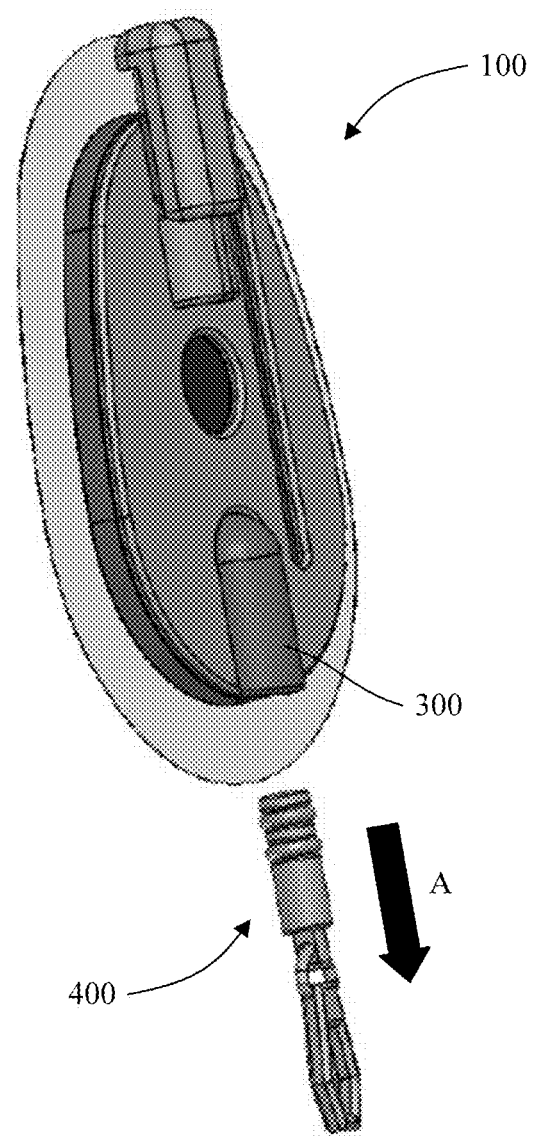
FIG. 4 schematically depicts the pin of a dermal patch shown in FIG. 3 being transitioned from an undeployed position to a deployed position via removal from a receptacle on the dermal patch housing the pin.

More specifically, referring now to FIG. 3 the pin 400 includes a cylindrical barrel 402, which includes an outer surface 404 that extends between a proximal end 406 and a distal end 408 of the barrel 402. The outer surface 404 defines a plurality of grooves 410 that extend circumferentially about the barrel 402. The grooves 410 are shaped and dimensioned to retain elastomeric O-rings 412. When the barrel 402 is positioned within the pin receptacle 306 (hereinafter referred to as "an undeployed position"), the elastomeric O-rings 412 contact the surface of the pin receptacle 306 to create an airtight seal between the barrel 402 and the inner surface of the pin receptacle 306. While FIGS. 2 and 3 depict the pin 400 as including the O-rings 412, in other embodiments, the pin 400 may include a single elastomeric piece, an overmold with a solid substrate and elastomeric O-rings or flaps that create the seal between the pin 400 and the surface of the pin receptacle 306.

The pin 400 further includes a handle 414 that is connected to the barrel 402 and extends external to the pin receptacle 306 when the barrel 402 is within the pin receptacle 306 and hence can be employed to remove the barrel 402 from the pin receptacle 306 and generate a vacuum for drawing a physiological sample. In some embodiments, for example after the pin has been removed and air has entered into the pin receptacle 306, the pin can be reinserted into the pin receptacle 306 thereby creating a positive pressure to further facilitate fluidic flow.

Stated another way, when the pin 400 is in the undeployed position, the handle 414 is accessible to a user. In use, subsequent to puncturing the skin of a subject (e.g., by using the lancet 108 in a manner discussed above) a user can pull the handle 414, e.g., using a draw string (not shown) attached to the handle 414, in the direction of arrow A (FIG. 4), to remove the barrel 402 from the pin receptacle 306 (hereinafter referred to as a "deployed position"). Removing the barrel 402 from the pin receptacle 306 creates a vacuum within a vacuum channel 308, which is in fluid communication with a physiological sample channel 310 (or simply a "sample channel"). Thus, removing the pin barrel 402 from the pin receptacle 306 results in the generation of a vacuum within the sample channel 310, thereby facilitating the drawing of a physiological sample from the subject and directing the drawn physiological sample into a collection chamber 312. More specifically, the sample channel 310 is in fluid communication with the aperture 102 and the collection chamber 312, which is in turn in fluid communication with the vacuum channel 308, and the sample channel 310. As such, the sample channel 310 is in fluid communication with the vacuum channel 308 and hence can deliver the drawn physiological sample to the collection chamber 312 upon creation of a vacuum within the vacuum channel 308.

In some embodiments, after the pin 400 has been removed from the pin receptacle 306 to generate a vacuum for drawing a physiological sample, the pin 400 may be placed back into the pin receptacle 306 for storage. When placed back into the pin receptacle 306 the pin 400 displaces air within the pin receptacle 306 thereby creating positive pressure within the vacuum channel 308.

In this embodiment, the dermal patch 100 further includes a reservoir in the form of a fluid pouch 500 formed of a frangible membrane that provides a sealed enclosure for storing a processing fluid for processing/stabilizing or otherwise treating a physiological sample drawn from the subject. Further, the dermal patch 100 includes an actuator in the form of a slider 600 that can be actuated to release the processing fluid from the fluid pouch 500. While FIG. 2 depicts the processing fluid as being stored in the fluid pouch 500, in other embodiments, the processing fluid may be stored in the dermal patch 100 by other means. For example, the processing fluid may be directly stored in a reservoir molded into the bottom portion 300.

In particular, referring to FIG. 2, the top portion 200 and the bottom portion 300 include channels 206 and 314 positioned in tandem and shaped and dimensioned to receive different portions of a slider 600 so as to retain the slider 600 in engagement with the rest of the dermal patch 100. Stated another way, the two channels cooperatively provide a receptable for receiving the slider 600. FIG. 1 shows the slider 600 in an undeployed position. As discussed below, the slider 600 can be moved from the undeployed position to a deployed position to cause the release of a processing liquid from a reservoir provided in the dermal patch 100.

Figure 5:
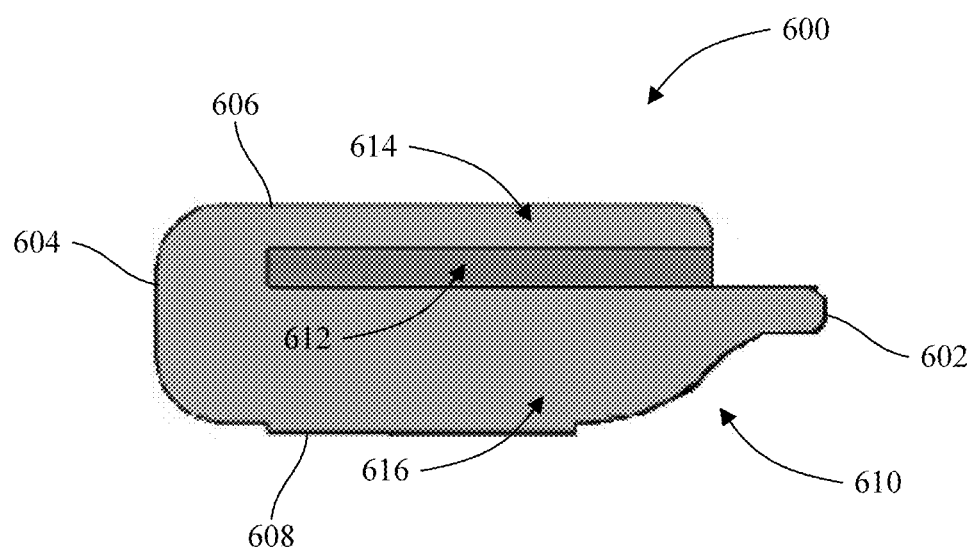
FIG. 5 is a cross sectional view of a slider of a dermal patch in accordance with an exemplary embodiment.
Figure 6:
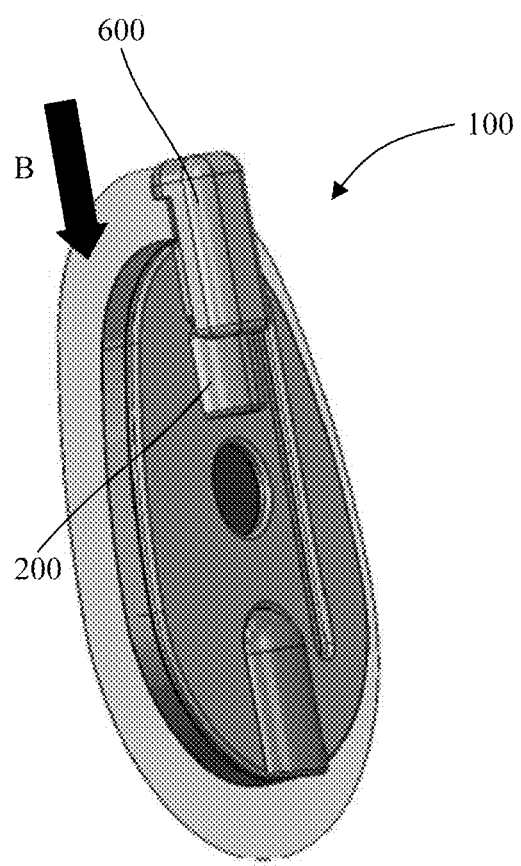
FIG. 6 depicts a slider of a dermal patch in an undeployed position in accordance with an exemplary embodiment.
Figure 7:
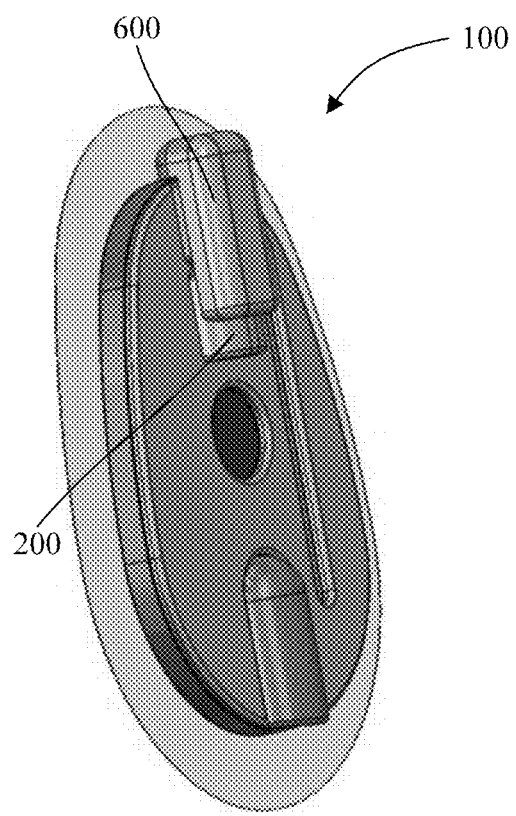
FIG. 7 depicts a slider of a dermal patch in a deployed position in accordance with an exemplary embodiment.

More specifically, with reference to FIG. 5, the slider 600 extends horizontally between a proximal end 602 and a distal end 604 and extends vertically between a top surface 606 and a bottom surface 608. The bottom surface 608 includes a concave portion 610 that is in contact with a processing fluid pouch 500. In this embodiment the curvature of the concave portion 610 substantially matches the convex curvature of the frangible membrane of the fluid pouch 500.

The slider 600 includes a channel 612 that divides the slider 600 into a top portion 614 and a bottom portion 616. The channel 612 can engage with top raised ledges of the channels 314 and 206 provided in the top portion 200 and the bottom portion 300 of the dermal patch 100, respectively, such that the top portion 614 of the slider 600 is accessible to a user while the bottom portion 616 is within the dermal patch 100.

The slider 600 is moveable between an undeployed position (FIGS. 1 and 6) and a deployed position (FIG. 7) by moving the slider 600 in the direction of arrow B (FIG. 6) such that the proximal end 602 of the slider 600 moves further into the channel 206 and the concave portion 610 of the slider 600 presses against the frangible membrane of the processing fluid pouch 500 into a puncture element 316 provided in a well 318 that is positioned below the fluid pouch 500, thereby rupturing the frangible membrane of the processing fluid pouch 500 and releasing the processing fluid stored therein. In some embodiments, rather than employing a frangible membrane, a flexible membrane can be used that does not rupture under applied pressure sufficient to cause the release of at least a portion of a liquid stored in the reservoir, e.g., via a one-way valve positioned in the bottom of the reservoir. The released processing fluid enters the well 318 and flows into a processing fluid channel 320 provided in the base portion. The processing fluid channel 320 provides a passageway for carrying the processing fluid to the collection chamber 312.

A variety of processing liquids (e.g., reagents, buffers, anticoagulants (e.g., ethylenediaminetetraacetic acid (EDTA)), primers, etc.) can be stored within the sealed enclosure of the processing fluid pouch 500. In some embodiments, the processing fluid is suitable for preserving a physiological sample including, but not limited to, an anti-coagulant (e.g., heparin, a protease inhibitor, etc.). In other embodiments, the processing fluid is suitable for isothermal amplification of a target analyte, including but not limited to, a primer.

When the processing fluid and the physiological sample enter collection chamber 312, the processing fluid mixes and interacts with the physiological sample to form a processed physiological sample. In some embodiments, a physiological sample within the collection chamber 312 can be captured using an absorbent element (e.g., a nitrocellulose strip, a microfiber filter, gauze, a non-woven sheet, a polymer, etc.). In such embodiments, the absorbent element can be removed from the collection chamber 312 and be utilized, for example, for analysis of the collected physiological sample. In some embodiments, collected physiological sample can be subjected to genetic analysis (e.g., to detected a genetic marker indicative of susceptibility of a subject to a particular disease).

In some embodiments, a detector 110 may be positioned within the collection chamber 312 to receive at least a portion of the collected physiological sample and provide analysis of the sample, e.g., to detect one or more analytes of interest within the sample. Further, in some embodiments, a dermal patch according to the present teachings may include two or more collection chambers 312 into each of which a portion of a drawn physiological sample is directed. In such embodiments, at least one of the collection chambers 312 may include a detector 110 for analysis of the drawn physiological sample and at least another one of the collection chambers 312 may be utilized for collection of a sample to be analyzed external to the dermal patch. In some embodiments in which the dermal patch 100 includes a plurality of collection chambers 312, the dermal patch 100 may include a plurality of detectors 110 each in communication with at least one of the collection chambers 312. For example, the dermal patch 100 may include a first, a second, and a third collection chamber 312. In this embodiment, the dermal patch may include a first detector 110 in communication with the first collection chamber 312, a second detector 110 in communication with the second collection chamber 312, and a third detector 110 in communication with the third collection chamber 312.

Figure 8:
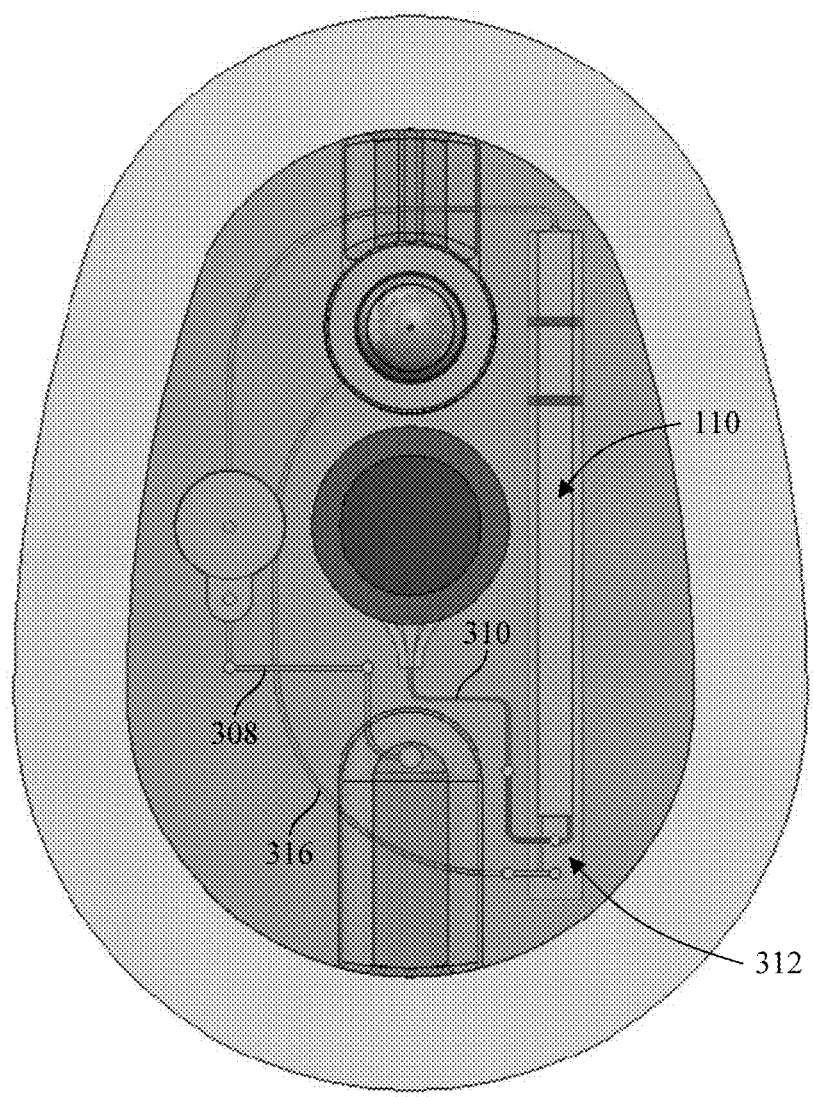
FIG. 8 diagrammatically illustrates a dermal patch in accordance with an exemplary embodiment.

In one embodiment, as depicted in FIG. 8, the detector 110 is positioned within the collection chamber 312. The detector 110 is configured to detect a target analyte within the processed physiological sample. In some embodiments, the detector 110 may detect a target analyte when the concentration of the target analyte within the processed sample is equal to or greater than a threshold (e.g., a limit-of detection (LOD)).

The detector 110 may be any detector capable of detecting a target analyte (e.g., a graphene-based detector, a chemical detector, a lateral flow detector, a DNA sequencing detector, an RNA sequencing detector, etc.). In some embodiments, the detector 110 may be capable of generating a signal indicative of presence of the target analyte in the drawn physiological sample. In some embodiments, the detector 110 may be calibrated to allow quantification of a target analyte, when present in a drawn physiological sample. Furthermore, the detector 110 may be a passive detector or an active detector and may provide chromatographic or "photo-visual," or digital readouts (e.g., a colorimetric detector, an immunoassay detector including lateral flow detectors, isothermal amplification detection systems, etc.). In some embodiments in which a colorimetric detector is employed, at least a portion of the dermal patch 100 may include a transparent window to allow the visualization of the detector 110.

In other embodiments, other suitable means for interrogating the processed physiological sample may be employed. By way of example, in some cases, the interrogation of a processed physiological sample may be achieved without the need for direct contact between a detector 110 and the sample (e.g., optical techniques, such as fluorescent and/or Raman techniques).

In some embodiments, the target analyte may be a pathogen (e.g., a virus, a bacterium, etc.). In these embodiments, the detector 110 may be configured to detect such a pathogen via the detection of a protein and/or a genetic material thereof (e.g., segments of its DNA and/or RNA). In other embodiments, the detector 110 may be a lateral flow detector that may be employed to detect a hormone. In other embodiments, the target analyte may be a biomarker (e.g., a biomarker that may be indicative of a disease condition (e.g., organ damage)). In these embodiments, the biomarker may be indicative of a traumatic brain injury (TBI), including a mild TBI. Some examples of such biomarkers include, but are not limited to, myelin basic protein (MBP), ubiquitin carboxyl-terminal hydrolase isoenzyme L1 (UCHL-1), neuron-specific enolase (NSE), glial fibrillary acidic protein (GFAP), and S100-B.

In other embodiments, the detector 110 may be configured to detect other biomarkers, such as troponin and brain natriuretic peptide (BnP). Other examples include, but are not limited to, Cardiac troponin I protein (cTnI), Cardiac troponin T protein (cTnT), C-reactive protein (CRP), B-type natriuretic peptide (BNP), Myeloperoxidase, Creatine kinase MB, Myoglobin, Hemoglobin, and HbA1C.

In some embodiments, detector 110 may be configured to generate signals indicative of levels of UCHL-1 and GFAP. These proteins are released from the brain into blood within 12 hours of head injury. The levels of these two proteins measured by the detector 110 according to the present disclosure after a mild TBI may help identify those patients that may have intracranial lesions.

In other embodiments, a biomarker detected by the detector may include biomarkers associated with an immune response (i.e., CD4) and other biomarkers associated with specific diseases/conditions (i.e., biomarkers associated with HIV, Malaria, Syphilis, pregnancy, etc.) In general, a dermal patch according to the present teachings can be configured, e.g., using a suitable detector, to detect any blood-based biomarker of interest in a blood sample drawn from a subject, such as those disclosed herein.

In one embodiment, a target analyte may be detected by the detector 110 when the detector 110 is a graphene-based detector that includes a graphene layer that is functionalized with a moiety (e.g., an antibody, an aptamer, an oligonucleotide, etc.) that exhibits specific binding to that target analyte (e.g., a protein, a DNA segment) such that upon binding of the target analyte to that moiety an electrical property of the underlying graphene layer changes, thus indicating the presence of the target analyte in the sample. By way of example, the detection of a target analyte may be achieved by using a graphene-based detector and/or an electrochemical detector that is functionalized with a probe, such as an antibody and/or aptamer, which exhibits specific binding to that target analyte, though other sensing technologies may also be utilized.

In another embodiment, the detector 110 may be an electrochemical detector that functions in a faradaic or non-faradaic mode to detect a target analyte of interest. For example, such an electrochemical detector may include a working electrode, a reference electrode, and a counter electrode. By way of example, in some embodiments, the reference electrode may be functionalized with a moiety that exhibits specific binding to a target analyte such that upon binding of that target analyte, when present in the sample, to the moiety, a change in the current through the circuit may be detected.

In some embodiments, at least one serum-separation element may be associated with the detector 110 for receiving blood and separating a serum/plasma component of the blood for introduction into the detector 110.

The serum-separating element may include a fibrous element that is configured to capture one or more cellular components of a drawn blood sample so as to separate a plasma/serum component of the blood for analysis. In some embodiments, the serum-separating element can be a nitrocellulose strip. The use of such a fibrous element, and in particular a nitrocellulose strip, may allow sufficient fractionation of the blood to enhance significantly the sensitivity/specificity of detection of analytes (e.g., biomarkers) in the separated serum, especially using a graphene-based detector. In other words, although the use of a nitrocellulose strip in the dermal patch 100 according to some embodiments may not result in fractionation of the whole blood sample with the same degree of separation quality that is achievable via traditional fractionation methods, such as differential centrifugation; nonetheless, use of such a nitrocellulose strip in embodiments of the dermal patch 100 may significantly enhance the sensitivity/specificity for the detection of a variety of analytes (e.g., biomarkers) using a variety of detectors, such as graphene-based detectors, relative to the use of a whole blood sample for such detection. In some embodiments in which the detector 110 is a graphene-based detector, the nitrocellulose strip may be positioned within the collection chamber 312 and coupled to the detector 110 and the detector 110 may detect the target analyte via the nitrocellulose strip.

Furthermore, in some embodiments, the serum-separation element may include at least one fibrous membrane configured to capture at least a portion of one or more cellular components of the received blood, thereby separating a serum (or a plasma) component of the blood. In some embodiments, the separated plasma or the serum component may still include some cellular elements. Even without having a level of fractionation that is achieved via traditional methods, such as differential centrifugation, the separated serum component may be utilized to achieve an enhanced detection sensitivity/specificity relative to using whole blood for detecting, and optionally quantifying, a variety of target analytes in a drawn blood sample. Some examples of such target analytes may include, without limitation, a biomarker (e.g., troponin, brain natriuretic peptide (BnP), or other biomarkers including those disclosed herein).

The separated serum component may include any of a plurality of red blood cells and/or a plurality of white blood cells and/or platelets. However, the concentration of such cellular components in the separated serum component may be less than that in the whole blood by a factor in a range of about 2 to about 1000, though lower concentrations may also be achieved.

While the above describes the dermal patch 100 as including the detector 110, in other embodiments, the detector 110 may be omitted. In these embodiments, the collection chamber 312 may be configured to store the processed physiological sample so that the processed physiological sample may be analyzed at a later time as previously discussed herein. Furthermore, in such embodiments, an absorbent element (e.g., a nitrocellulose strip, a microfiber filter, gauze, a non-woven sheet, a polymer, etc.) may be in communication with the collection chamber 312 to collect at least a portion of the drawn physiological sample. For example, in one embodiment where the collection chamber 312 stores the drawn physiological sample for later testing, a laboratory technician may remove the drawn physiological sample from the dermal patch 100 and employ a detector or another device that is external to the dermal patch 100 to analyze the drawn physiological sample (e.g., for further genetic testing).

In some embodiments, after the physiological sample is collected (e.g., by contacting the drawn physiological sample to the absorbent element), the user of the dermal patch 100 may place the dermal patch 100 into a secure travel safe bag. This bag can be humidity controlled, or temperature controlled or oxygen controlled, or UV/Light controlled or for any purpose required to store the physiological sample.

As further depicted in FIG. 1, the dermal patch 100 may house a computer system (e.g., in the form of a programmed ASIC) 700 that is in communication with the detector 110. The connection between the computer system 700 and the detector 110 may be established via any of a wired or wireless protocol. In some embodiments, the computer system 700 and/or the detector 110 can be supplied with power via an on-board power supply (e.g., a battery incorporated within the dermal patch 100). Alternatively, in some implementations, the computer system 700 and/or the detector 110 can be provided with power via an external device (e.g., a wearable device). Such transfer of power from an external device may be achieved using techniques known in the art, such as inductive coupling between two elements (e.g., two coils) provided in the dermal patch 100 and the external device.

As will be discussed in further detail herein, the computer system 700 receives one or more signals (e.g., detection signals) generated by the detector 110 and determines whether the target analyte is present in the drawn physiological sample at a quantity above the detector's limit-of-detection (LOD). In some embodiments, the computer system 700 may be configured to determine a quantitative level of the target analyte (e.g., the concentration of the target analyte in the collected sample) based on the received signals, e.g., by employing one or more calibration tables.

Figure 9:
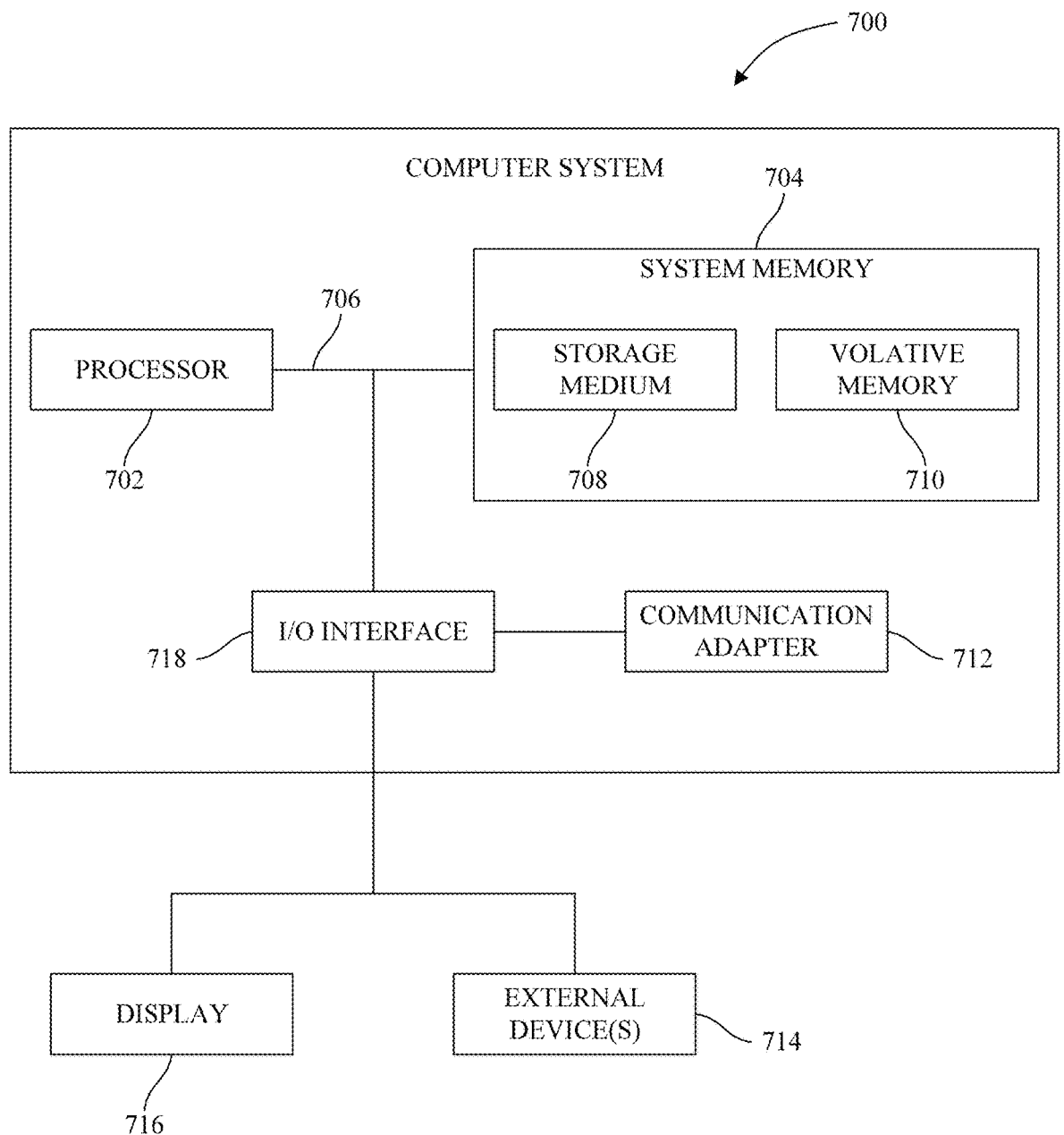
FIG. 9 depicts diagrammatically a computer system that can be utilized to analyze data generated by a detector incorporated in a dermal patch in accordance with an exemplary embodiment.

Referring now to FIG. 9, the computer system 700 is shown in accordance with an exemplary embodiment. As used herein a computer system (or device) is any system/device capable of receiving, processing, and/or sending data. Computer systems include, but are not limited to, microprocessor-based systems, personal computers, servers, handheld computing devices, tablets, smartphones, multiprocessor-based systems, mainframe computer systems, virtual reality ("VR") headsets and the like.

As shown in FIG. 9, the computer system 700 includes one or more processors or processing units 702, a system memory 704, and a bus 706 that couples various components of the computer system 700 including the system memory 704 to the processor 702.

The system memory 704 includes a computer readable storage medium 708 and volatile memory 710 (e.g., Random Access Memory, cache, etc.). As used herein, a computer readable storage medium includes any media that is capable of storing computer readable program instructions and is accessible by a computer system. The computer readable storage medium 708 includes non-volatile and non-transitory storage media (e.g., flash memory, read only memory (ROM), hard disk drives, etc.). Computer readable program instructions as described herein include program modules (e.g., routines, programs, objects, components, logic, data structures, etc.) that are executable by a processor. Furthermore, computer readable program instructions, when executed by a processor, can direct a computer system (e.g., the computer system 700) to function in a particular manner such that a computer readable storage medium (e.g., the computer readable storage medium 708) comprises an article of manufacture. Specifically, when the computer readable program instructions stored in the computer readable storage medium 708 are executed by the processor 702 they create means for determining a presence of a target analyte as a function of signals sent by the detector 110 and optionally for quantifying a level of a target analyte as a function of signals sent by the detector 110 (e.g., the steps 814 and 816 of the method 800).

The bus 706 may be one or more of any type of bus structure capable of transmitting data between components of the computer system 700 (e.g., a memory bus, a memory controller, a peripheral bus, an accelerated graphics port, etc.).

The computer system 700 may further include a communication adapter 712 which allows the computer system 700 to communicate with one or more other computer systems/devices via one or communication protocols (e.g., Wi-Fi, BTLE, etc.) and in some embodiments may allow the computer system 700 to communicate with one or more other computer systems/devices over one or more networks (e.g., a local area network (LAN), a wide area network (WAN), a public network (the Internet), etc.).

In some embodiments, the computer system 700 may be connected to one or more external devices 714 and a display 716. As used herein, an external device includes any device that allows a user to interact with a computer system (e.g., mouse, keyboard, touch screen, etc.). An external device 714 and the display 716 may be in communication with the processor 702 and the system memory 704 via an Input/Output (I/O) interface 718.

The display 716 may display a graphical user interface (GUI) that may include a plurality of selectable icons and/or editable fields. A user may use an external device 714 (e.g., a mouse) to select one or more icons and/or edit one or more editable fields. Selecting an icon and/or editing a field may cause the processor 702 to execute computer readable program instructions stored in the computer readable storage medium 708. In one example, a user may use an external device 714 to interact with the computer system 700 and cause the processor 702 to execute computer readable program instructions relating to at least a portion of steps of the methods disclosed herein.

While FIG. 1 depicts the dermal patch 100 as including the computer system 700, in some embodiments, the computer system 700 may be omitted. In these embodiments, the detector 110 may detect the target analyte without any computer system 700 needed (e.g., a lateral flow assay). When the detector 110 is a lateral flow assay, the top portion 200 may include a window that allows for visual inspection of the detector 110. Such visual inspection can be used to observe the result of the test provided by the detector 110. Furthermore, in other embodiments the computer system 700 may be external from the dermal patch 100. In these embodiments, the computer system 700 may be in wireless communication with the detector 110 as previously discussed herein.

Referring now to FIGS. 10-19, another dermal patch 800 is depicted in accordance with an exemplary embodiment. As will be discussed in further detail herein, the dermal patch 800 is similar to the dermal patch 100, however in the dermal patch 800, the detector 110 and the fluid pouch 500 has been omitted.

The dermal patch 800 includes a housing 802. The housing 802 may be formed using a variety of suitable materials including, but not limited to, polymeric materials, e.g., polyolefins, PET (Polyethylene Terephthalate), polyurethanes, polynorbornenes, polyethers, polyacrylates, polyamides (Polyether block amide also referred to as Pebax®), polysiloxanes, polyether amides, polyether esters, trans-polyisoprenes, polymethyl methacrylates (PMMA), cross-linked trans-polyoctylenes, cross-linked polyethylenes, cross-linked polyisoprenes, cross-linked polycyclooctenes, inorganic-organic hybrid polymers, co-polymer blends with polyethylene and Kraton®, styrene-butadiene co-polymers, urethane-butadiene co-polymers, polycaprolactone or oligo caprolactone co-polymers, polylactic acid (PLLA) or polylactide (PL/DLA) co-polymers, PLLA-polyglycolic acid (PGA) co-polymers, and photocrosslinkable polymers. In some embodiments, some of the housing 802 may be formed poly(dimethylsiloxane) (PDMS) to allow visibility of components disposed within the housing 802.

The housing 802 includes a top surface 804 and an opposed bottom surface 806. The housing 800 defines an aperture 808 that extends through the housing 802. Stated another way, the aperture 808 extends between the top surface 804 and the bottom surface 806.

The dermal patch 800 also includes an adhesive layer 810 disposed on the bottom surface 806 thereof and surrounds the aperture 808 such that the adhesive layer 810 does not cover the aperture 808. In use, the dermal patch 800 may be attached to a subject's skin as previously discussed herein with respect to the dermal patch 100. In some embodiments, a removeable protective liner may cover the adhesive layer as previously discussed herein.

The dermal patch 800 also includes a septum 812 which extends longitudinally throughout the housing 802 such that the septum 812 covers the aperture 808. The septum 812 may be formed of a polymeric material, such as polyisoprene, and may be configured such that it can be punctured via a lancet, as previously discussed with respect to the septum 106. In some embodiments, the thickness of the septum 812 can be in a range of about 0.015" to about 0.040".

In some embodiments, the septum 812 may be omitted. In these embodiments, a lancet 900 (depicted in FIGS. 12-14) that engages with the aperture 808 and seals the dermal patch 800 such that a vacuum may be created within the dermal patch 800 may be employed to draw a physiological sample as discussed in further detail below.

Figure 12:
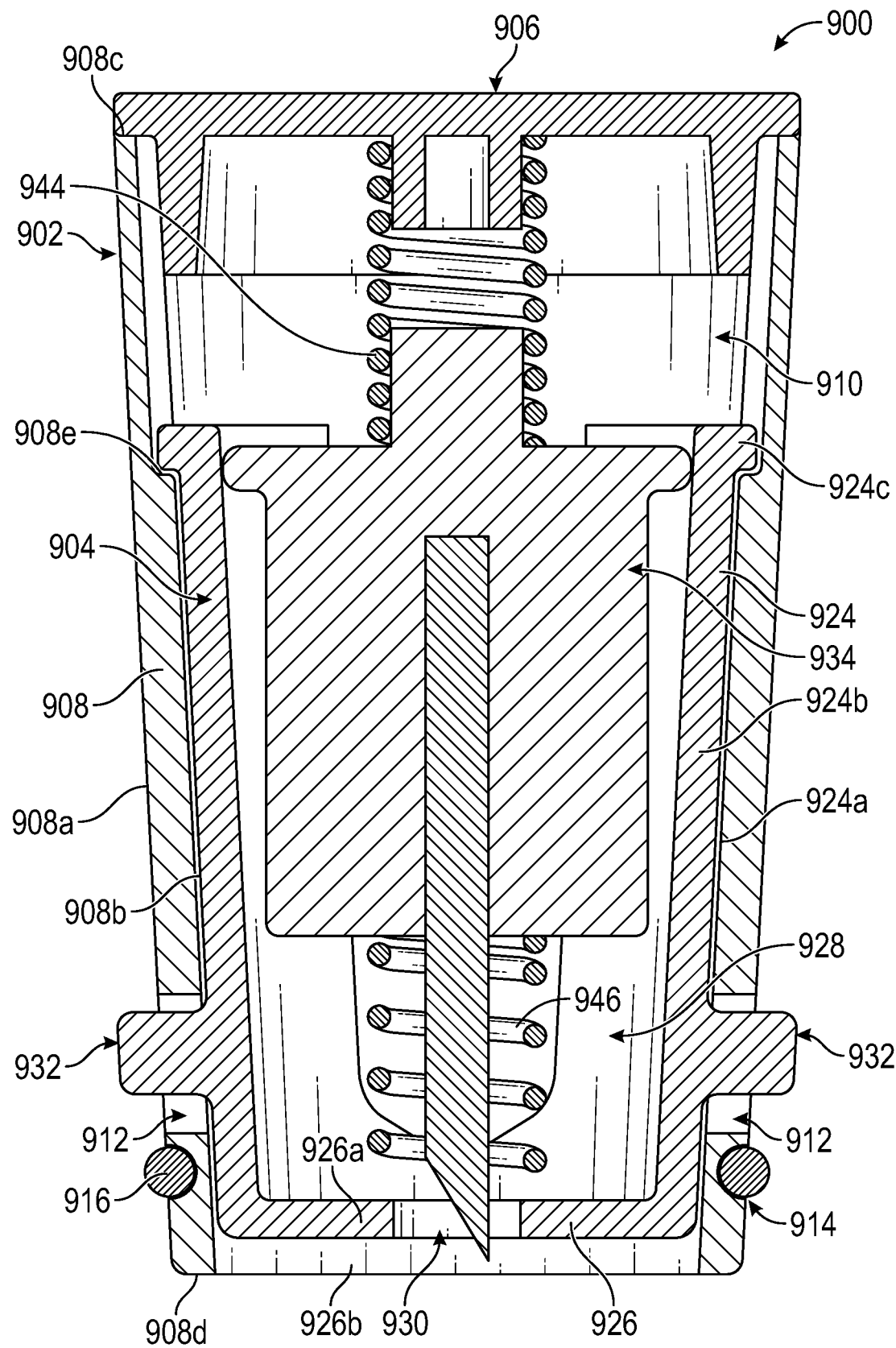
FIG. 12 is a cross sectional view of a lancet in accordance with an exemplary embodiment.
Figure 13:
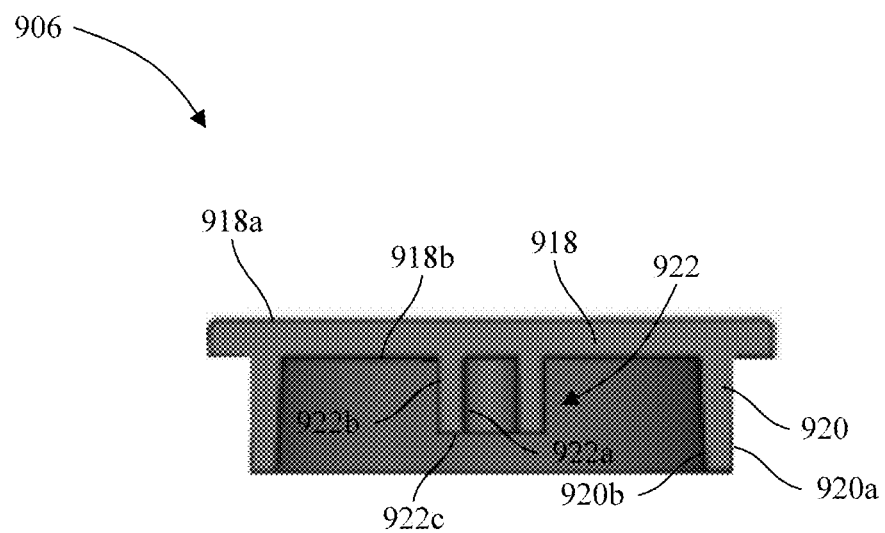
FIG. 13 is a cross sectional view of a cover of a lancet in accordance with an exemplary embodiment.
Figure 14:
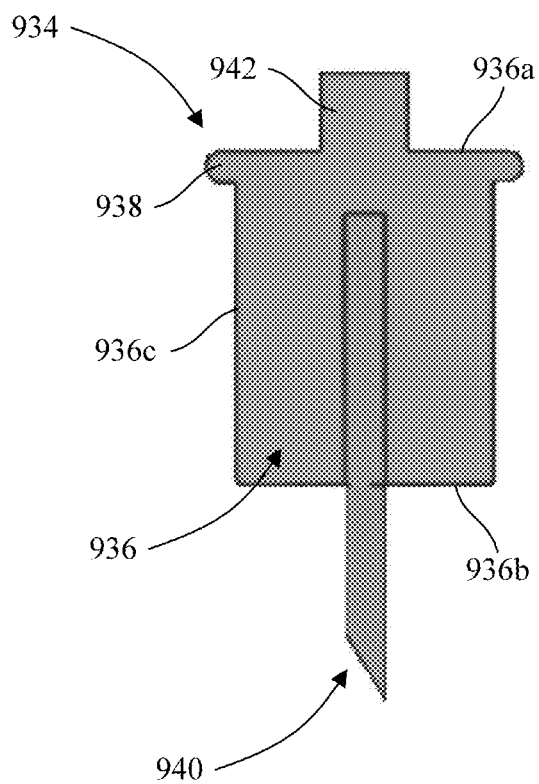
FIG. 14 is a cross sectional view of a needle platform of a lancet in accordance with an exemplary embodiment.
Figure 15:
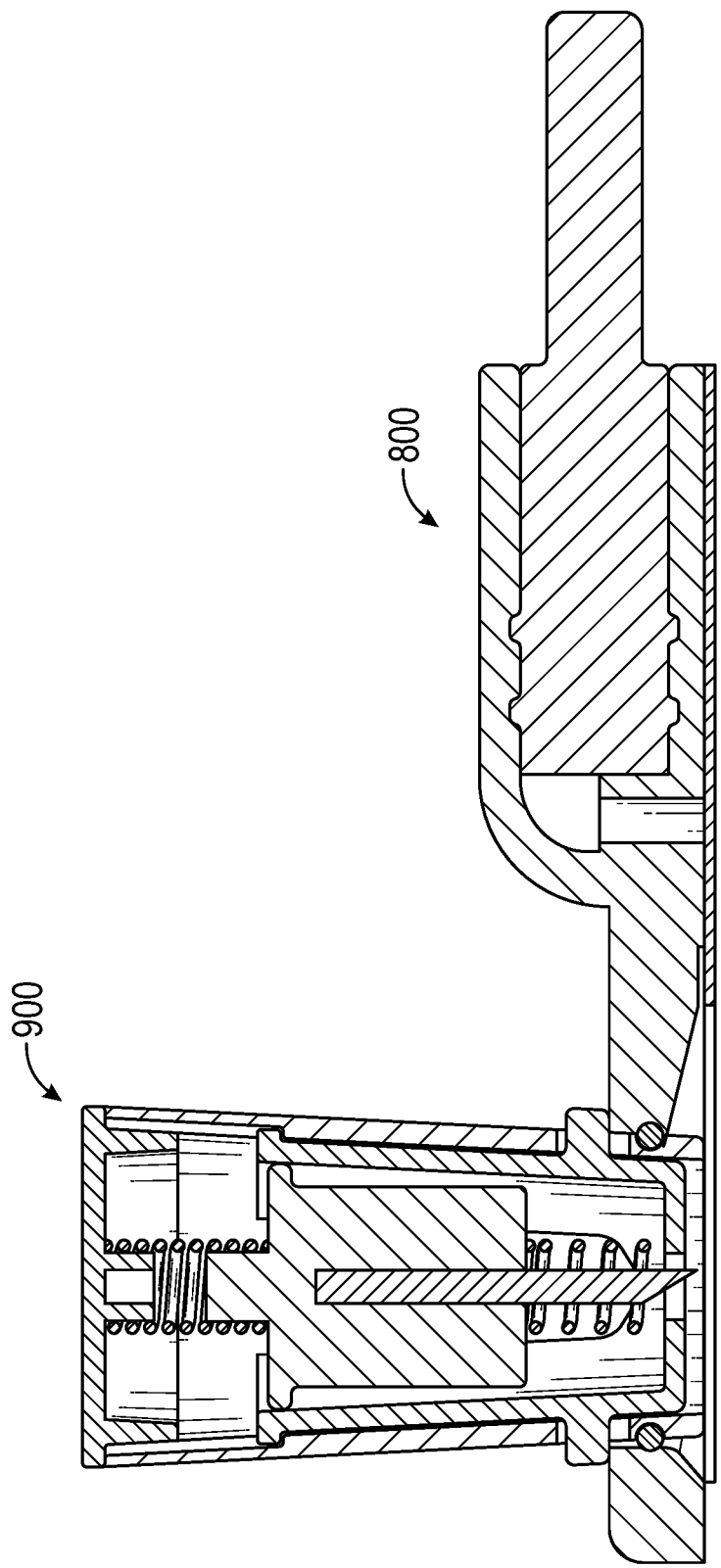
FIG. 15 is a cross sectional view of a lancet connected to a dermal patch, wherein the lancet is in an undeployed position lancet in accordance with an exemplary embodiment.

Referring now to FIGS. 12-14, the lancet 900 is depicted in accordance with an exemplary embodiment. The lancet 900 includes an outer wall 902, a concentric inner wall 904 and a cover 906. The inner wall 904 is retained within the outer wall 902 and the cover 906 is coupled to the outer wall 902 such that the cover 906 seals the lancet 900.

The outer wall 902 includes generally cylindrical wall 908. The wall 908 includes an outer surface 908a, an opposed inner surface 908b, a top surface 908c, and a bottom surface 908d. The outer surface 908a and the inner surface 908b extend vertically between the top surface 908c and the bottom surface 908d and the top surface 908c and the bottom surface 908d extend horizontally between the outer surface 908a and the inner surface 908b. The wall 908 further includes a ledge 908e that extends circumferentially within the outer wall 902.

The inner surface 908b defines an inner chamber 910 of the outer wall 902. The wall 908 includes plurality of apertures 912 that extend through the wall 908. Stated another way, the apertures 912 extend between the outer surface 908a and the inner surface 908b of the wall 908. The wall 908 also includes a groove 914 that extends circumferentially around the wall 908. The groove 914 is shaped and dimensioned to accommodate an elastomeric O-ring 916 such that the elastomeric O-ring 916 is retained within the groove 918.

The cover 906 includes a top wall 918 with a top surface 918a and a bottom surface 918b. When the cover 906 is coupled to the outer wall 902, the bottom surface 918b contacts the top surface 908c of the wall 908.

The cover 906 further includes an outer wall 920 that extends vertically from the top wall 918. Specifically, the outer wall 920 extends from the bottom surface 918b of the top wall 918. The outer wall 920 includes an outer surface 920a, an opposed inner surface 920b, and a bottom surface 920c. The outer surface 920a and the inner surface 920b extend vertically between the bottom surface 918b of the top wall 918 and the bottom surface 920c. The bottom surface 920c extends horizontally between the outer surface 920a and the inner surface 920b. Furthermore, when the cover 906 is coupled to the outer wall 902, the outer surface 920a contacts the inner surface 908b of the wall 908.

The cover 906 also includes an inner wall 922 that extends vertically from the top wall 918. Specifically, the inner wall 922 extends from the bottom surface 918b of the top wall 918. The inner wall 922 includes an inner surface 922a, an opposed outer surface 922b, and a bottom surface 922c. The outer surface 922a and the inner surface 922b extend vertically between the bottom surface 918b of the top wall 918 and the bottom surface 922c. The bottom surface 922c extends horizontally between the outer surface 922a and the inner surface 922b.

The inner wall 904 is retained within the inner chamber 910 of the outer wall 902 and includes a generally cylindrical wall 924 and a bottom wall 926. The wall 924 extends vertically from the bottom wall 926 and bottom wall 926 extends horizontally between opposing sides of the wall 924. The wall 924 includes an outer surface 924a, an opposed inner surface 924b and the bottom wall 926 includes a top surface 926a and an opposed bottom surface 926b. The wall 924 further includes a ledge 924c that contacts the ledge 908e of the wall 908. The inner surface 924b of the wall 924 defines an inner volume 928 of the inner wall 904. The bottom wall 926 defines an aperture 930 that extends through the bottom wall 924. Stated another way, the aperture 930 extends between the top surface 926a and the bottom surface 926b of the bottom wall 926.

The inner wall 904 further includes a plurality of latches 932 that extend horizontally from and perpendicular to the wall 924. Specifically, the plurality of latches 932 extend horizontally from and perpendicular to the outer surface 924a of the wall 924. When the inner wall 904 is coupled to the outer wall 902, the latches 932 extend through the apertures 912.

The lancet 900 further includes a needle platform 934 that is retained within the inner volume 928 of the inner wall 904. The needle platform includes a cylinder 936 with a top surface 936a, a bottom surface 936b and an outer surface 936c that extends vertically between the top surface 936a and the bottom surface 936b. The needle platform 934 also includes a lip 938 that extends horizontally beyond the outer surface 9336c of the cylinder 936. When the needle platform is within the inner volume 928 of the inner wall 904, the lip 938 contacts the inner surface 924b of the inner wall 904. The needle platform 934 is coupled to and supports a needle 940. In some embodiments, the needle 940 is molded into the needle platform 934. The needle platform 934 further includes a notch 942, which extends vertically from and perpendicular to the top surface 936a of the cylinder 936.

The lancet 900 also includes a first biasing element (i.e., a spring) 944 and a second biasing element (e.g., a spring) 946, which collectively allow causing the needle to puncture the subject's skin and then retract. The first biasing element 944 extends circumferentially around the inner wall 922 of the cover 906 and extends circumferentially around the notch 942 of the needle platform 934. Furthermore, the first biasing element 944 contacts the bottom surface 918b of the top wall 918 of the cover 906 and contacts the top surface 936a of the needle platform 934. The second biasing element 946 extends circumferentially around the needle 940 and contacts the bottom surface 936b of the needle platform 934 and the top surface 926a of the inner wall 904.

Figure 16:
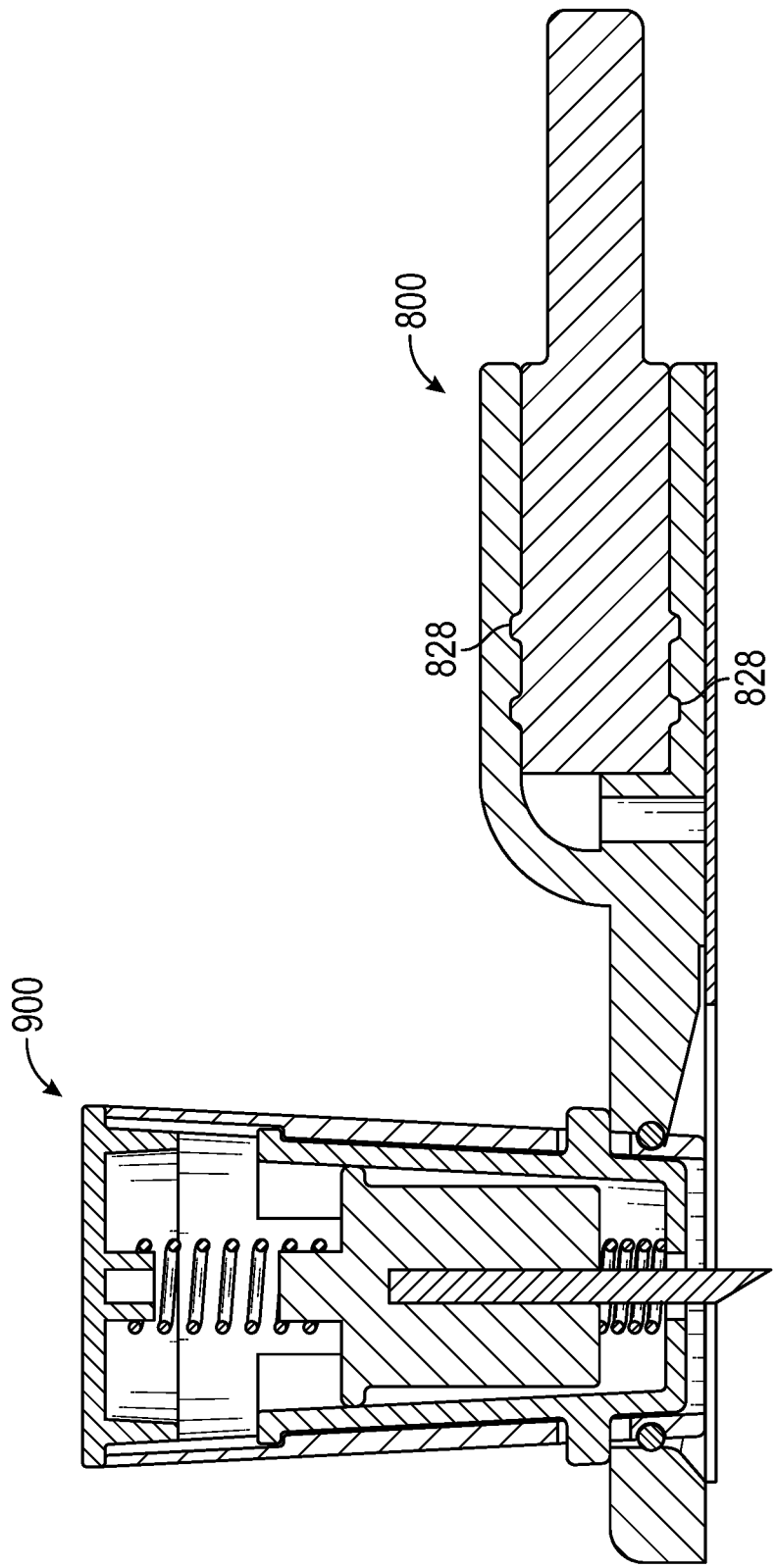
FIG. 16 is a cross sectional view of a lancet connected to a dermal patch, wherein the lancet is in a deployed position lancet in accordance with an exemplary embodiment.

The needle platform 934 is moveable between an undeployed position (FIG. 15) and a deployed position (FIG. 16). In the undeployed position, the first biasing element 944 and the second biasing element 946 are, respectively, in a compressed and a stretched state so as to retain the needle 940 within the lancet 900.

After the dermal patch 800 is adhered to the skin of the subject, the lancet 900 may be used to draw a physiological sample from the subject. First, a user may place the lancet vertically above the aperture 808 such that the latches 932 of the lancet 900 contact the top surface 804 of the housing 802. When a user of the dermal patch pushes the lancet 900 further into the dermal patch 800, the latches 932 are displaced thereby releasing the needle platform 934 allowing the first biasing element 944 to extend. When the first biasing element 944 extends, the first biasing element 944 moves the needle platform 934 from the undeployed position to the deployed position. In the deployed position, the needle 940 extends through the aperture 930 of the inner wall 904. This allows the needle 940 to puncture the septum 812 and draw a physiological sample as previously discussed herein. Furthermore, when compressed into the dermal patch 800, the elastomeric O-ring 916 forms an airtight seal within the dermal patch 800 thereby retaining the drawn physiological sample between the septum and the skin of the subject.

While the above describes the lancet 900 as used in conjunction with the dermal patch 800, in other embodiments the dermal patch 800 may be used with the dermal patch 100. Furthermore, while the lancet 900 is depicted as separate from the dermal patch 800, in other embodiments, the lancet 900 and the dermal patch may be formed as an integral unit (e.g., the lancet can be molded to the dermal patch 800. In this embodiment, the lancet 900 may be moved from the undeployed position to the deployed position by rotating or pushing the lancet as previously discussed.

Figure 11:
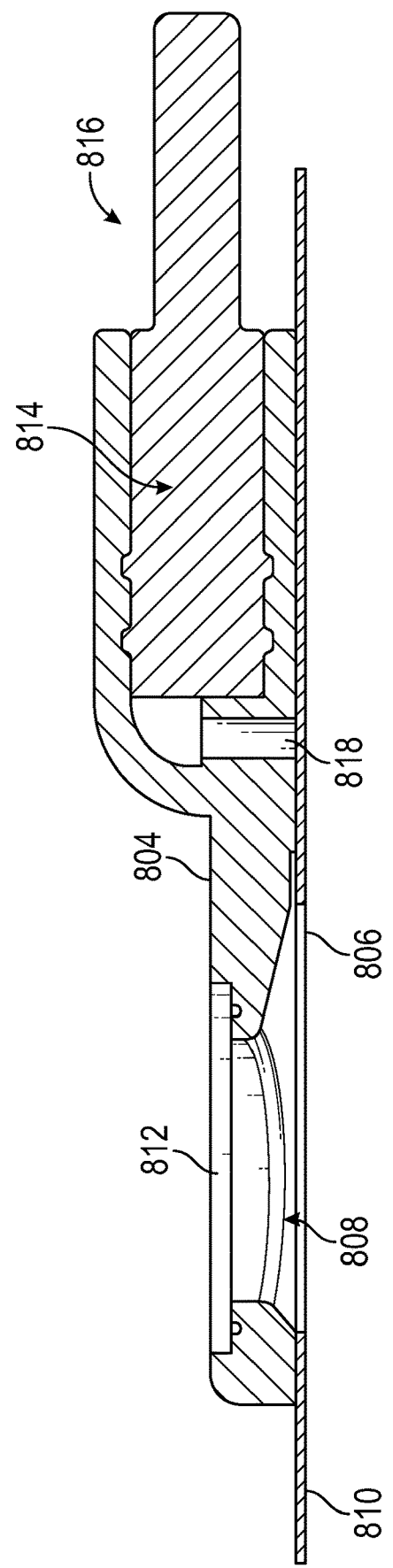
FIG. 11 is a cross sectional view of a dermal patch in accordance with an exemplary embodiment.

With reference to FIG. 11, similar to the previous embodiment, the housing 802 further includes a pin receptacle 814 that is shaped and dimensioned to receive a pin 816 and retain the pin 816 in place via an interference fit. The housing 802 further includes a vacuum channel 818 that is in fluid communication with the pin receptacle 814.

Figure 17:
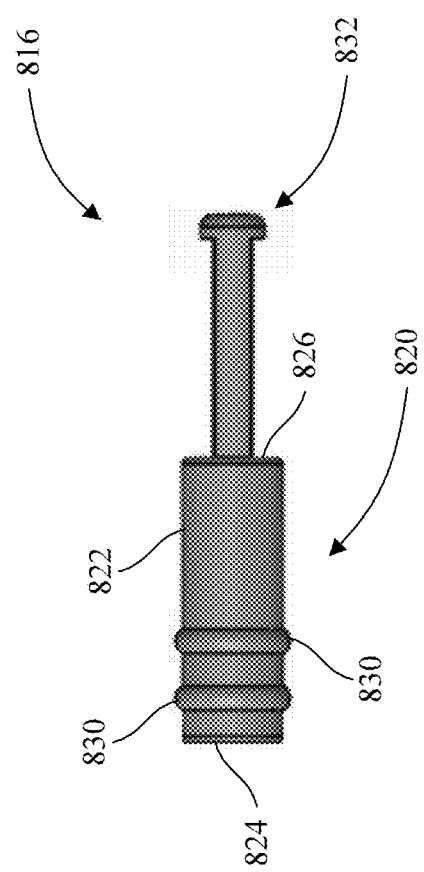
FIG. 17 depicts a pin of a dermal patch in accordance with an exemplary embodiment.
Figure 18:
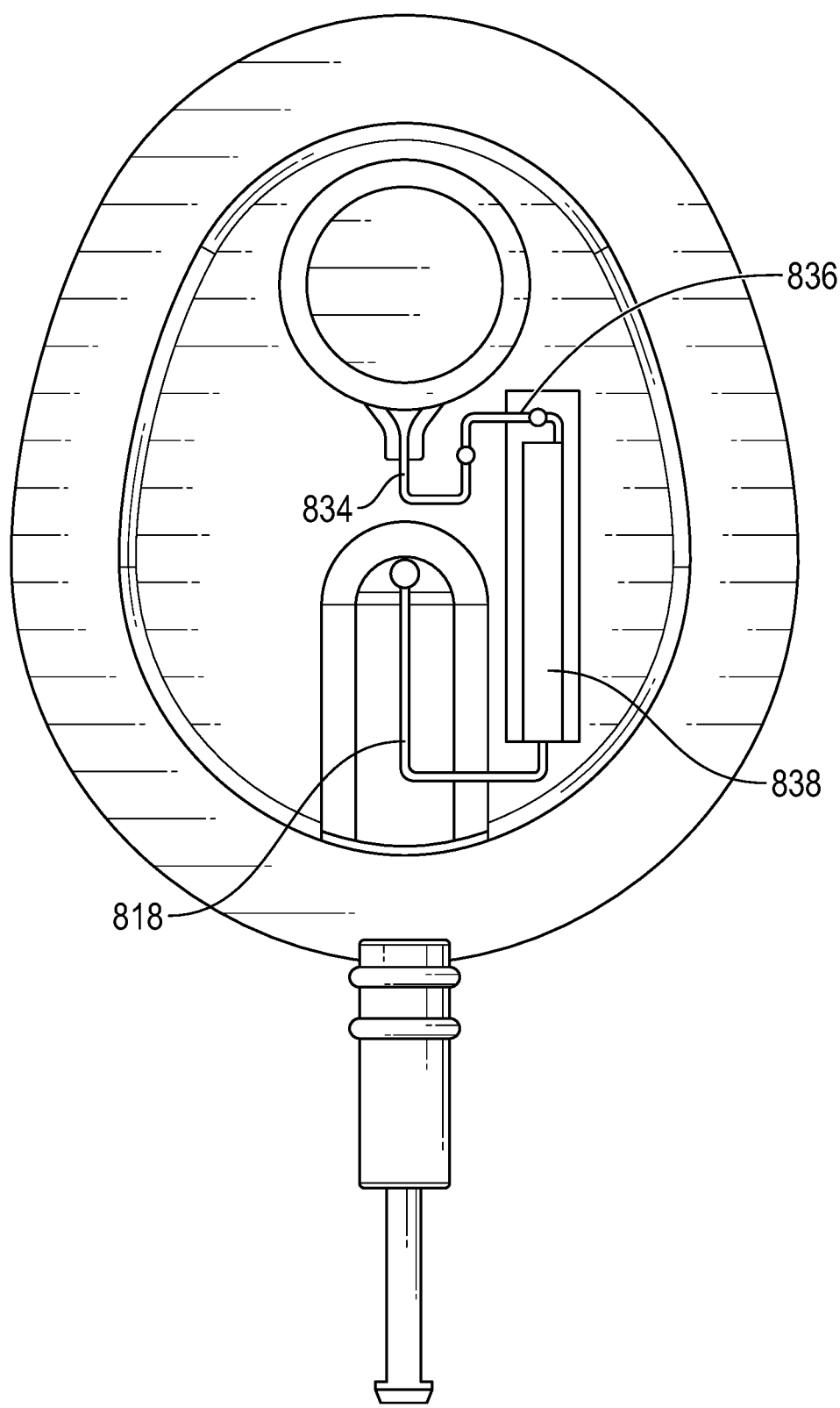
FIG. 18 diagrammatically illustrates a dermal patch in accordance with an exemplary embodiment.

Referring now to FIG. 17, the pin 816 includes a cylindrical barrel 820, which includes an outer surface 822 that extends between a proximal end 824 and a distal end 826 of the barrel 820. The outer surface 822 defines a plurality of grooves 828 that extend circumferentially about the barrel 820. The grooves 828 are shaped and dimensioned to retain elastomeric O-rings 830. When the barrel 820 is positioned within the pin receptacle 814 (in the "undeployed position"), the elastomeric O-rings 830 contact the surface of the pin receptacle 814 to create an airtight seal between the barrel 820 and the inner surface of the pin receptacle 814.

The pin 816 further includes a handle 832 that is connected to the barrel 820 and extends external to the pin receptacle 814 when the barrel 820 is within the pin receptacle 814 and hence can be employed to remove the barrel 820 from the pin receptacle 814 and generate a vacuum for drawing a physiological sample. In some embodiments, the dermal patch and the pin can be configured such that the pin can be used to apply a positive pressure to create fluidic flow.

A user can pull the handle 832 as previously discussed herein to remove pin 816 from the pin receptacle 814 to create a vacuum within the vacuum channel 818 as previously discussed herein. The vacuum channel is in communication with a physiological sample channel 834 which is in communication with a collection chamber 836. Thus, removing the pin barrel 820 from the pin receptacle 814 results in the generation of a vacuum within the sample channel 834, thereby facilitating the drawing of a physiological sample from the subject and directing the drawn physiological sample into a collection chamber 836 as previously discussed herein.

The collection chamber 836 an absorbent element 838 as previously discussed herein. The storage absorbent element 838 contacts the drawn physiological sample and preserves the physiological sample for further testing (i.e., genetic testing) as previously discussed herein.

Figure 19:
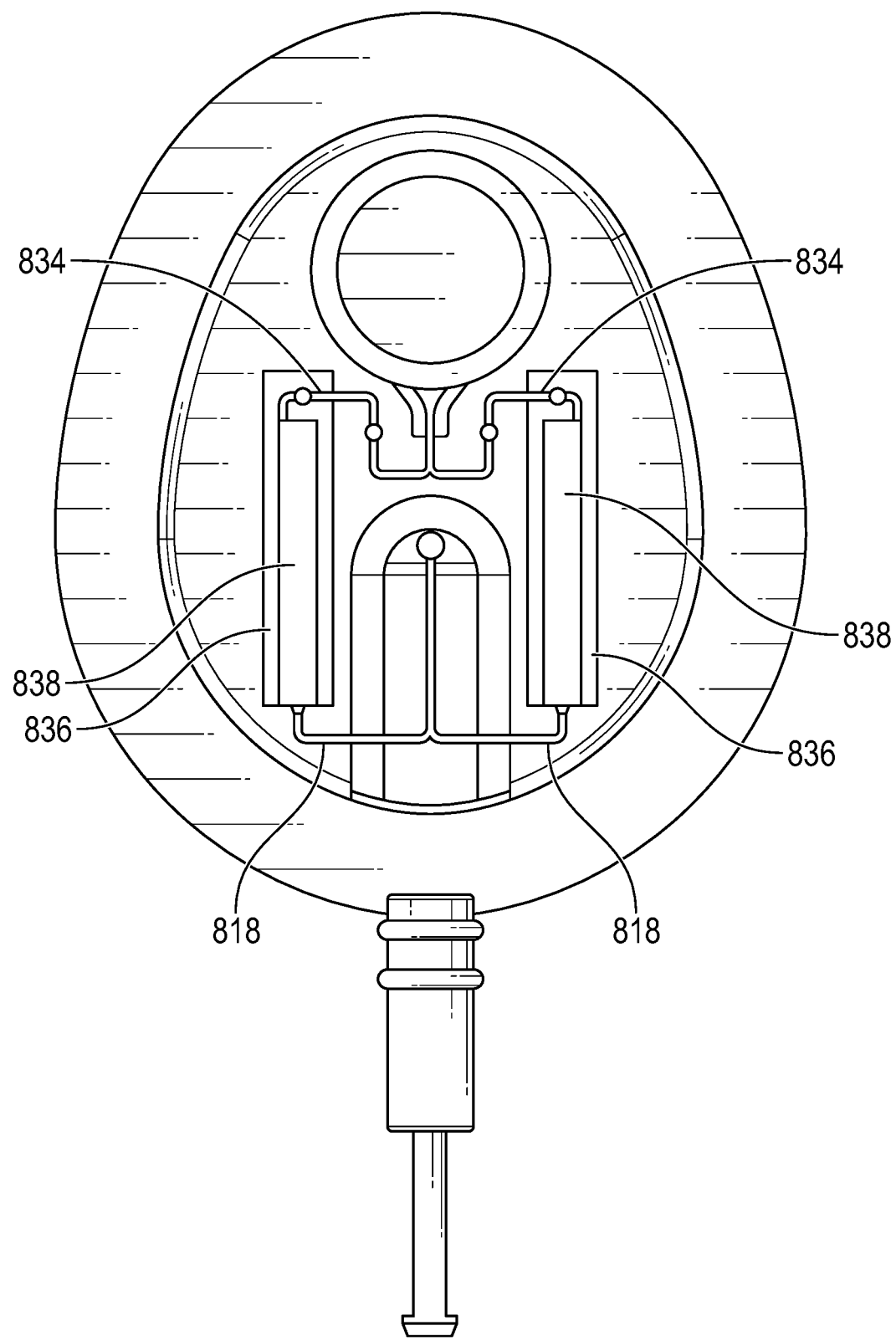
FIG. 19 diagrammatically illustrates a dermal patch with two collection reservoirs in accordance with an exemplary embodiment.
Figure 20:
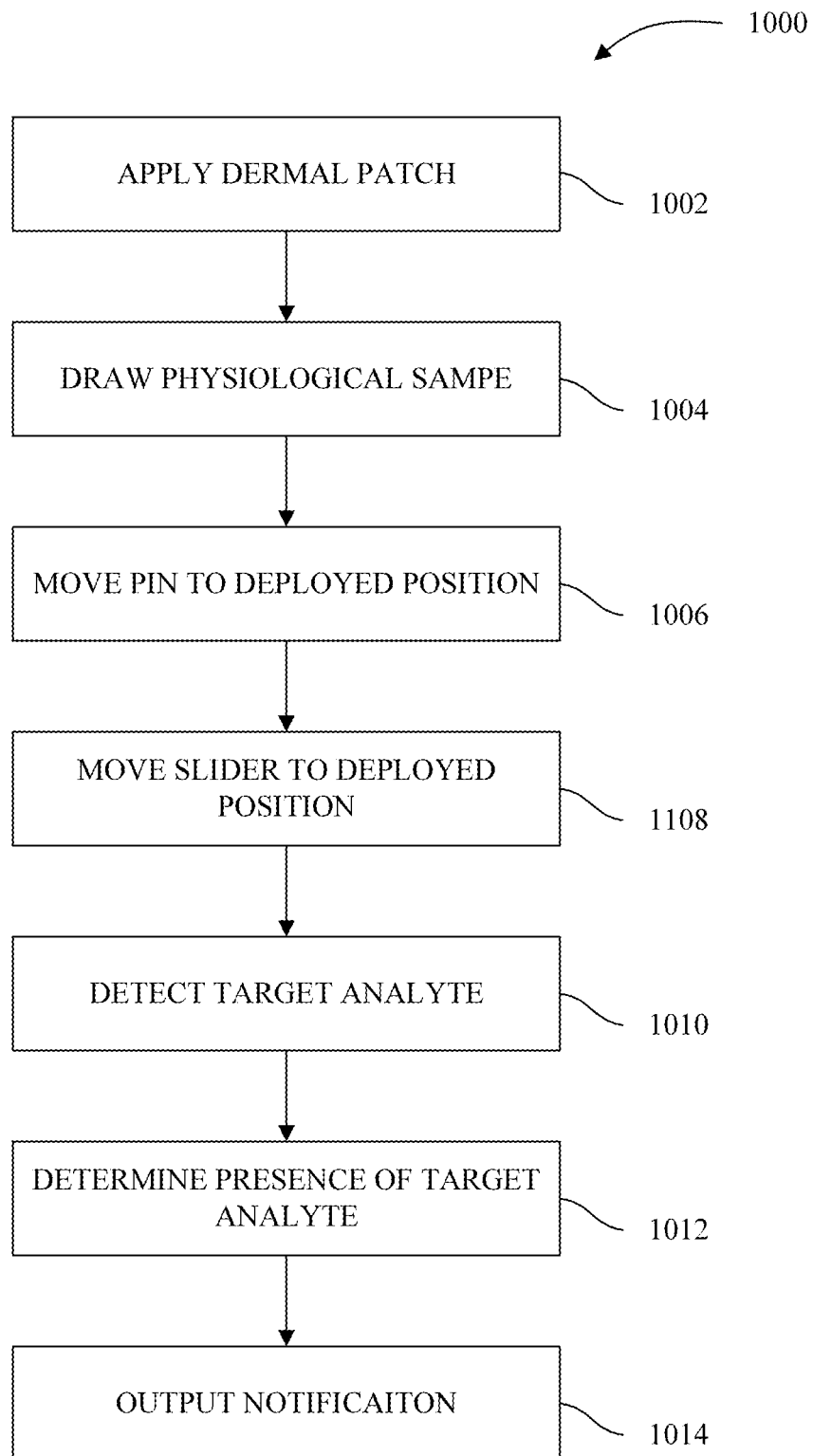
FIG. 20 illustrates a method for detecting a target analyte in a physiological sample in accordance with an exemplary embodiment.

Referring now to FIG. 19, in some embodiments, the dermal patch 800 may include a plurality of collection chambers 836 each with an absorbent element 838. In this embodiment the vacuum channel 818 and the sample channel 834 each branch to both of the collection chambers 836. When the pin 816 is moved to the deployed position, the created vacuum draws the physiological sample to both collection chambers 836 as previously discussed herein.

Figure 10:
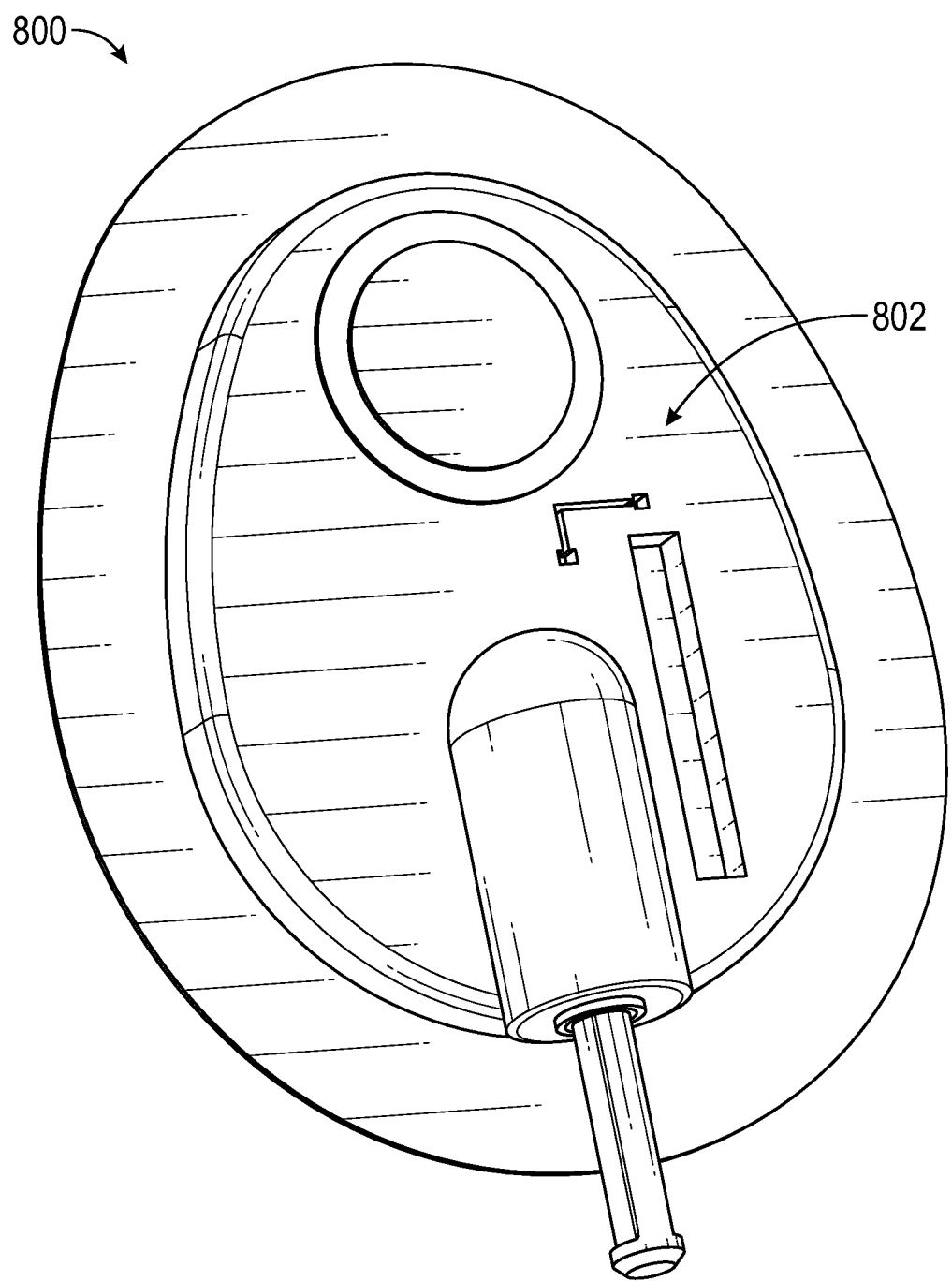
FIG. 10 depicts a dermal patch in accordance with an exemplary embodiment.

Referring now to FIG. 10 a method 1000 for detecting a target analyte in a physiological sample is shown in accordance with an exemplary embodiment. As previously discussed herein, the steps 1014 and 1016 of the method 1000 may be stored as computer readable program instructions in a computer readable storage medium (e.g., the computer readable storage medium 708). A processor that is configured according to an aspect of the present disclosure (hereinafter "a programmed processor") executes the computer readable program instructions for the steps 1012 and 1014 of method 1000. In one embodiment, the programmed processor is the processor 702.

At 1002, the dermal patch 100 is applied to the skin of a subject via the adhesive patch 104 as previously discussed herein.

At 1004, a user of the dermal patch 100 uses the lancet 108 to puncture the skin of the subject to draw a physiological sample as previously discussed herein.

At 1006, the user of the dermal patch 100 moves the pin 400 to the deployed position to draw the physiological sample to the collection chamber 312 as previously discussed herein.

At 1008, the user of the dermal patch 100 moves the slider 600 to the deployed position to transfer the processing fluid stored in the fluid pouch 500 to the collection chamber 312 as previously discussed herein.

After the physiological sample and the processing fluid mix within the collection chamber, at 1010, the detector 110 detects the target analyte in the processed physiological sample and generates a signal indicative thereof as previously discussed herein.

At 1012, the programmed processor receives the signal(s) from the detector 110 and determines the target analyte is present in the physiological sample (or the processed physiological sample) when a level of the target analyte exceeds a LOD and optionally quantifies a level (e.g., concentration) of the target analyte as a function of the received signal(s) as previously discussed herein.

At 1014, the programmed processor outputs a notification indicative of the determined presence of the target analyte and/or the determined level of the target analyte to the display 714. In response to receiving the notification, the display 714 displays the notification.

Figure 21:
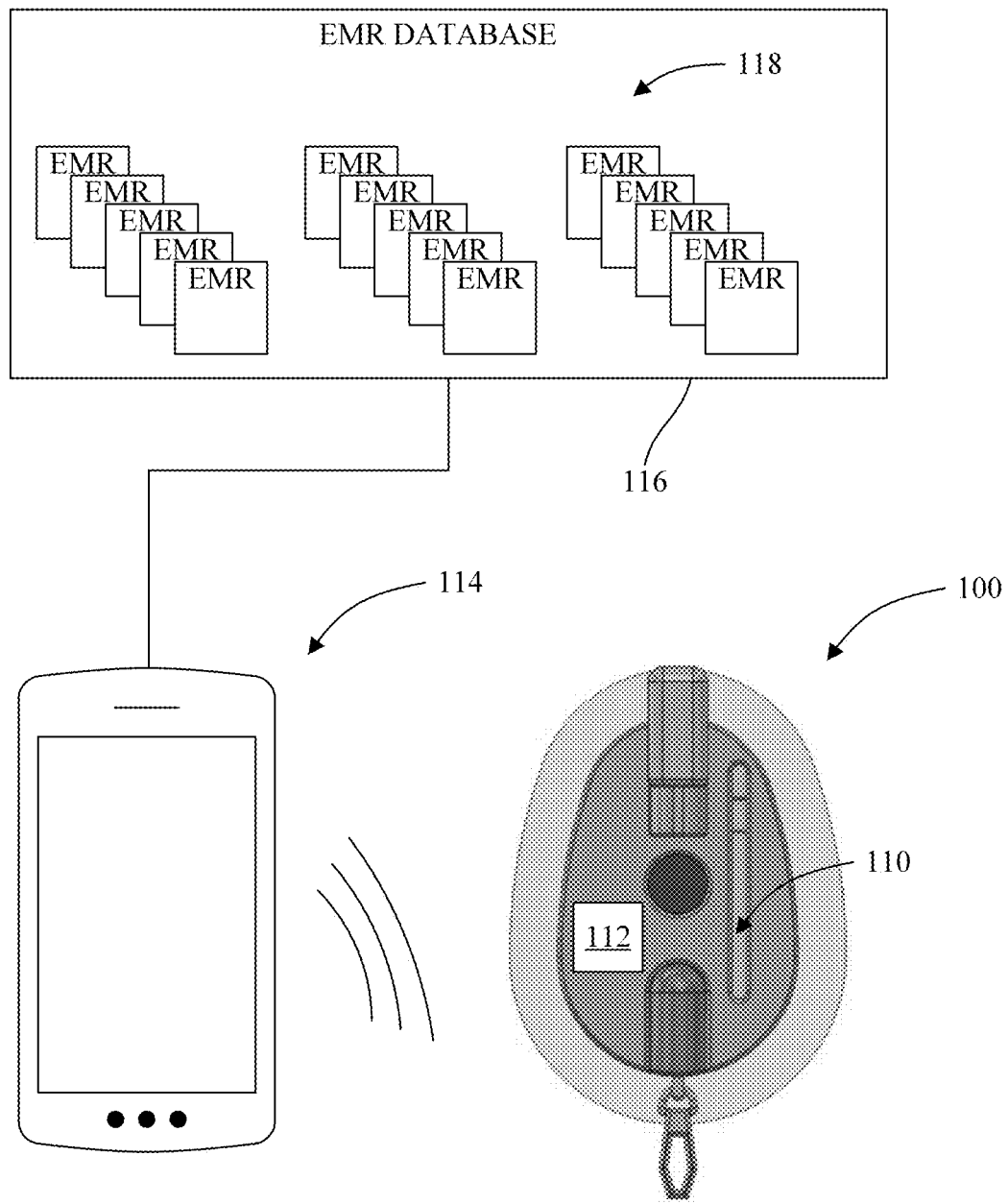
FIG. 21 depicts a dermal patch with a quick response ("QR) code in accordance with an exemplary embodiment.

Referring now to FIG. 21, the dermal patch 100 is shown in accordance with an exemplary embodiment. In this embodiment, a quick response ("QR") code 112 is printed onto the top surface 202 of the top portion 200 of the dermal patch. In this embodiment, a user may install an application stored as computer readable program instructions on a computer system 114 (i.e., a smartphone, tablet, etc.) and employ a camera of the computer system 114 to take a photo of the QR code 112 which is the saved in a memory of the computer system 114. Generally, the computer system 114 includes same or similar components as the computer system 700 (i.e., system memory, processor, display, etc.). In this embodiment, a processor of the computer system 114 may execute the program instructions associated with the application to retrieve the photograph from the memory.

In some embodiments, the computer system 114 may be in communication with an electronic medical record ("EMR") database 116 via a network connection. The EMR database 116 includes a plurality of EMRs 118 each associated with an individual subject. In these embodiments, the instructions associated with the application further cause the processor of the computer system 114 to analyze the photograph to identify the QR code 112 and associate the QR code 112 with an EMR 118 stored in the EMR database 116. When the detector 110 includes a visible readout and the readout is included in the photograph, the processor of the computer system 114 may further analyze the received photo to evaluate the readout and automatically determine the presence of a target analyte and/or a level of a target analyte based on the readout as previously discussed herein.

Figure 22:
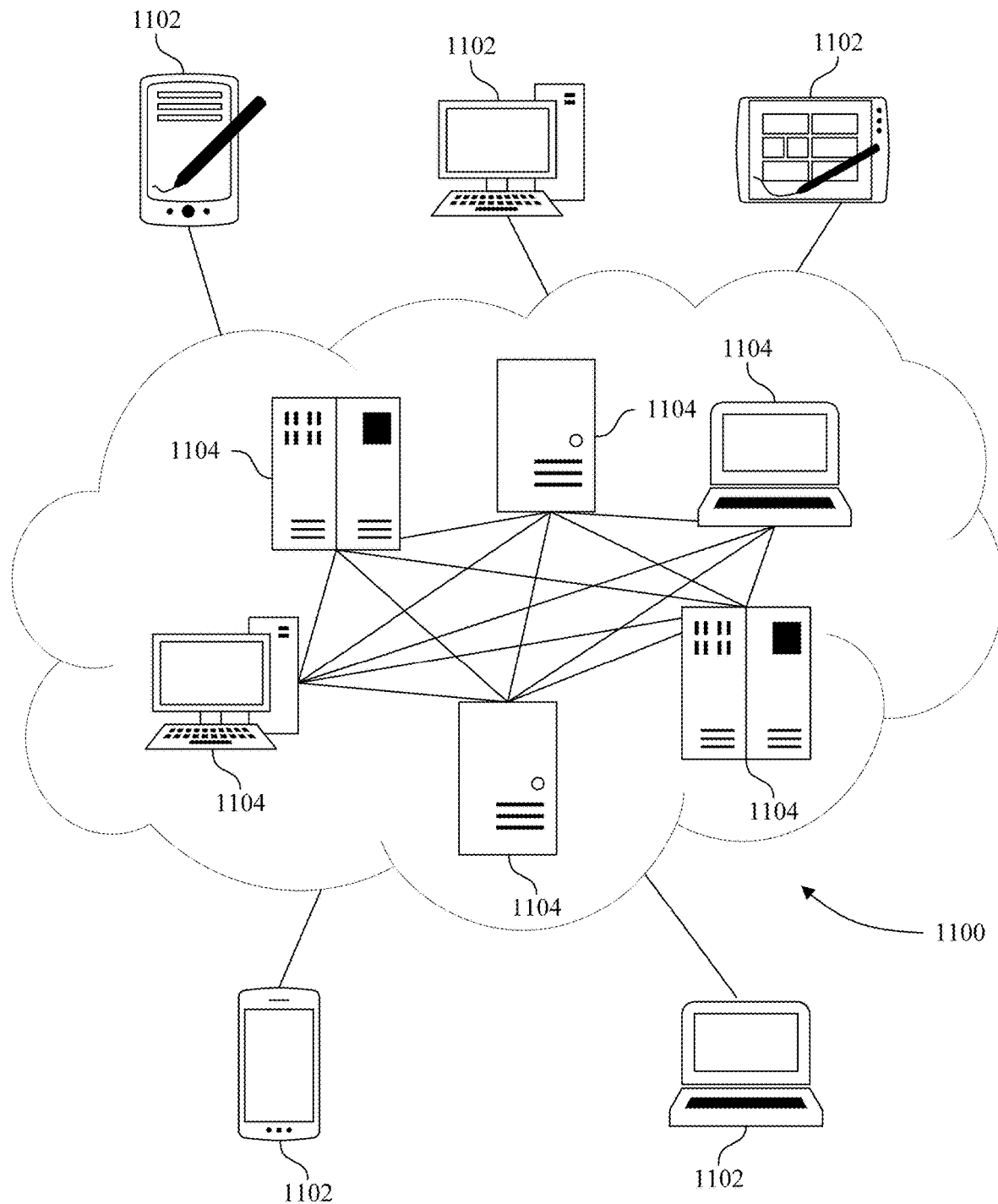
FIG. 22 depicts a cloud computing environment in accordance with an exemplary embodiment.

Referring now to FIG. 22, a cloud computing environment 1100 is depicted in accordance with an exemplary embodiment. The cloud computing environment 1100 is connected to one or more user computer systems 1102 and provides network access to shared computer resources (i.e., storage, memory, applications, virtual machines, etc.) to the one or more user computer systems 1102. As depicted in FIG. 22, the cloud computing environment 1100 includes one or more interconnected nodes 1104. Each node 1104 may be a computer system or device with local processing and storage capabilities. The nodes 1104 may be grouped and in communication with one another via one or more networks. This allows the cloud computing environment 1100 to offer software services to the one or more user computer systems 1102 and as such, a user computer system 1102 does not need to maintain resources locally.

In one embodiment, a node 1102 includes the computer system 700 or the computer system 114 and as such, includes the computer readable program instructions for carrying out various steps of the methods discussed herein. In these embodiments, a user of a user computer system 1102 that is connected the cloud computing environment 1100 may cause a node 1104 to execute the computer readable program instructions to carry out various steps of the methods disclosed herein.

Figure 23:
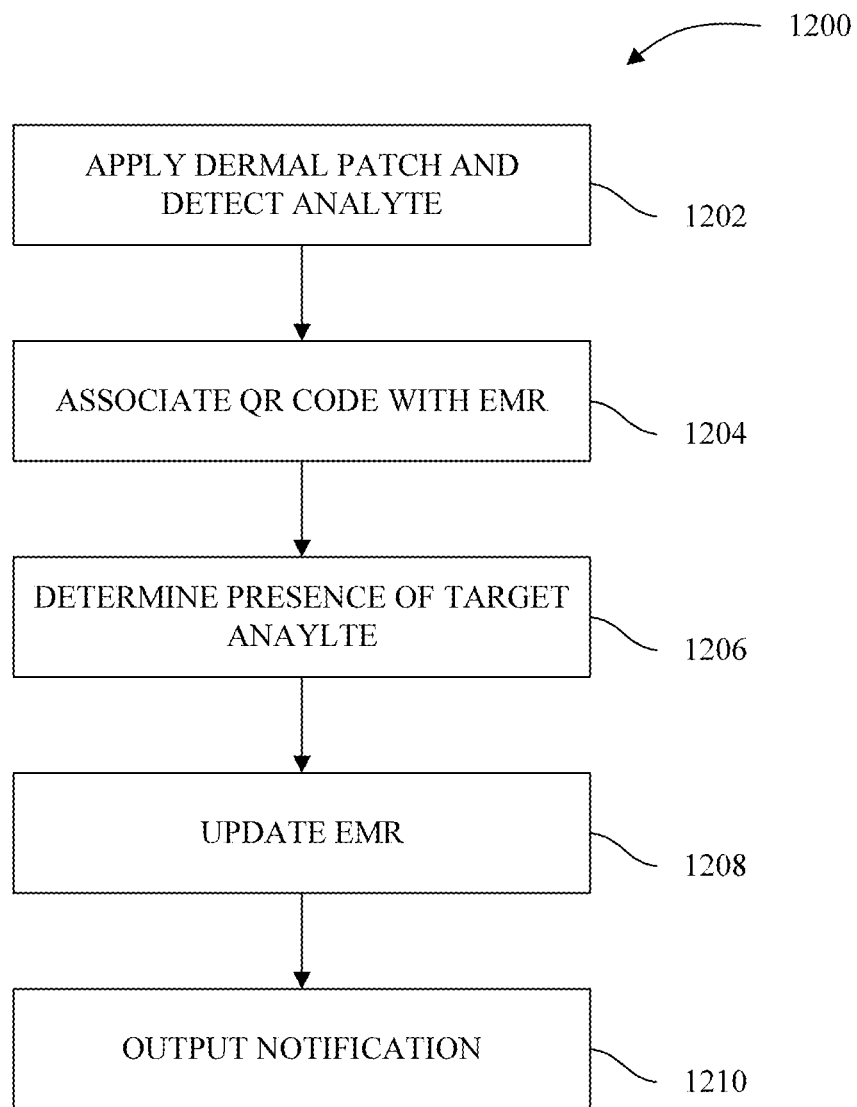
FIG. 23 illustrates a method for automatically updating an electronic medical record ("EMR") in accordance with an exemplary embodiment.

Referring now to FIG. 23, a method 1200 for automatically updating an EMR is shown in accordance with an exemplary embodiment. Steps 1204-1210 of the method 1200 may be stored as computer readable program instructions in a computer readable storage medium (e.g., memory of the computer system 114, memory of a node 904, etc.). A programmed processor (e.g., a processor of the computer system 114, a processor of a node 904, etc.) executes the computer readable program instructions for the steps 1204-1210 of method 1200.

At 1202, the dermal patch 100 is applied to the skin of a subject, and is activated to draw a physiological sample from the subject (e.g., a blood sample or a sample of interstitial fluid) and the detector 110 detects an analyte as previously discussed herein. Stated another way, at 1202 the steps 1002-1012 of the method 1000 are carried out.

At 1204, a user of the computer system 114 scans the QR code 112 with a camera of the computer system 114 as previously discussed herein and a programmed processor analyzes the QR code 112 and associates the QR code 112 with an EMR 118.

At 1206, the programmed processor analyzes an image of the detector read-out (e.g., an image of bands in a lateral flow strip detector) to evaluate the readout of the detector 110 and automatically determine whether a target analyte is present in a physiological sample drawn from the subject, and optionally quantify the target analyte if the target analyte is detected in the sample as previously discussed herein.

At 1208, the programmed processor automatically updates the associated EMR to include the determined presence of the target analyte and/or a level of the target analyte. In some embodiments, at 1208, the programmed processor also updates the associated EMR to include the photograph of the QR code and the detector 110.

At 1210, the programmed processor outputs a notification indicative of the determined presence of the target analyte and/or the determined level of the target analyte to a display in communication with the programmed processor and/or outputs a notification indicative of the determined presence of the target analyte and/or the determined level of the target analyte to another device (i.e., a physician's smartphone).

Figure 24:
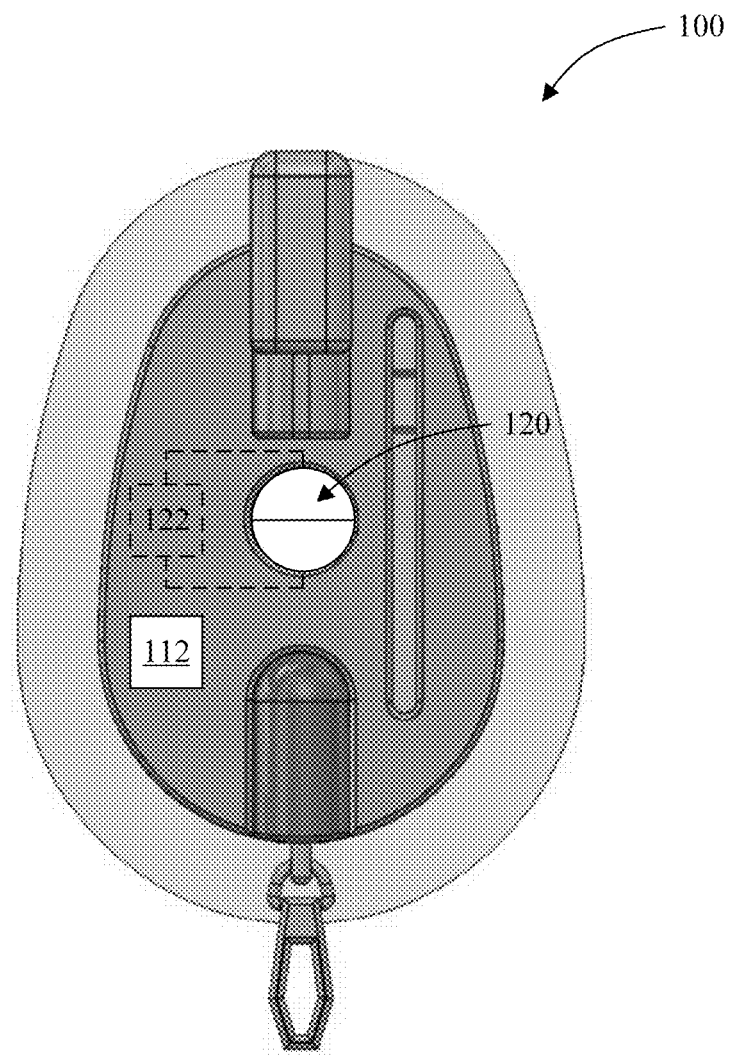
FIG. 24 depicts a dermal patch with a QR code and a moveable cover in a closed position in accordance with an exemplary embodiment.
Figure 25:
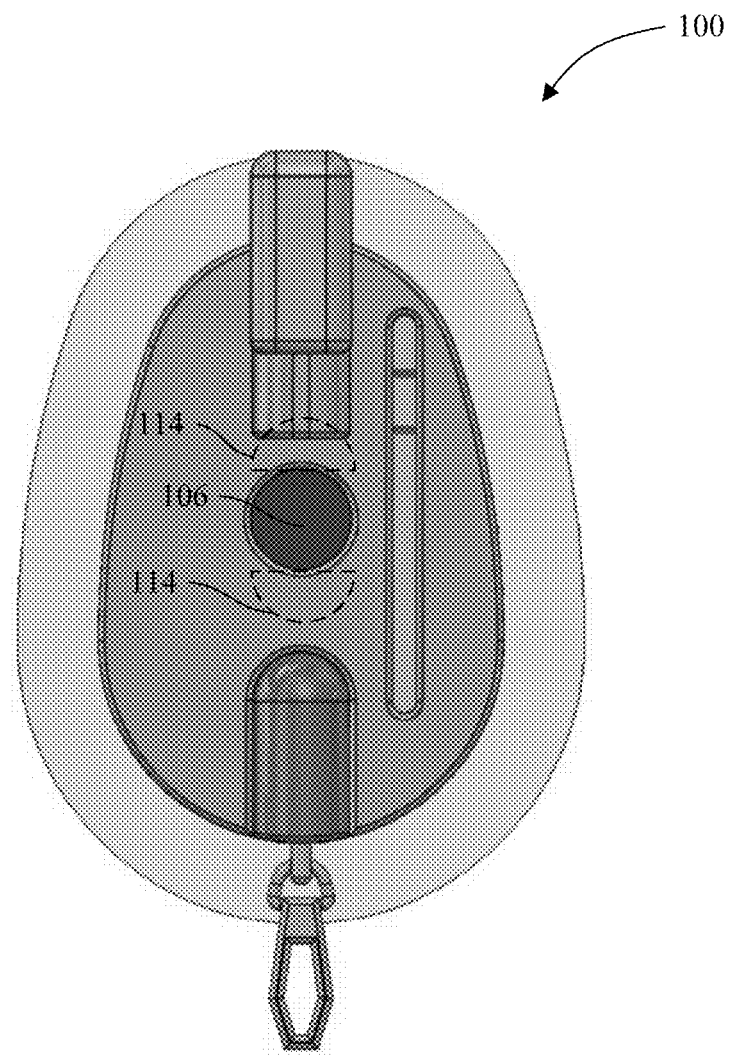
FIG. 25 depicts a dermal patch with a QR code and a moveable cover in an open position in accordance with an exemplary embodiment.

Referring now to FIGS. 24 and 25, in some embodiments the dermal patch 100 may further include a moveable cover 120 and an electromechanical actuator 122 configured to move the moveable cover 120 between a closed positioned (FIG. 24) and an open position (FIG. 25). In the closed position, the moveable cover 120 covers the aperture 102 and the septum 106 and is generally impenetrable. As such, when the moveable cover 120 is in the closed position and the dermal patch 100 has been adhered to the subject, the cover 120 prevents a user from inserting the lancet 108 through the septum 106 and the aperture 102 to draw a physiological sample from the subject. When in the open position the moveable cover 120 is retracted within the dermal patch 100 such that the aperture 102 and the septum 106 are exposed thereby allowing a user to draw a physiological sample from the subject. While FIGS. 24 and 25 depict the dermal patch 100 as including the moveable cover 120, in other embodiments, the dermal patch 100 may include other means that prevent a user of the dermal patch 100 from drawing the physiological sample from the subject.

The electromechanical actuator 122 is connected to and in communication with the computer system 700. As such, the electromechanical actuator 122 is connected to and in communication with the processor 702. In some embodiments, the electromechanical actuator 122 is wirelessly connected to the computer system 700 and in other embodiments the connection between the electromechanical actuator 122 and the computer system 700 is a wired connection. The electromechanical actuator 122 is configured to move the cover 120 from the closed position to the open position in response to receiving a signal from the processor 702 to open the cover 120. Stated another way, the electromechanical actuator 122 is configured to place the dermal patch 100 in a state ready to obtain and optionally analyze a physiological sample in response to a signal from the processor 702.

Figure 26:
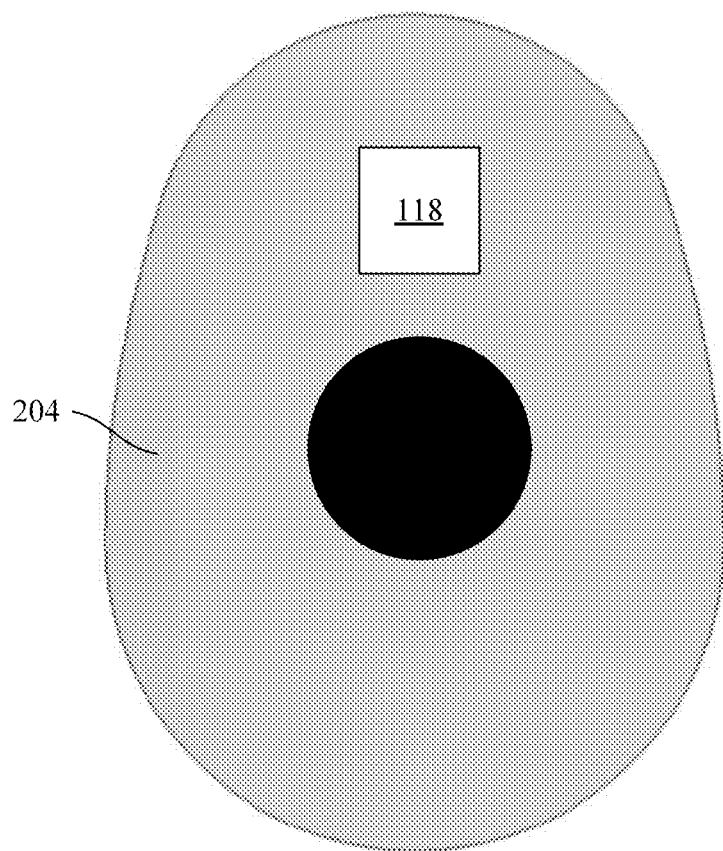
FIG. 26 depicts a bottom surface of a dermal patch with a skin sensor in accordance with an exemplary embodiment.

Referring now to FIG. 26, in some embodiments, the dermal patch 100 further includes a skin sensor 124 located on the bottom surface 204 of the dermal patch 100. The skin sensor 124 is configured to determine when the dermal patch 100 is adhered to the skin of the subject. Stated another way, the skin sensor 124 is configured to determine when the bottom surface 204 contacts skin of a subject. The skin sensor 124 includes, but is not limited to optical sensors, infrared sensors, light sensors, etc.

The skin sensor 124 is connected to and in communication with the computer system 700. As such, the skin sensor 124 is connected to and in communication with the processor 702. In some embodiments, the skin sensor 124 is wirelessly connected to the computer system 700 and in other embodiments the connection between the skin sensor 124 and the computer system 700 is a wired connection. In response to determining the dermal patch is adhered to the skin of the subject, the skin sensor 124 sends a signal to the processor 702 indicating that the dermal patch 100 is adhered to the subject.

In some embodiments, in response to receiving the signal indicating that the dermal patch 100 is adhered to the subject, the processor 702 sends a signal to open the cover 120 to the electromechanical actuator 116. In response to receiving the signal to open the cover 120, the electromechanical actuator 122 moves the cover 120 from the closed position to the open position. Stated another way, the electromechanical actuator 122 opens the cover 120 thereby allowing the user to draw a physiological sample when the dermal patch 100 is adhered to skin of the subject.

As previously discussed, a user may employ a camera of the computer system 114 to scan the QR code 112. In some embodiments, before scanning the QR code 112, the previously discussed installed application may require a user to verify their identity (i.e., by entering a password, scanning a fingerprint, etc.). For example, the installed application may require a user to enter a username and password that is associated with an EMR. In response to verifying the identity of the user, the application may unlock thereby allowing the user to scan the QR code 112. Furthermore, after the application verifies the identity of the user and in response to associating the QR code 112 with the correct EMR as previously discussed herein, the computer system 114 may send a signal indicating that the identity of the user has been verified to the processor 702. In some embodiments, in response to receiving the signal indicating that the identity of the user has been verified, the processor 702 sends a signal to open the cover 120 to the electromechanical actuator 116. In response to receiving the signal to open the cover 120, the electromechanical actuator 122 moves the cover 120 from the closed position to the open position. Stated another way, the electromechanical actuator 122 opens the cover 120 thereby allowing the user to draw a physiological sample when the identity of a user of the dermal patch 100 (i.e., the subject wearing that wears the dermal patch 100) has been verified.

In some embodiments, before sending the signal to open the cover 120, the processor 702 may only send the signal in response to receiving both signal indicating that the identity of the user has been verified as previously discussed herein and a signal indicating that the dermal patch 100 is adhered to the subject as previously discussed herein.

Figure 27:
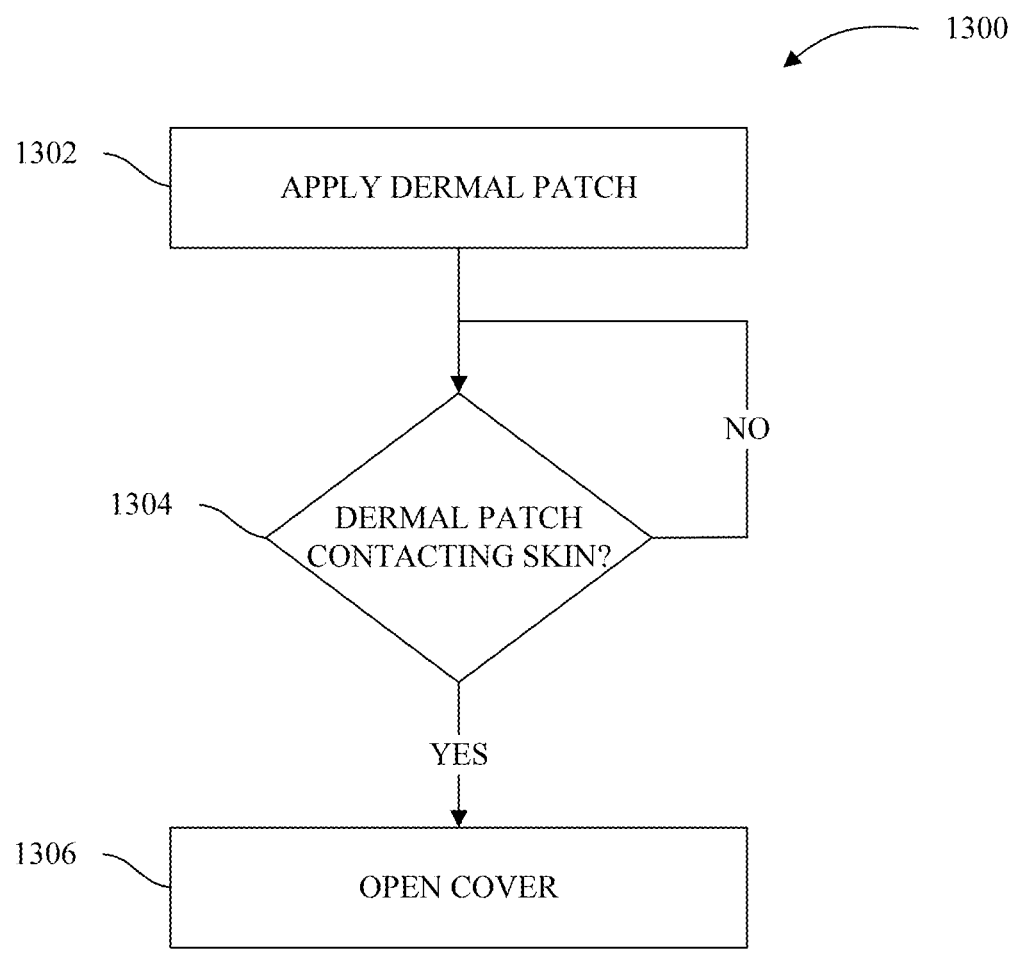
FIG. 27 depicts a method for unlocking a dermal patch to draw a physiological sample in accordance with an exemplary embodiment.

Referring now to FIG. 27, a method 1300 for unlocking the dermal patch 100 to draw a physiological sample is shown in accordance with an exemplary embodiment. Steps 1304 and 1306 of the method 1300 may be stored as computer readable program instructions in a computer readable storage medium. A programmed processor executes the computer readable program instructions for the steps 1304 and 1306 of method 1300.

At 1302, the dermal patch 100 is applied to the skin of a subject via the adhesive patch 104 as previously discussed herein.

At 1304, the skin sensor 124 determines if the dermal patch 100 is adhered to skin of the subject as previously discussed herein and in response to determining the dermal patch 100 is adhered to skin of the subject, the skin sensor 124 sends a signal indicating the dermal patch 100 is adhered to the subject to the processor 702.

At 1306, in response to receiving the signal indicating the dermal patch 100 is adhered to the subject, the programmed processor sends a signal to the electromechanical actuator 116 to open the cover 120. In response to receiving the signal to open the cover 120, the electromechanical actuator 122 transitions the cover 120 from the closed position to the open position as previously discussed herein.

Figure 28:
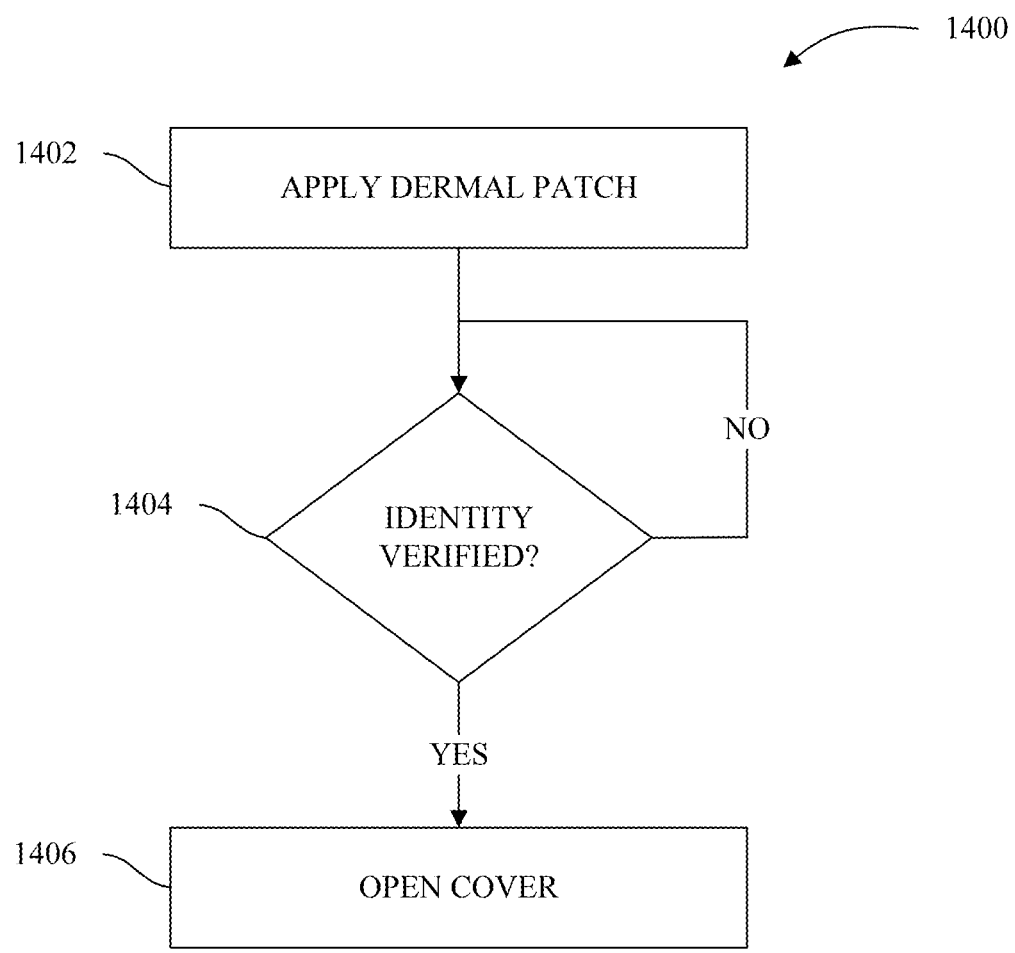
FIG. 28 depicts another method for unlocking a dermal patch to draw a physiological sample in accordance with an exemplary embodiment.

Referring now to FIG. 28, another method 1400 for unlocking the dermal patch 100 to draw a physiological sample is shown in accordance with an exemplary embodiment. Steps 1404 and 1406 of the method 1400 may be stored as computer readable program instructions in a computer readable storage medium. A programmed processor executes the computer readable program instructions for the steps 1404 and 1406 of method 1400.

At 1402, the dermal patch 100 is applied to the skin of a subject via the adhesive patch 104 as previously discussed herein.

At 1404, a user scans the QR code 112 and the computer system 114 verifies the identity of the user as previously discussed herein. In response to verifying the identity of the user, the computer system 114 sends a signal indicating that the identity of the user has been verified to the processor 702 as previously discussed herein.

At 1406, in response to receiving the signal indicating that the identity of the user has been verified, the programmed processor sends a signal to the electromechanical actuator 116 to open the cover 120. In response to receiving the signal to open the cover 120, the electromechanical actuator 122 transitions the cover 120 from the closed position to the open position as previously discussed herein.

Figure 29:
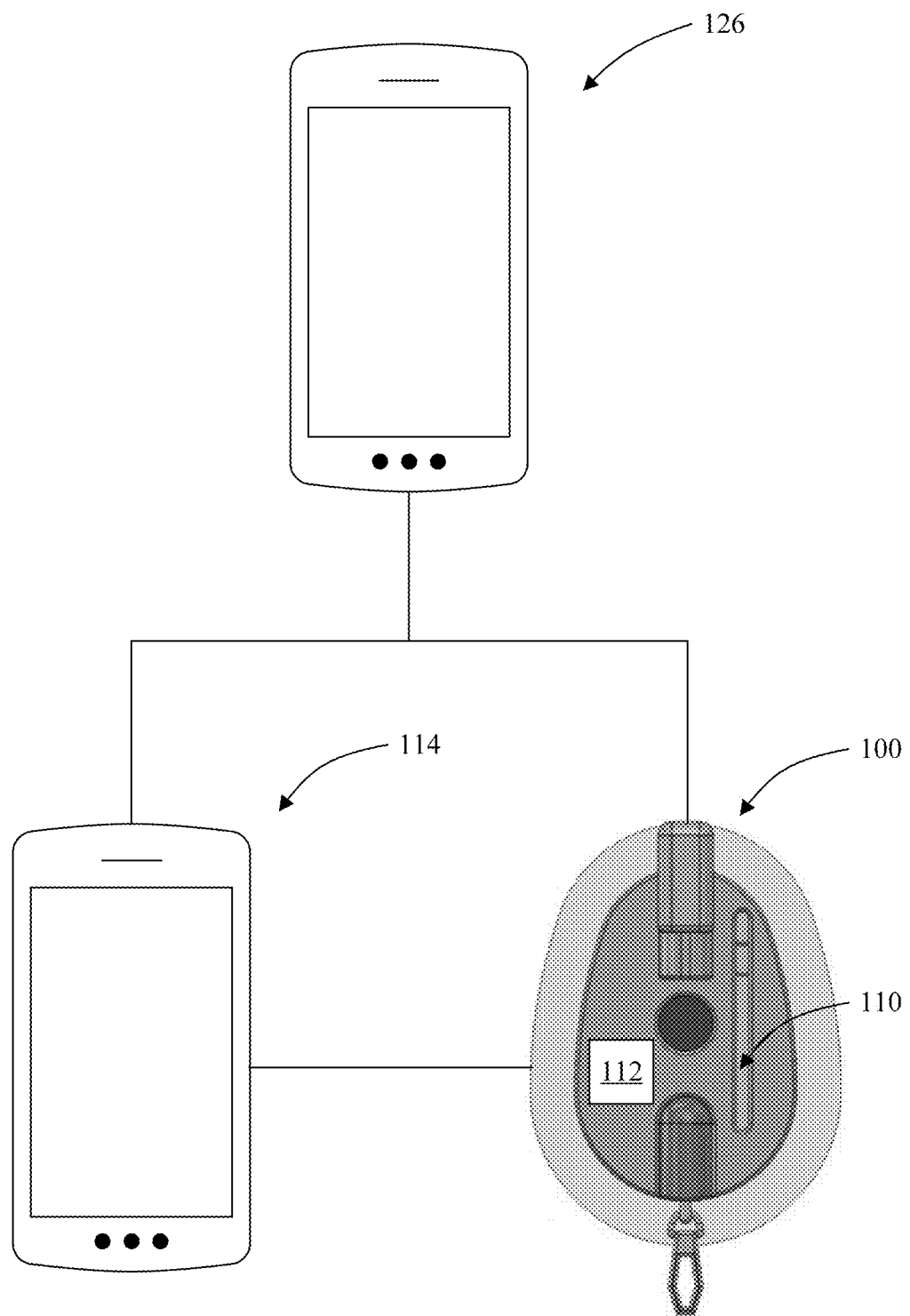
FIG. 29 depicts a dermal patch in communication with two smartphones in accordance with an exemplary embodiment.

Referring now to FIG. 29, a medical professional's computer system 126 is depicted in accordance with an exemplary embodiment. While FIG. 29 depicts the medical professional's computer system 126 as a smartphone, in other embodiments the medical professional's computer system 126 may be another type of computer system (i.e., a tablet, laptop, etc.). As depicted in FIG. 29, the medical professional's computer system 126 may be connected to and in communication with one of or both of the computer system 114 and the computer system 700 (i.e., when the medical professional's computer system 126, the computer system 114, and/or the computer system 700 are connected to a same network).

As previously discussed herein, the processor 702 may receive a signal indicating that the dermal patch 100 is adhered to the subject's skin from the skin sensor 124 or a signal indicating that the identity of the user has been verified. In response to receiving one or both of these signals, in the processor 702 may send a signal indicating that the dermal patch 100 is ready for operation to a processor of the medical professional's computer system 126. In some embodiments, after verifying the identity of the user as previously discussed herein, a processor of the computer system 114 sends a signal indicating that the dermal patch 100 is ready for operation to the medical professional's computer system 126.

In response to receiving the signal indicating that the dermal patch 100 is ready for operation, the processor of the medical professional's computer system 126 causes a display of the medical professional's computer system 126 to display a notification indicating the dermal patch 100 is ready for operation and displays a GUI with an actuatable icon that when selected by the medical professional sends a signal to open the cover 120 to the processor 702. In response to receiving the signal to open the cover 120, the processor 702 causes the actuator 122 to open the cover 120 as previously discussed herein.

Figure 30:
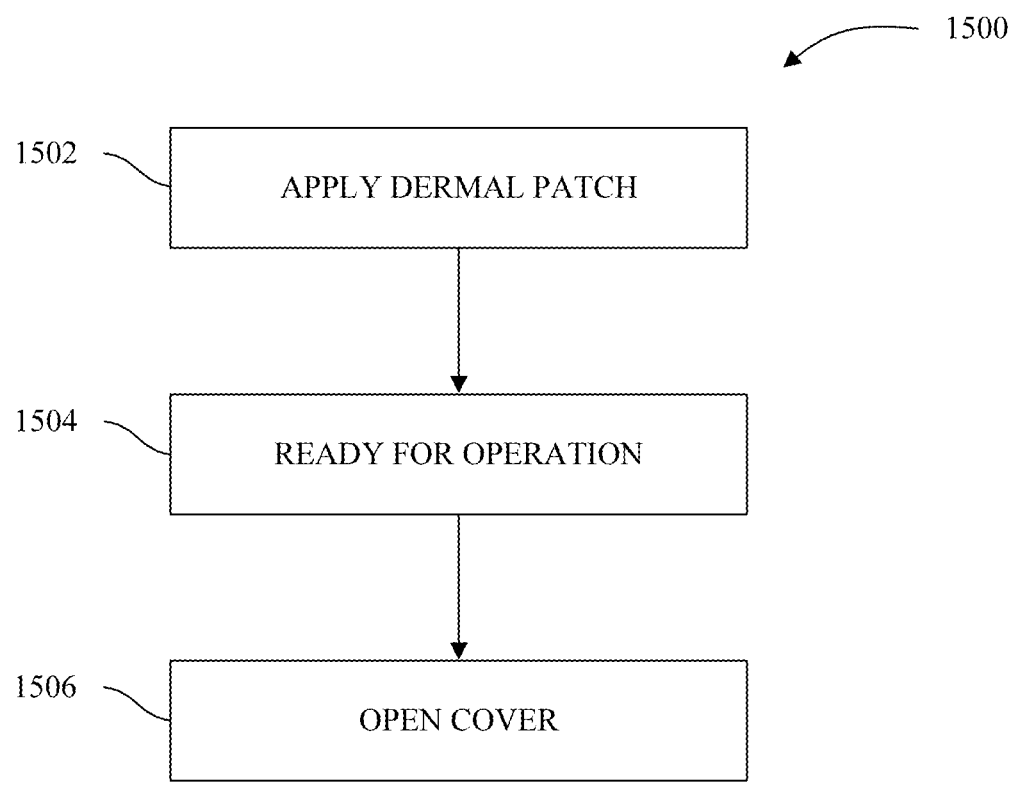
FIG. 30 depicts another method for unlocking a dermal patch to draw a physiological sample in accordance with an exemplary embodiment.

Referring now to FIG. 30, another method 1500 for unlocking the dermal patch 100 to draw a physiological sample is shown in accordance with an exemplary embodiment. Steps 1504 and 1506 of the method 1500 may be stored as computer readable program instructions in a computer readable storage medium. A programmed processor executes the computer readable program instructions for the steps 1504 and 1506 of method 1500.

At 1502, the dermal patch 100 is applied to the skin of a subject via the adhesive patch 104 as previously discussed herein.

At 1504, a programmed processor sends a signal indicating the dermal patch 100 is ready for operation to a medical professional's computer system 126 in response to verifying an identity of a user and/or in response to determining the dermal patch 100 is adhered to skin of a subject as previously discussed herein. Furthermore, at 1504, in response to a medical professional selecting an icon displayed in a GUI of a display of the medical professional's computer system 126, the medical professional's computer system 126 sends a signal to open the cover 120 to the processor 702 as previously discussed herein.

At 1506, in response to receiving the signal to open the cover 120, the programmed processor 702 causes the actuator 122 to open the cover 120 as previously discussed herein.

While the methods 1300, 1400, and 1500 include the processor 702 causing the actuator 122 to move the cover 120 to the open position in response to receiving one of a signal indicating the dermal patch 100 is adhered to the subject or a signal indicating that the identity of the user has been verified or in response to receiving a signal to open the cover 120 from the medical professional's computer system 126, in other embodiments, the processor 702 sends the signal to open the cover 120 in response to receiving more than one of the previously recited signals.

Figure 31:
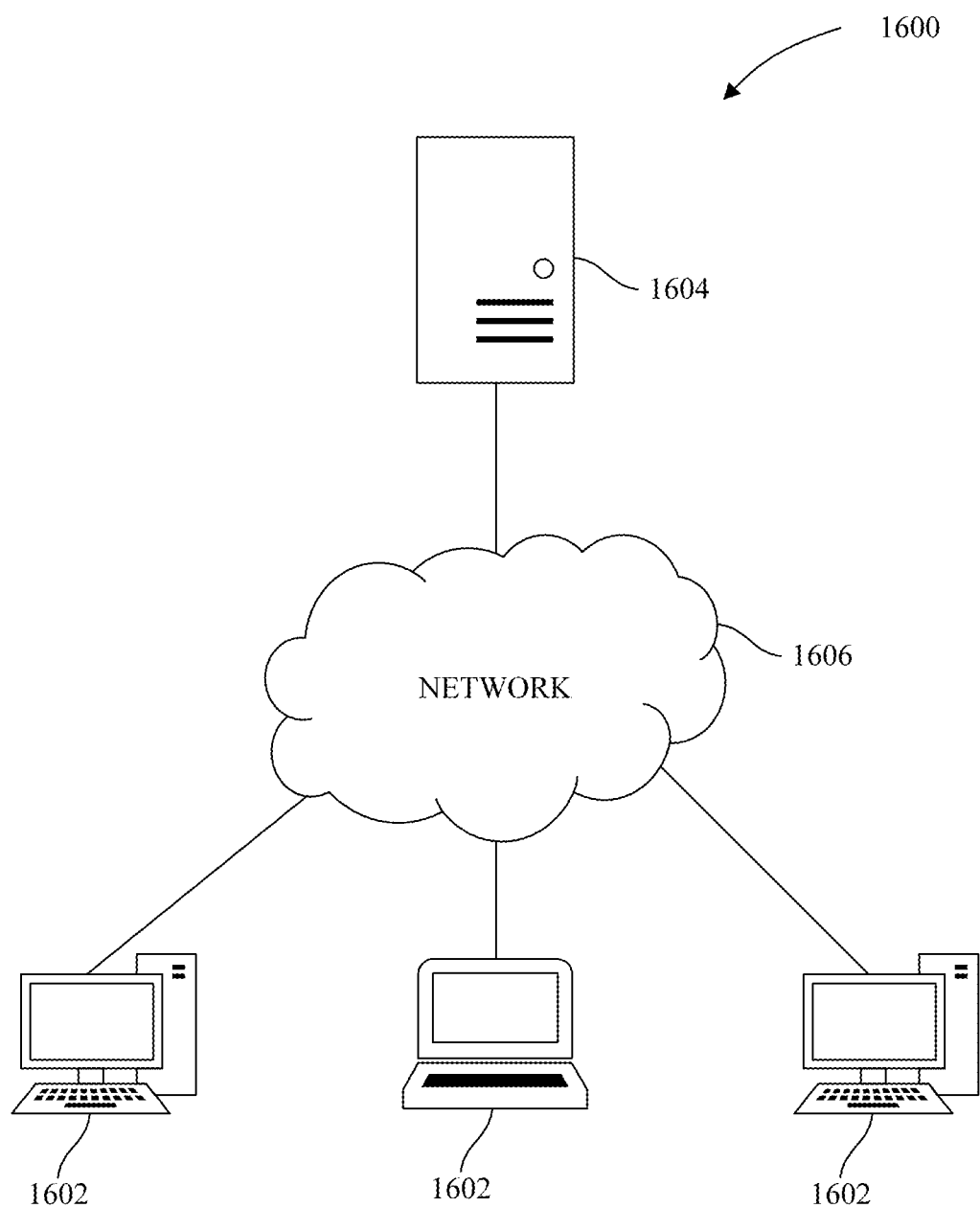
FIG. 31 depicts a metaverse network in accordance with an exemplary embodiment.

Referring now to FIG. 31, a metaverse network 1600 is shown in accordance with an exemplary embodiment. The metaverse network 1600 includes a plurality of user computer systems 1602, a metaverse server 1604, and a network 1606. In some embodiments, the computer systems 1602 may include one or more of the computer system 700, the computer system 114 and the medical professional's computer system 126. While FIG. 13 depicts the metaverse network 1600 as including three user computer systems 1602 and one metaverse sever 1604, in other embodiments the metaverse network 1600 may include more or less user computer systems 1602 (e.g. 2, 5, 7, etc.) and more than one metaverse server 1604 (e.g., 2, 3, 6, etc.). The user computer systems 1602 are connected to and interface with the metaverse server 1604 via a network (e.g., a local area network (LAN), a wide area network (WAN), a public network (the Internet), etc.).

The metaverse server 1604 hosts a virtual reality environment and/or an augmented reality environment (hereinafter "a metaverse") with which the users of a computer system 1602 may interact. In one embodiment, a specified area of the metaverse is simulated by a single server instance and the metaverse server 1604 may include a plurality of instances. The metaverse server 1604 may also include a plurality of physics servers configured to simulate and manage interactions, collisions, etc. between characters and objects within the metaverse. The metaverse server 1604 may further include a plurality of storage servers configured to store data relating to characters, media, objects, related computer readable program instructions, etc. for use in the metaverse.

The network 1606 may employ traditional internet protocols to allow communication between user computer systems 1602 and the metaverse server 1604. In some embodiments, the user computer systems 1602 may be directly connected to the metaverse server 1604.

Figure 32:
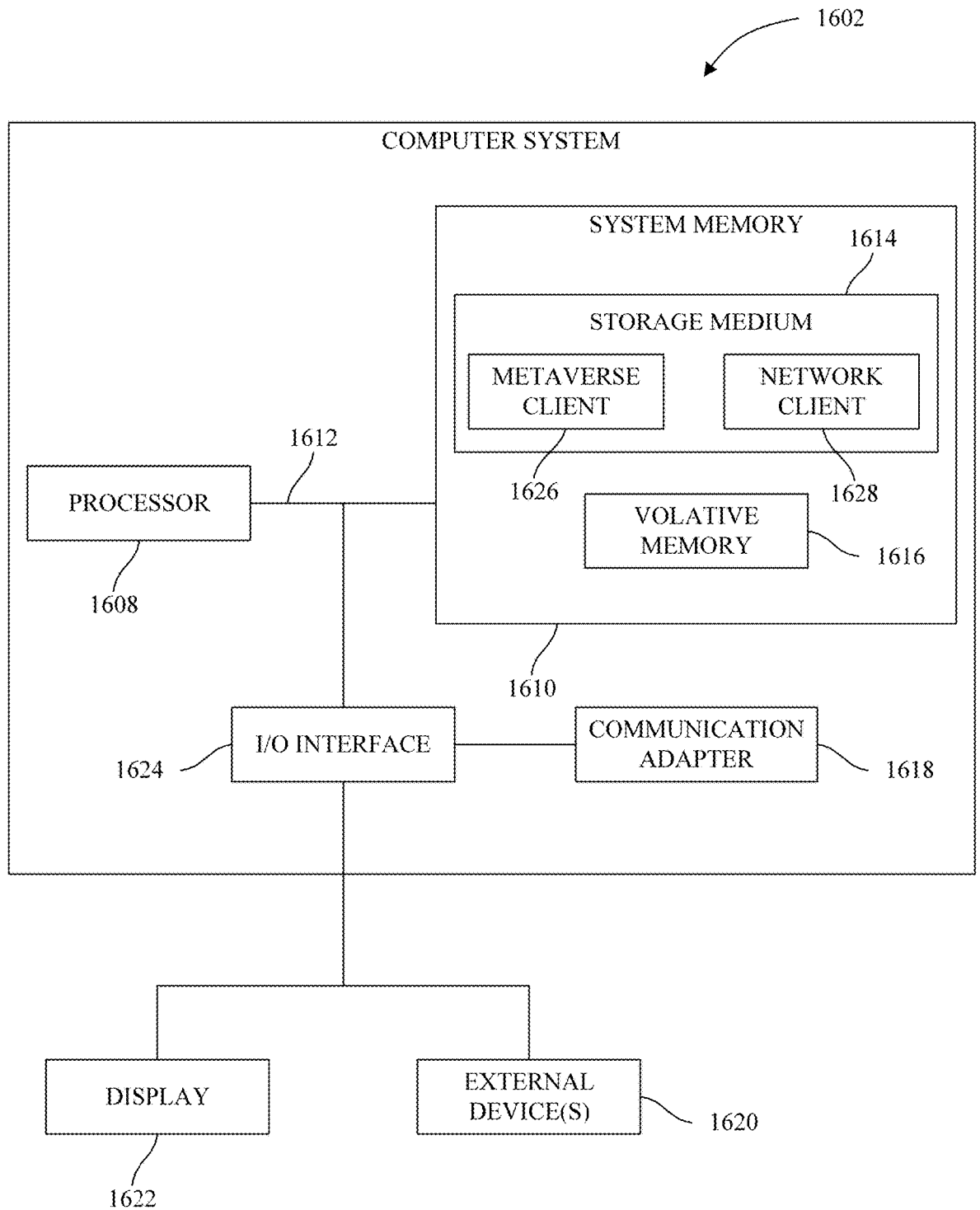
FIG. 32 diagrammatically a computer system that can connect to a metaverse network in accordance with an exemplary embodiment.
Figure 33:
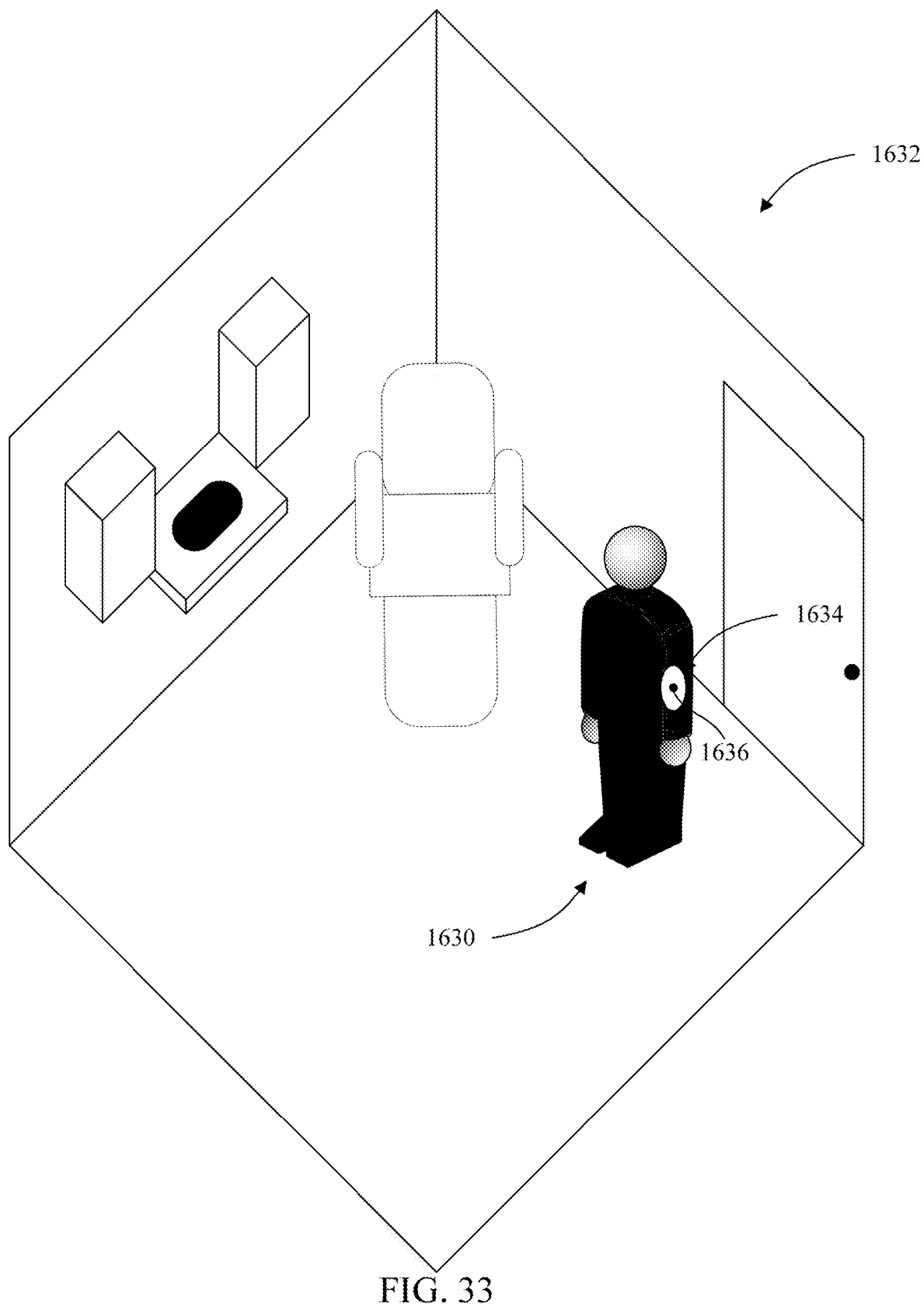
FIG. 33 depicts a metaverse in accordance with an exemplary embodiment.

Referring now to FIG. 32 a user computer system 1602 is shown in accordance with an exemplary embodiment. Generally, the user computer system 1602 includes the same or similar components that operate in a same or similar manner as the components of the computer system 700 (i.e., a processor 1608, system memory 1610, a bus 1612, a computer readable storage medium 1614, volatile memory 1616, a communication adapter 1618, one or more external devices 1620, a display 1622, and an I/O interface 1624). For the sake of brevity, these components are shown, but are not discussed in further detail herein.

The computer system 1602 also includes a metaverse client 1626 and a network client 1628. The metaverse client 1626 and the network client 1628 include computer readable program instructions that may be executed by a processor 1608 of the user computer system 1602. While FIG. 23 depicts the computer readable storage medium 1614 as including the metaverse client 1626 and the network client 1628, in other embodiments the metaverse client 1626 and the network client 1628 may be stored in a different location that is accessible to the processor 1608 (i.e., in a storage element of the cloud computing environment 900).

When executed, the metaverse client 1626 allows a user of a computer system 1602 to connect to the metaverse server 1604 via the network 1606 thereby allowing a user of the user computer system 1602 to interact with the metaverse provided by the metaverse server 1604. The metaverse client 1626 further allows a user of a user computer system 1602 to interact with other users of other computer systems 1602 that are also connected to the metaverse server 1604.

The network client 1628, when executed by the processor 1608, facilities connection between the user computer system 1602 and the metaverse server 1604 (i.e., by verifying credentials provided by the user). For example, when executed and a user of a computer system 1602 requests to log onto the metaverse server 1604, the network client 1628 maintains a stable connection between the user computer system 1602 and the metaverse server 1604 and handles commands input by a user of a computer system 1602 and handles communications from the metaverse server 1604.

When a user of the user computer system 1602 is logged into the metaverse server 1604, the display 1622 conveys a visual representation of a metaverse provided by the metaverse server 1604. In some embodiments wherein a computer system 1602 is a VR headset and the VR headset includes the display 1622, the metaverse server 1602 provides a three-dimensional ("3D") environment to the VR headset thereby creating a lifelike environment for the user.

In one embodiment, wherein the computer systems 700 and 114 are user computer systems 1602 (and therefore include the metaverse client 1626 and the network client 1628), a user of the dermal patch may log into the metaverse server 1604 by verifying their identity as previously discussed herein. In response to verifying the identity of a user, the computer system 700 sends a signal indicating the user identity has been verified to the metaverse server 114 and thereby logging the computer systems 700 and 114 into the metaverse.

When a user computer system 1602 logs into the metaverse server 1604, the metaverse server 1604 may generate a subject avatar 1630 corresponding to a user of the dermal patch 100. In some embodiments, the metaverse server 1604 generates a generic subject avatar 1630 that corresponds to the user and in other embodiments, the subject avatar 1630 has been previously generated by the metaverse based on user inputs. When the subject avatar 1630 is based on user inputs, the avatar may look similar to a subject using the dermal patch 100.

With reference to FIG. 24, The metaverse server 1604 also generates a virtual reality environment (or a "metaverse") 1632. In some embodiments, the metaverse 1632 looks like a physician's examination room (i.e., including chairs, examination table, sink, etc.) and may be based on user inputs to create a personalized metaverse 1632. After the subject avatar 1630 is generated, the metaverse server 1604 populates the subject avatar 1630 into the metaverse 1632.

Furthermore when the computer system 700 and/or the computer system 114 is a user computer system 1602 and is logged into the metaverse server 1604, in response to the skin sensor 124 determining the dermal patch 100 is contacting skin of the subject and sending a signal to the computer system 700 or the computer system 114 indicating the dermal patch 100 is adhered to the subject as previously discussed herein, the computer system 700 or the computer system 114 may send a corresponding signal to the metaverse server 1604. In response to receiving the signal indicating the dermal patch 100 is adhered to skin of the subject, the metaverse server 1604 generates a dermal patch avatar 1634 on the subject avatar 1630. While the dermal patch avatar 1634 is depicted on an arm of the subject avatar 1630, in other embodiments, the dermal patch avatar 1634 may be depicted as attached to different parts of the subject avatar 1630 (i.e., on a leg of the subject avatar).

The dermal patch avatar 1634 includes an actuatable button 1636. When a user within the metaverse selects the actuatable button 1636, the metaverse server 1604 sends a signal to the processor 702 of the dermal patch 100 to open the cover 120. In response to receiving the signal to open the cover 120 from the metaverse server 1604, the processor 702 causes the electromechanical actuator to open the cover 120 as previously discussed herein. Stated another way, a user in the metaverse 1632 may place the dermal patch 100 in a ready position (i.e., by opening the cover 120) by pushing a button 1636 of a virtual dermal patch 1634.

In some embodiments, the actuatable button 1636 may only be actuated by a user of a computer system 1602 with specific login credentials (i.e., a medical professional). Stated another way, only a user with medical professional credentials may cause the dermal patch 100 to enter a ready position by actuating the actuatable button 1636.

In some embodiments, wherein a user computer system 1402 includes a VR headset that is connected to the metaverse server 1604, a user may view the metaverse 1632 via a display of the VR headset. Furthermore, when the metaverse 1632 includes the subject avatar 1630 with the dermal patch avatar 1634, the VR headset may track the hands of the user in the VR headset to determine when the user "pushes" (and therefore selects) the actuatable button 1636. In response to determining the user pushed the actuatable button 1636, the VR headset (the user computer system 1402) sends a signal to the metaverse server 1604 indicating a user has selected the actuatable button 1636. In response to receiving this signal, the metaverse server 1636 causes the dermal patch 100 to be placed into a ready position.

In some embodiments, wherein a medical professional logs into the metaverse server 1604 via their login credentials, the metaverse server may populate a corresponding avatar (e.g., a medical professional avatar) into the metaverse 1632. In these embodiments, when the medical professional selects the actuatable button 1636 the metaverse server depicts the medical professional's avatar as interacting with the dermal patch avatar 1634.

While the above describes the dermal patch 100 as being capable of connecting with the metaverse server 1604, in other embodiments, the dermal patch 800 may include a moveable cover and a computer system that allows the dermal patch 800 to connect to the metaverse as discussed herein. In this embodiment, the dermal patch 800 may be placed in a ready position by a user selecting an actuatable button in the metaverse as previously discussed herein.

While the invention has been illustrated and described in detail in the drawings and foregoing description, such illustration and description are to be considered illustrative or exemplary and not restrictive; embodiments of the present disclosure are not limited to the disclosed embodiments. Other variations to the disclosed embodiments can be understood and effected by those skilled in the art in practicing embodiments of the present disclosure, from a study of the drawings, the disclosure, and the appended claims.

In the claims, the word "comprising" does not exclude other elements or steps, and the indefinite article "a" or "an" does not exclude a plurality. A single processor or other processing unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

What is claimed is:

1. A system comprising:
   a dermal patch comprising a housing configured to attach to a subject's skin,
      wherein the housing includes an opening to provide access to the subject's skin when the dermal patch is attached to the subject's skin;
   a lancet configured to engage with the opening, wherein the lancet includes a needle movable from an undeployed position to a deployed position, and wherein in the deployed position, the needle is configured to puncture the skin to draw a physiological sample; and
   a fluid pouch coupled to the housing, wherein the fluid pouch is configured to store a processing fluid and wherein the fluid pouch is formed of a frangible membrane; and
   a slider coupled to the housing, wherein the housing further includes a puncture element, and wherein the slider is configured to compress the fluid pouch into the puncture element to rupture the fluid pouch.

2. A system comprising:
   a dermal patch comprising a housing configured to attach to a subject's skin,
      wherein the housing includes an opening to provide access to the subject's skin when the dermal patch is attached to the subject's skin;
   a lancet configured to engage with the opening, wherein the lancet includes a needle movable from an undeployed position to a deployed position, and wherein in the deployed position, the needle is configured to puncture the skin to draw a physiological sample;
   a moveable pin disposed within the housing, wherein the pin is configured to generate a vacuum within the housing when moved, and wherein the vacuum generated by the pin is proportional to the movement of the pin; and
   a receptacle, wherein the pin is disposed within the receptacle, and wherein the pin is configured to seal the receptacle.

3. The system of claim 2, wherein the housing further includes:
   a chamber configured to receive the drawn physiological sample, and
   a channel in open communication with the chamber and the receptacle,
      wherein the pin is configured to generate the vacuum within the channel to draw the drawn physiological sample to the chamber.

\* \* \* \* \*